US010875919B2

(12) United States Patent
Rosenthal

(10) Patent No.: US 10,875,919 B2
(45) Date of Patent: Dec. 29, 2020

(54) CHIMERIC RECEPTORS AND METHODS OF USE THEREOF

(71) Applicant: ALECTOR LLC, South San Francisco, CA (US)

(72) Inventor: Arnon Rosenthal, Woodside, CA (US)

(73) Assignee: ALECTOR LLC, South San Francisco, CA (US)

(*) Notice: Subject to any disclaimer, the term of this patent is extended or adjusted under 35 U.S.C. 154(b) by 0 days.

(21) Appl. No.: 15/498,004

(22) Filed: Apr. 26, 2017

(65) Prior Publication Data
US 2018/0186878 A1 Jul. 5, 2018

Related U.S. Application Data

(60) Provisional application No. 62/327,954, filed on Apr. 26, 2016.

(51) Int. Cl.
| C07K 16/28 | (2006.01) |
| A61K 39/395 | (2006.01) |
| C07K 14/705 | (2006.01) |
| C07K 14/725 | (2006.01) |
| C07K 16/24 | (2006.01) |
| A61K 39/00 | (2006.01) |

(52) U.S. Cl.
CPC ...... *C07K 16/2803* (2013.01); *A61K 39/3955* (2013.01); *C07K 14/7051* (2013.01); *C07K 14/70517* (2013.01); *C07K 16/244* (2013.01); *A61K 2039/507* (2013.01); *C07K 2317/53* (2013.01); *C07K 2317/622* (2013.01); *C07K 2317/76* (2013.01); *C07K 2319/02* (2013.01); *C07K 2319/03* (2013.01); *C07K 2319/30* (2013.01)

(58) Field of Classification Search
CPC .................................. C07K 14/7051
See application file for complete search history.

(56) References Cited

U.S. PATENT DOCUMENTS

| 4,657,760 | A | 4/1987 | Kung et al. |
| 5,206,344 | A | 4/1993 | Katre et al. |
| 5,225,212 | A | 7/1993 | Martin et al. |
| 5,641,870 | A | 6/1997 | Rinderknecht et al. |
| 9,511,092 | B2 | 12/2016 | Campana et al. |
| 2014/0328812 | A1* | 11/2014 | Campana ........... C07K 16/2866 424/93.21 |
| 2017/0073638 | A1 | 3/2017 | Campana et al. |
| 2018/0186855 | A1 | 7/2018 | Rosenthal |
| 2019/0233496 | A1 | 8/2019 | Rosenthal |

FOREIGN PATENT DOCUMENTS

| EP | 0404097 A2 | 12/1990 |
| WO | WO-1993/11161 A1 | 6/1993 |

OTHER PUBLICATIONS

Sadelain et al., Cancer Discov. 3(4):388-98 (Year: 2013).*
Dotti et al., Immunol Rev. 257(1): doi:10.1111/imr/12131 (Year: 2014).*
Geldres et al., Sem Immunol 28:3-9 (Year: 2016).*
Fesnak et al., Nature Reviews Cancer 16:566-581 (Year: 2016).*
De Oliveira et al., Human Gene Ther. 24:824-39 (Year: 2013).*
Chattopadhyay & Sen, Cytokines & Growth Factors Rev 25:533-541 (Year: 2014).*
D. Kabelitz, Current Opin. Immunol. 19:39-45 (Year: 2007).*
Biglari et al, Gene Therapy 13:602-10 (Year: 2006).*
Yong et al., PLoS One 10(10):e014053 (Year: 2015).*
Beattie, M.S. et al. (Oct. 24, 2002). "ProNGF Induces p75-Mediated Death of Oligodendrocytes following Spinal Cord Injury," *Neuron* 36(3):375-386.
Brentjens, R.J. et al. (Nov. 3, 2011; e-pub. Aug. 17, 2011). "Safety and Persistence of Adoptively Transferred Autologous CD19-Targeted T Cells in Patients with Relapsed or Chemotherapy Refractory B-Cell Leukemias," *Blood* 118(18):4817-4828.
Capel, P.J.A. et al. (1994). "Heterogeneity of Human IgG Fc Receptors," *ImmunoMethods* 4:25-34.
Cartellieri, M. et al. (2010). "Chimeric Antigen Receptor-Engineered T Cells for Immunotherapy of Cancer," *Journal of Biomedicine and Biotechnology* 2010(Article ID 956304):1-13.
Cattepoel, S. et al. (Apr. 5, 2011). Chronic Intranasal Treatment with an Anti-Ab30-42 scFv Antibody Ameliorates Amyloid Pathology in a Transgenic Mouse Model of Alzheimer's Disease, *PLoS ONE* 6(4):e18296, 13 pages.
Cruts, M. et al. (2008; e-pub. Mar. 6, 2008). "Loss of Progranulin Function in Frontotemporal Lobar Degeneration," *Trends Genetics* 24(4):186-194.
Daëron, M. (1997). "Fc Receptor Biology," *Annual Review of Immunology* 15:203-204.
Davis, J. et al. (May 7, 2004). "Early-Onset and Robust Cerebral Microvascular Accumulation of Amyloid β-Protein in Transgenic Mice Expressing Low Levels of a Vasculotropic Dutch/Iowa Mutant Form of Amyloid β-Protein Precursor," *The Journal of Biological Chemistry* 279(19):20296-20306.
De Haas, M. et al. (Oct. 1995). "Fcγ Receptors of Phagocytes," *The Journal of laboratory and Clinical Medicine* 126(4):330-341.
Fisher, Y. et al. (May 26, 2010). "T Cells Specifically Targeted to Amyloid Plaques Enhance Plaque Clearance in a Mouse Model of Alzheimer's Disease," *PLoS ONE* 5(5):e10830, 11 pages.
Gate, D. et al. (2010; e-pub. Jun. 2, 2010). "Macrophages in Alzheimer's Disease: The Blood-Borne Identity," *Journal of Neural Transmission* 117:961-970.
Glienke, W. et al. (Feb. 12, 2015). "Advantages and Applications of CAR Expressing Natural Killer Cells," *Frontiers in Pharmacology* 6(Article 21):1-7.
Hamilton, J.A. (Jul. 2008; e-pub. Jun. 13, 2008). "Colony-Stimulating Factors in Inflammation and Autoimmunity," *Nature Reviews Immunology* 8:533-544.
Harrington, A.W. et al. (Apr. 20, 2004). "Secreted proNGF is a Pathophysiological Death-Inducing Ligand after Adult CNS Injury," *PNAS* 101(16):6226-6230.

(Continued)

Primary Examiner — Jessica H Roark
(74) Attorney, Agent, or Firm — Morrison & Foerster LLP

(57) ABSTRACT

The present disclosure is related to compositions that include polynucleotides encoding chimeric receptors, methods of delivering polynucleotides encoding chimeric receptors to immune cells, and methods of using immune cells encoding chimeric receptors to treat or prevent cancer.

8 Claims, 7 Drawing Sheets

Specification includes a Sequence Listing.

(56) References Cited

OTHER PUBLICATIONS

Heppner, F.L. et al. (Jun. 2015). "Immune Attack: The Role of Inflammation in Alzheimer Disease," *Nature Review, Neuroscience* 16:358-372.

Holliger, P. et al. (Jul. 1993). ""Diabodies": Small Bivalent and Bispecific Antibody Fragments," *Proceedings of the National Academy of Sciences* 90:6444-6448.

Ito, H. et al. (Jan. 2012). "TREM-2, Triggering Receptor Expressed on Myeloid Cell-2, Negatively Regulates TLR Responses in Dendritic Cells," *Eur. J. Immunol.* 42(1):176-185.

Kim, J. et al. (Nov. 5, 2012). "Anti-ApoE Immunotherapy Inhibits Amyloid Accumulation in a Transgenic Mouse Model of Aβ Amyloidosis," *The Journal of Experimental Medicine* 209(12):2149-2156.

Laird, A.S. et al. (Oct. 13, 2010). "Progranulin is Neurotrophic in Vivo and Protects against a Mutant TDP-43 Induced Axonopathy," *PLOS ONE* 5(10):e13368, seven pages.

Langer, R. (Sep. 28, 1990). "New Methods of Drug Delivery," *Science* 249:1527-1533.

Latouche, J.-B. et al. (Apr. 2000). "Induction of Human Cytotoxic T Lymphocytes by Artificial Antigen-Presenting Cells," *Nature Biotechnology* 18:405-409.

Lebson, L. et al. (Jul. 21, 2010). "Trafficking CD11b-Positive Blood Cells Deliver Therapeutic Genes to the Brain of Amyloid Depositing Transgenic Mice," *The Journal of Neuroscience* 30(29):9651-9658.

Meyer-Luehmann, M. et al. (Oct. 2015). "Myeloid Cells in Alzheimer's Disease: Culprits, Victims or Innocent Bystanders?," *Trends in Neuroscience* 38(10):659-668.

Milone, M.C. et al. (Aug. 2009; e-pub. Apr. 21, 2009). "Chimeric Receptors Containing CD137 Signal Transduction Domains Mediate Enhanced Survival of T Cells and Increased Antileukemic Efficacy in Vivo," *Molecular Therapy* 17(8):1453-1464.

Mordenti, J. et al. (1989). "The Use of Interspecies Scaling in Toxicokinetics," Chapter 4 in *Toxicokinetics New Drug Development*, Yacobi, A. ed. et al., Pergamon Press, Inc. NY, pp. 42-46.

Neary, D. et al. (Dec. 1998). "Frontotemporal Lobar Degeneration: A Consensus on Clinical Diagnostic Criteria," *Neurology* 51:1546-1554.

Neumann, M. et al. (Oct. 2007). "TDP-43 Proteinopathy in Frontotemporal Lobar Degeneration and Amyotrophic Lateral Sclerosis," *Arch. Neurol.* 64(10):1388-1394.

Peng, Q. et al. (May 18, 2010). "TREM2- and DAP12-Dependent Activation of PI3K Requires DAP10 and Is Inhibited by SHIP1," *Science Signaling* 3(122):1-15.

Poliani, P.L. et al. (May 2015). "TREM2 Sustains Microglial Expansion during Aging and Response to Demyelination," *The Journal of Clinical Investigation* 125(5):2161-2170.

Prinz, M. et al. (Oct. 2011; e-pub. Sep. 27, 2011)). "Heterogeneity of CNS Myeloid Cells and their Roles in Neurodegeneration," *Nature Neuroscience* 14(10):1227-1235.

Ratnavalli, E. et al. (Jun. (1 of 2) 2002). "The Prevalence of Frontotemporal Dementia," *Neurology* 58:1615-1621.

Ravetch, J.V. et al. (1991). "Fc Receptors," *Annual Review Immunology* 9:457-492.

Schymick, J.C. et al. (2007). "Progranulin Mutations and Amyotrophic Lateral Sclerosis or Amyotrophic Lateral Sclerosis-Frontotemporal Dementia Phenotypes," *Journal of Neurology Neurosurgery and Psychiatry* 78:754-756.

Srivastava, S. et al. (Aug. 2015). "Engineering CAR-T cells: Design Concepts," *Trends in Immunology* 36(8):494-502.

Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," *PLoS Medicine* 4(4):(e124), pp. 0675-0689.

Takahashi, K. et al. (Feb. 21, 2005). "Clearance of Apoptotic Neurons without Inflammation by Microglial Triggering Receptor Expressed on Myeloid Cells-2," *The Journal of Experimental Medicine* 201(4):647-657.

Turnbull, I.R. et al. (Feb. 2007). "Activating and Inhibitory Functions of DAP12," *Nature Reviews Immunology* 7:155-161.

Wang, L. et al. (2015). "Application of Chimeric Antigen Receptor-Modified CA R-T/NK Cells to Treatment of Multiple Myeloma-Review," *Journal of Experimental Hematology* 23(2):568-572. (English Abstract only).

Witkowski, W. et al. (Jul. 24, 2015). "VPX-Independent Lentiviral Transduction and shRNA-Mediated Protein Knock-Down in Monocyte-Derived Dendritic Cells," *PLOS ONE* 10(7):e0133651, twelve pages.

Wyss-Coray, T. et al. (2012). "Inflammation in Alzheimer Disease—A Brief Review of the Basic Science and Clinical Literature," *Cold Spring Harbor Perspectives in Medicine* 2:1-23.

Xu, J.L.et al. (Jul. 2000). "Diversity in the CDR3 Region of $V_H$ is Sufficient for Most Antibody Specificities," *Immunity* 13:37-45.

Zapata, G. et al. (1995). "Engineering Linear $F(ab')_2$ Fragments for Efficient Production in *Escherichia coli* and Enhanced Antiproliferative Activity," *Protein Engineering* 8(10):1057-1062.

Zhao, M. et al. (2014). "Pan-Amyloid Oligomer Specific scFv Antibody Attenuates Memory Deficits and Brain Amyloid Burden in Mice with Alzheimer's Disease," *Current Alzheimer Research* 11(1):69-78.

Harrer et al., (2018). "Chimeric Antigen Receptors in Different Cell Types: New Vehicles Join the Race," Human Gene Therapy, 29(5):547-558.

Morrissey et al., (2018). "Chimeric Antigen Receptors that Trigger Phagocytosis," *eLife* 7:e36688, 21 pages.

Suh et al., (2017). "Effect of Dendritic Cells (DC) Transduced With Chimeric Antigen Receptor (CAR) on CAR T-Cell Cytotoxicity," Journal of Clinical Oncology, 35(7 Supplement 144): Abstract Only, 1 page.

Yong et al., (2016). "A Role for Multiple Chimeric Antigen Receptor-Expressing Leukocytes in Antigen-Specific Responses to Cancer," Oncotarget, 7(23):34582-34598.

Cai et al., (2011). "Activation of Toll-Like Receptor 5 on Breast Cancer Cells by Flagellin Suppresses Cell Proliferation and Tumor Growth," Cancer Res., 71(7):1-16.

Mett et al., (2018). "Mobilan: a recombinant adenovirus carrying Toll-like receptor 5 self-activating cassette for cancer immunotherapy," Oncogene 37:439-449.

Rhee et al., (2008). "Toll-like receptor 5 engagement modulates tumor development and growth in a mouse xenograft model of human colon cancer," Gastroenterology, 135:1-18.

Sfondrini et al., (2006). "Antitumor Activity of the TLR-5 Ligand Flagellin in Mouse Models of Cancer," J. Immunol., 176:6624-30.

\* cited by examiner

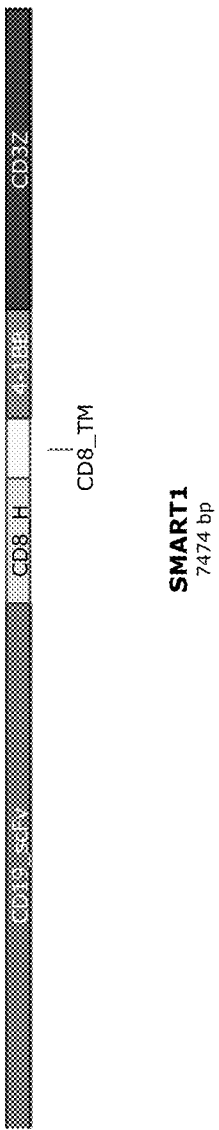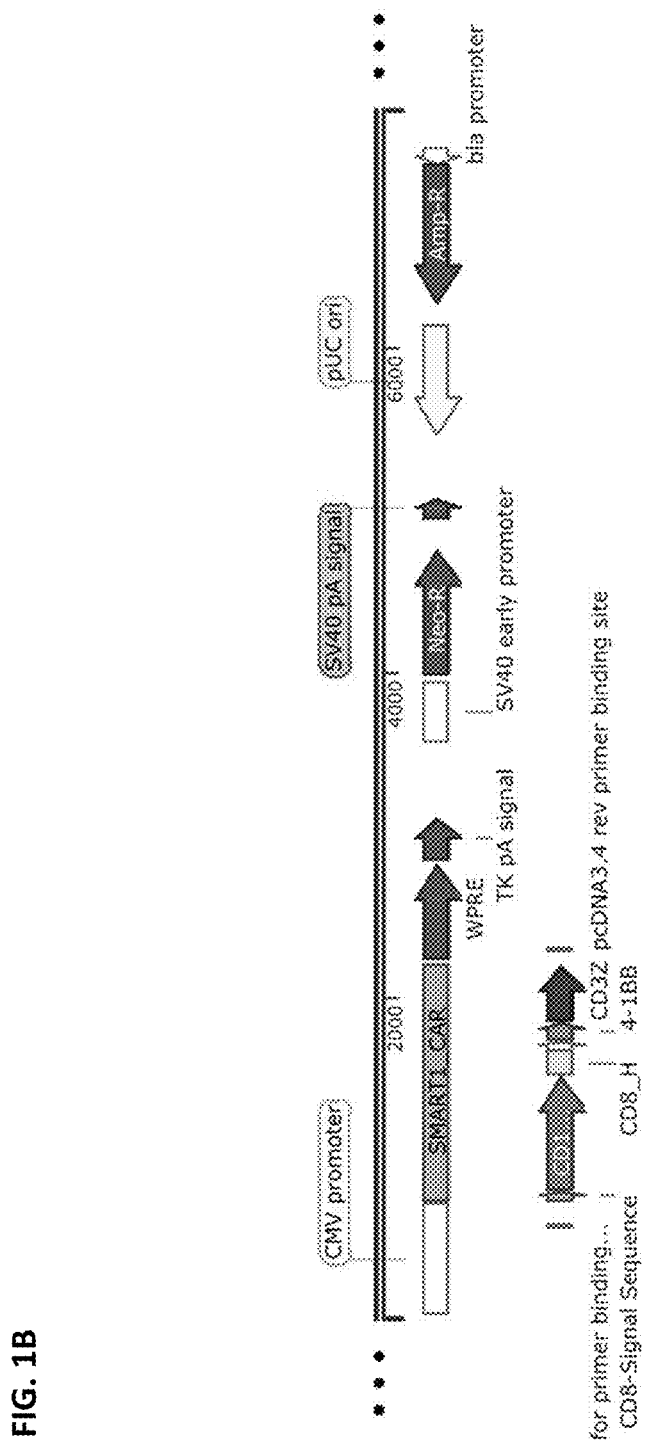
FIG. 1A
FIG. 1B

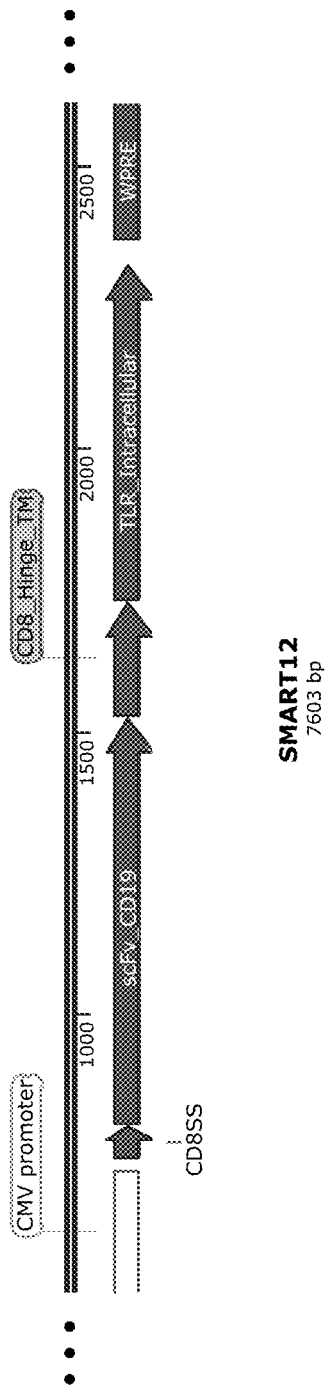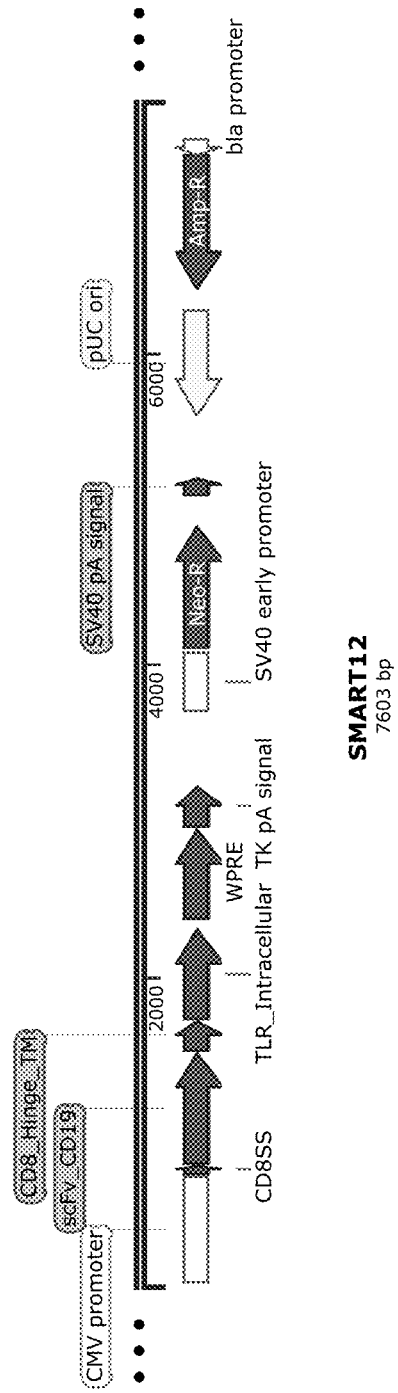
FIG. 3A
FIG. 3B

SEQUENCE LISTING

<160> NUMBER OF SEQ ID NOS: 34

<210> SEQ ID NO 1
<211> LENGTH: 113
<212> TYPE: PRT
<213> ORGANISM: Homo sapiens

<400> SEQUENCE: 1

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 2
<211> LENGTH: 113
<212> TYPE: PRT
<213> ORGANISM: Mus musculus

<400> SEQUENCE: 2

-continued

```
Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
            100                 105                 110

Arg
```

<210> SEQ ID NO 3
<211> LENGTH: 459
<212> TYPE: PRT
<213> ORGANISM: Artificial Sequence
<220> FEATURE:
<223> OTHER INFORMATION: Synthetic Construct

<400> SEQUENCE: 3

```
Leu Phe Thr Pro Val Val Ala Cys Met Ser Ile Met Ala Leu Leu
1               5                   10                  15

Leu Leu Leu Leu Leu Leu Leu Leu Tyr Lys Tyr Lys Gln Lys Pro Lys
            20                  25                  30

Tyr Gln Val Arg Trp Lys Ile Ile Glu Ser Tyr Glu Gly Asn Ser Tyr
        35                  40                  45

Thr Phe Ile Asp Pro Thr Gln Leu Pro Tyr Asn Glu Lys Trp Glu Phe
    50                  55                  60

Pro Arg Asn Asn Leu Gln Phe Gly Lys Thr Leu Gly Ala Gly Ala Phe
65                  70                  75                  80

Gly Lys Val Val Glu Ala Thr Ala Phe Gly Leu Gly Lys Glu Asp Ala
                85                  90                  95

Val Leu Lys Val Ala Val Lys Met Leu Lys Ser Thr Ala His Ala Asp
            100                 105                 110

Glu Lys Glu Ala Leu Met Ser Glu Leu Lys Ile Met Ser His Leu Gly
        115                 120                 125

Gln His Glu Asn Ile Val Asn Leu Leu Gly Ala Cys Thr His Gly Gly
    130                 135                 140

Pro Val Leu Val Ile Thr Glu Tyr Cys Cys Tyr Gly Asp Leu Leu Asn
145                 150                 155                 160

Phe Leu Arg Arg Lys Ala Glu Ala Met Leu Gly Pro Ser Leu Ser Pro
                165                 170                 175

Gly Gln Asp Pro Glu Gly Gly Val Asp Tyr Lys Asn Ile His Leu Glu
            180                 185                 190

Lys Lys Tyr Val Arg Arg Asp Ser Gly Phe Ser Ser Gln Gly Val Asp
        195                 200                 205

Thr Tyr Val Glu Met Arg Pro Val Ser Thr Ser Ser Asn Asp Ser Phe
    210                 215                 220

Ser Glu Gln Asp Leu Asp Lys Glu Asp Gly Arg Pro Leu Glu Leu Arg
225                 230                 235                 240

Asp Leu Leu His Phe Ser Ser Gln Val Ala Gln Gly Met Ala Phe Leu
```

245                 250                 255

Ala Ser Lys Asn Cys Ile His Arg Asp Val Ala Arg Asn Val Leu
            260                 265                 270

Leu Thr Asn Gly His Val Ala Lys Ile Gly Asp Phe Gly Leu Ala Arg
            275                 280                 285

Asp Ile Met Asn Asp Ser Asn Tyr Ile Val Lys Gly Asn Ala Arg Leu
        290                 295                 300

Pro Val Lys Trp Met Ala Pro Glu Ser Ile Phe Asp Cys Val Tyr Thr
305                 310                 315                 320

Val Gln Ser Asp Val Trp Ser Tyr Gly Ile Leu Leu Trp Glu Ile Phe
                325                 330                 335

Ser Leu Gly Leu Asn Pro Tyr Pro Gly Ile Leu Val Asn Ser Lys Phe
            340                 345                 350

Tyr Lys Leu Val Lys Asp Gly Tyr Gln Met Ala Gln Pro Ala Phe Ala
            355                 360                 365

Pro Lys Asn Ile Tyr Ser Ile Met Gln Ala Cys Trp Ala Leu Glu Pro
    370                 375                 380

Thr His Arg Pro Thr Phe Gln Gln Ile Cys Ser Phe Leu Gln Glu Gln
385                 390                 395                 400

Ala Gln Glu Asp Arg Arg Glu Arg Asp Tyr Thr Asn Leu Pro Ser Ser
                405                 410                 415

Ser Arg Ser Gly Gly Ser Gly Ser Ser Ser Glu Leu Glu Glu Glu
            420                 425                 430

Ser Ser Ser Glu His Leu Thr Cys Cys Glu Gln Gly Asp Ile Ala Gln
            435                 440                 445

Pro Leu Leu Gln Pro Asn Asn Tyr Gln Phe Cys
    450                 455

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Leu Phe Thr Pro Val Val Ala Cys Met Ser Ile Met Ala Leu Leu
1               5                   10                  15

Leu Leu Leu Leu Leu Leu Leu Tyr
            20                  25

<210> SEQ ID NO 5
<211> LENGTH: 434
<212> TYPE: PRT
<213> ORGANISM: Homo sapiens

<400> SEQUENCE: 5

Lys Tyr Lys Gln Lys Pro Lys Tyr Gln Val Arg Trp Lys Ile Ile Glu
1               5                   10                  15

Ser Tyr Glu Gly Asn Ser Tyr Thr Phe Ile Asp Pro Thr Gln Leu Pro
                20                  25                  30

Tyr Asn Glu Lys Trp Glu Phe Pro Arg Asn Asn Leu Gln Phe Gly Lys
            35                  40                  45

Thr Leu Gly Ala Gly Ala Phe Gly Lys Val Val Glu Ala Thr Ala Phe
        50                  55                  60

Gly Leu Gly Lys Glu Asp Ala Val Leu Lys Val Ala Val Lys Met Leu
65                  70                  75                  80

Lys Ser Thr Ala His Ala Asp Glu Lys Glu Ala Leu Met Ser Glu Leu
            85                  90                  95

Lys Ile Met Ser His Leu Gly Gln His Glu Asn Ile Val Asn Leu Leu
            100                 105                 110

Gly Ala Cys Thr His Gly Gly Pro Val Leu Val Ile Thr Glu Tyr Cys
            115                 120                 125

Cys Tyr Gly Asp Leu Leu Asn Phe Leu Arg Arg Lys Ala Glu Ala Met
130                 135                 140

Leu Gly Pro Ser Leu Ser Pro Gly Gln Asp Pro Glu Gly Gly Val Asp
145                 150                 155                 160

Tyr Lys Asn Ile His Leu Glu Lys Lys Tyr Val Arg Arg Asp Ser Gly
                165                 170                 175

Phe Ser Ser Gln Gly Val Asp Thr Tyr Val Glu Met Arg Pro Val Ser
            180                 185                 190

Thr Ser Ser Asn Asp Ser Phe Ser Glu Gln Asp Leu Asp Lys Glu Asp
            195                 200                 205

Gly Arg Pro Leu Glu Leu Arg Asp Leu Leu His Phe Ser Ser Gln Val
            210                 215                 220

Ala Gln Gly Met Ala Phe Leu Ala Ser Lys Asn Cys Ile His Arg Asp
225                 230                 235                 240

Val Ala Ala Arg Asn Val Leu Leu Thr Asn Gly His Val Ala Lys Ile
                245                 250                 255

Gly Asp Phe Gly Leu Ala Arg Asp Ile Met Asn Asp Ser Asn Tyr Ile
            260                 265                 270

Val Lys Gly Asn Ala Arg Leu Pro Val Lys Trp Met Ala Pro Glu Ser
            275                 280                 285

Ile Phe Asp Cys Val Tyr Thr Val Gln Ser Asp Val Trp Ser Tyr Gly
            290                 295                 300

Ile Leu Leu Trp Glu Ile Phe Ser Leu Gly Leu Asn Pro Tyr Pro Gly
305                 310                 315                 320

Ile Leu Val Asn Ser Lys Phe Tyr Lys Leu Val Lys Asp Gly Tyr Gln
                325                 330                 335

Met Ala Gln Pro Ala Phe Ala Pro Lys Asn Ile Tyr Ser Ile Met Gln
            340                 345                 350

Ala Cys Trp Ala Leu Glu Pro Thr His Arg Pro Thr Phe Gln Gln Ile
            355                 360                 365

Cys Ser Phe Leu Gln Glu Gln Ala Gln Glu Asp Arg Arg Glu Arg Asp
            370                 375                 380

Tyr Thr Asn Leu Pro Ser Ser Arg Ser Gly Ser Gly Ser Ser
385                 390                 395                 400

Ser Ser Glu Leu Glu Glu Ser Ser Glu His Leu Thr Cys Cys
            405                 410                 415

Glu Gln Gly Asp Ile Ala Gln Pro Leu Leu Gln Pro Asn Asn Tyr Gln
            420                 425                 430

Phe Cys

<210> SEQ ID NO 6
<211> LENGTH: 25
<212> TYPE: PRT
<213> ORGANISM: Artificial Sequence
<220> FEATURE:
<223> OTHER INFORMATION: Synthetic Construct

<400> SEQUENCE: 6

```
Leu Phe Thr Pro Val Val Ala Cys Met Ser Val Met Ser Leu Leu
1               5                   10                  15

Val Leu Leu Leu Leu Leu Leu Tyr
            20                  25
```

<210> SEQ ID NO 7
<211> LENGTH: 441
<212> TYPE: PRT
<213> ORGANISM: Mus musculus

<400> SEQUENCE: 7

```
Lys Tyr Lys Gln Lys Pro Lys Tyr Gln Val Arg Trp Lys Ile Ile Glu
1               5                   10                  15

Arg Tyr Glu Gly Asn Ser Tyr Thr Phe Ile Asp Pro Thr Gln Leu Pro
            20                  25                  30

Tyr Asn Glu Lys Trp Glu Phe Pro Arg Asn Asn Leu Gln Phe Gly Lys
        35                  40                  45

Thr Leu Gly Ala Gly Ala Phe Gly Lys Val Val Glu Ala Thr Ala Phe
    50                  55                  60

Gly Leu Gly Lys Glu Asp Ala Val Leu Lys Val Ala Val Lys Met Leu
65                  70                  75                  80

Lys Ser Thr Ala His Ala Asp Glu Lys Glu Ala Leu Met Ser Glu Leu
                85                  90                  95

Lys Ile Met Ser His Leu Gly Gln His Glu Asn Ile Val Asn Leu Leu
            100                 105                 110

Gly Ala Cys Thr His Gly Gly Pro Val Leu Val Ile Thr Glu Tyr Cys
        115                 120                 125

Cys Tyr Gly Asp Leu Leu Asn Phe Leu Arg Arg Lys Ala Glu Ala Met
    130                 135                 140

Leu Gly Pro Ser Leu Ser Pro Gly Gln Asp Ser Glu Gly Asp Ser Ser
145                 150                 155                 160

Tyr Lys Asn Ile His Leu Glu Lys Lys Tyr Val Arg Arg Asp Ser Gly
                165                 170                 175

Phe Ser Ser Gln Gly Val Asp Thr Tyr Val Glu Met Arg Pro Val Ser
            180                 185                 190

Thr Ser Ser Ser Asp Ser Phe Phe Lys Gln Asp Leu Asp Lys Glu Ala
        195                 200                 205

Ser Arg Pro Leu Glu Leu Trp Asp Leu Leu His Phe Ser Ser Gln Val
    210                 215                 220

Ala Gln Gly Met Ala Phe Leu Ala Ser Lys Asn Cys Ile His Arg Asp
225                 230                 235                 240

Val Ala Ala Arg Asn Val Leu Leu Thr Ser Gly His Val Ala Lys Ile
                245                 250                 255

Gly Asp Phe Gly Leu Ala Arg Asp Ile Met Asn Asp Ser Asn Tyr Val
            260                 265                 270

Val Lys Gly Asn Ala Arg Leu Pro Val Lys Trp Met Ala Pro Glu Ser
        275                 280                 285

Ile Phe Asp Cys Val Tyr Thr Val Gln Ser Asp Val Trp Ser Tyr Gly
    290                 295                 300

Ile Leu Leu Trp Glu Ile Phe Ser Leu Gly Leu Asn Pro Tyr Pro Gly
305                 310                 315                 320

Ile Leu Val Asn Asn Lys Phe Tyr Lys Leu Val Lys Asp Gly Tyr Gln
                325                 330                 335

Met Ala Gln Pro Val Phe Ala Pro Lys Asn Ile Tyr Ser Ile Met Gln
            340                 345                 350
```

```
Ser Cys Trp Asp Leu Glu Pro Thr Arg Arg Pro Thr Phe Gln Gln Ile
        355                 360                 365

Cys Phe Leu Leu Gln Glu Gln Ala Arg Leu Glu Arg Arg Asp Gln Asp
        370                 375                 380

Tyr Ala Asn Leu Pro Ser Ser Gly Gly Ser Ser Gly Ser Asp Ser Gly
385                 390                 395                 400

Gly Gly Ser Ser Gly Gly Ser Ser Ser Glu Pro Glu Glu Ser Ser
            405                 410                 415

Ser Glu His Leu Ala Cys Cys Glu Pro Gly Asp Ile Ala Gln Pro Leu
        420                 425                 430

Leu Gln Pro Asn Asn Tyr Gln Phe Cys
        435                 440

<210> SEQ ID NO 8
<211> LENGTH: 31
<212> TYPE: PRT
<213> ORGANISM: Artificial Sequence
<220> FEATURE:
<223> OTHER INFORMATION: Synthetic Construct

<400> SEQUENCE: 8

Asp Glu Glu Glu Val Leu Lys Ser Leu Lys Phe Ser Leu Phe Ile Val
1               5                   10                  15

Cys Thr Val Thr Leu Thr Leu Phe Leu Met Thr Ile Leu Thr Val
            20                  25                  30

<210> SEQ ID NO 9
<211> LENGTH: 198
<212> TYPE: PRT
<213> ORGANISM: Homo sapiens

<400> SEQUENCE: 9

Thr Lys Phe Arg Gly Phe Cys Phe Ile Cys Tyr Lys Thr Ala Gln Arg
1               5                   10                  15

Leu Val Phe Lys Asp His Pro Gln Gly Thr Glu Pro Asp Met Tyr Lys
            20                  25                  30

Tyr Asp Ala Tyr Leu Cys Phe Ser Ser Lys Asp Phe Thr Trp Val Gln
        35                  40                  45

Asn Ala Leu Leu Lys His Leu Asp Thr Gln Tyr Ser Asp Gln Asn Arg
    50                  55                  60

Phe Asn Leu Cys Phe Glu Glu Arg Asp Phe Val Pro Gly Glu Asn Arg
65                  70                  75                  80

Ile Ala Asn Ile Gln Asp Ala Ile Trp Asn Ser Arg Lys Ile Val Cys
                85                  90                  95

Leu Val Ser Arg His Phe Leu Arg Asp Gly Trp Cys Leu Glu Ala Phe
            100                 105                 110

Ser Tyr Ala Gln Gly Arg Cys Leu Ser Asp Leu Asn Ser Ala Leu Ile
        115                 120                 125

Met Val Val Val Gly Ser Leu Ser Gln Tyr Gln Leu Met Lys His Gln
    130                 135                 140

Ser Ile Arg Gly Phe Val Gln Lys Gln Gln Tyr Leu Arg Trp Pro Glu
145                 150                 155                 160

Asp Phe Gln Asp Val Gly Trp Phe Leu His Lys Leu Ser Gln Gln Ile
                165                 170                 175

Leu Lys Lys Glu Lys Glu Lys Lys Lys Asp Asn Asn Ile Pro Leu Gln
            180                 185                 190
```

Thr Val Ala Thr Ile Ser
        195

<210> SEQ ID NO 10
<211> LENGTH: 107
<212> TYPE: PRT
<213> ORGANISM: Homo sapiens

<400> SEQUENCE: 10

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 11
<211> LENGTH: 21
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic Construct

<400> SEQUENCE: 12

Gly Ser Thr Ser Gly Ser Gly Lys Pro Gly Ser Gly Glu Gly Ser Thr
1               5                   10                  15

Lys Gly

<210> SEQ ID NO 13
<211> LENGTH: 240
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

-continued

```
Tyr His Thr Ser Arg Leu His Ser Gly Val Pro Ser Arg Phe Ser Gly
         50                  55                  60
Ser Gly Ser Gly Thr Asp Tyr Ser Leu Thr Ile Ser Asn Leu Glu Gln
 65                  70                  75                  80
Glu Asp Ile Ala Thr Tyr Phe Cys Gln Gln Gly Asn Thr Leu Pro Tyr
                 85                  90                  95
Thr Phe Gly Gly Gly Thr Lys Leu Glu Ile Thr Gly Gly Gly Gly Ser
             100                 105                 110
Gly Gly Gly Gly Ser Gly Gly Gly Ser Glu Val Lys Leu Gln Glu
         115                 120                 125
Ser Gly Pro Gly Leu Val Ala Pro Ser Gln Ser Leu Ser Val Thr Cys
130                 135                 140
Thr Val Ser Gly Val Ser Leu Pro Asp Tyr Gly Val Ser Trp Ile Arg
145                 150                 155                 160
Gln Pro Pro Arg Lys Gly Leu Glu Trp Leu Gly Val Ile Trp Gly Ser
                165                 170                 175
Glu Thr Thr Tyr Tyr Asn Ser Ala Leu Lys Ser Arg Leu Thr Ile Ile
            180                 185                 190
Lys Asp Asn Ser Lys Ser Gln Val Phe Leu Lys Met Asn Ser Leu Gln
        195                 200                 205
Thr Asp Asp Thr Ala Ile Tyr Tyr Cys Ala Lys His Tyr Tyr Gly
    210                 215                 220
Gly Ser Tyr Ala Met Asp Tyr Trp Gly Gln Gly Thr Ser Val Thr Val
225                 230                 235                 240
```

<210> SEQ ID NO 14
<211> LENGTH: 47
<212> TYPE: PRT
<213> ORGANISM: Homo sapiens

<400> SEQUENCE: 14

```
Thr Thr Thr Pro Ala Pro Arg Pro Pro Thr Pro Ala Pro Thr Ile Ala
 1               5                  10                  15
Ser Gln Pro Leu Ser Leu Arg Pro Glu Ala Cys Arg Pro Ala Ala Gly
             20                  25                  30
Gly Ala Val His Thr Arg Gly Leu Asp Phe Ala Cys Asp Ile Tyr
         35                  40                  45
```

<210> SEQ ID NO 15
<211> LENGTH: 22
<212> TYPE: PRT
<213> ORGANISM: Homo sapiens

<400> SEQUENCE: 15

```
Ile Trp Ala Pro Leu Ala Gly Thr Cys Gly Val Leu Leu Leu Ser Leu
 1               5                  10                  15
Val Ile Thr Leu Tyr Cys
             20
```

<210> SEQ ID NO 16
<211> LENGTH: 42
<212> TYPE: PRT
<213> ORGANISM: Homo sapiens

<400> SEQUENCE: 16

```
Lys Arg Gly Arg Lys Lys Leu Leu Tyr Ile Phe Lys Gln Pro Phe Met
 1               5                  10                  15
```

```
Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 17
<211> LENGTH: 92
<212> TYPE: PRT
<213> ORGANISM: Homo sapiens

<400> SEQUENCE: 17

Leu Arg Pro Val Gln Ala Gln Ala Gln Ser Asp Cys Ser Cys Ser Thr
1               5                   10                  15

Val Ser Pro Gly Val Leu Ala Gly Ile Val Met Gly Asp Leu Val Leu
            20                  25                  30

Thr Val Leu Ile Ala Leu Ala Val Tyr Phe Leu Gly Arg Leu Val Pro
            35                  40                  45

Arg Gly Arg Gly Ala Ala Glu Ala Ala Thr Arg Lys Gln Arg Ile Thr
        50                  55                  60

Glu Thr Glu Ser Pro Tyr Gln Glu Leu Gln Gly Gln Arg Ser Asp Val
65                  70                  75                  80

Tyr Ser Asp Leu Asn Thr Gln Arg Pro Tyr Tyr Lys
                85                  90

<210> SEQ ID NO 18
<211> LENGTH: 218
<212> TYPE: PRT
<213> ORGANISM: Artificial Sequence
<220> FEATURE:
<223> OTHER INFORMATION: Synthetic Construct

<400> SEQUENCE: 18

Ser Arg Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
            20                  25                  30

Glu Asp Gly Lys Lys Phe Asp Ser Ser Arg Asp Arg Asn Lys Pro Phe
            35                  40                  45

Lys Phe Met Leu Gly Lys Gln Glu Val Ile Arg Gly Trp Glu Glu Gly
        50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu Thr Arg Gly
            100                 105                 110

Val Gln Val Glu Thr Ile Ser Pro Gly Asp Gly Arg Thr Phe Pro Lys
            115                 120                 125

Arg Gly Gln Thr Cys Val Val His Tyr Thr Gly Met Leu Glu Asp Gly
        130                 135                 140

Lys Lys Phe Asp Ser Ser Arg Asp Arg Asn Lys Pro Phe Lys Phe Met
145                 150                 155                 160

Leu Gly Lys Gln Glu Val Ile Arg Gly Trp Glu Glu Gly Val Ala Gln
                165                 170                 175

Met Ser Val Gly Gln Arg Ala Lys Leu Thr Ile Ser Pro Asp Tyr Ala
            180                 185                 190

Tyr Gly Ala Thr Gly His Pro Gly Ile Ile Pro Pro His Ala Thr Leu
```

```
                    195                 200                 205

Val Phe Asp Val Glu Leu Leu Lys Leu Glu
    210                 215

<210> SEQ ID NO 19
<211> LENGTH: 96
<212> TYPE: PRT
<213> ORGANISM: Artificial Sequence
<220> FEATURE:
<223> OTHER INFORMATION: Synthetic Construct

<400> SEQUENCE: 19

Ser Arg Ile Leu Trp His Glu Met Trp His Glu Gly Leu Glu Ala
1               5                   10                  15

Ser Arg Leu Tyr Phe Gly Glu Arg Asn Val Lys Gly Met Phe Glu Val
            20                  25                  30

Leu Glu Pro Leu His Ala Met Met Glu Arg Gly Pro Gln Thr Leu Lys
        35                  40                  45

Glu Thr Ser Phe Asn Gln Ala Tyr Gly Arg Asp Leu Met Glu Ala Gln
    50                  55                  60

Glu Trp Cys Arg Lys Tyr Met Lys Ser Gly Asn Val Lys Asp Leu Leu
65                  70                  75                  80

Gln Ala Trp Asp Leu Tyr Tyr His Val Phe Arg Arg Ile Ser Lys Thr
                85                  90                  95

<210> SEQ ID NO 20
<211> LENGTH: 485
<212> TYPE: PRT
<213> ORGANISM: Artificial Sequence
<220> FEATURE:
<223> OTHER INFORMATION: Synthetic Construct

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190
```

```
Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
    210                 215                 220

Met Asn Ser Leu Gln Thr Asp Thr Ala Ile Tyr Tyr Cys Ala Lys
225                 230                 235                 240

His Tyr Tyr Tyr Gly Ser Tyr Ala Met Asp Tyr Trp Gly Gln Gly
            245                 250                 255

Thr Ser Val Thr Val Thr Thr Thr Pro Ala Pro Arg Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
            325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
    355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
            405                 410                 415

Met Gly Gly Lys Pro Gln Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 21
<211> LENGTH: 550
<212> TYPE: PRT
<213> ORGANISM: Artificial Sequence
<220> FEATURE:
<223> OTHER INFORMATION: Synthetic Construct

<400> SEQUENCE: 21

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60
```

```
Val Lys Leu Leu Ile Tyr His Thr Ser Arg Leu His Ser Gly Val Pro
 65                  70                  75                  80

Ser Arg Phe Ser Gly Ser Gly Ser Gly Thr Asp Tyr Ser Leu Thr Ile
                 85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
                115                 120                 125

Gly Gly Gly Gly Ser Gly Gly Gly Ser Gly Gly Gly Gly Ser Glu
                130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
                195                 200                 205

Arg Leu Thr Ile Ile Lys Asp Asn Ser Lys Ser Gln Val Phe Leu Lys
                210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Thr Thr Thr Pro Ala Pro Arg Pro Pro Thr Pro
                260                 265                 270

Ala Pro Thr Ile Ala Ser Gln Pro Leu Ser Leu Arg Pro Glu Ala Cys
                275                 280                 285

Arg Pro Ala Ala Gly Gly Ala Val His Thr Arg Gly Leu Asp Phe Ala
                290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Ile Glu Val Met Tyr Pro
                325                 330                 335

Pro Pro Tyr Leu Asp Asn Glu Lys Ser Asn Gly Thr Ile Ile His Val
                340                 345                 350

Lys Gly Lys His Leu Cys Pro Ser Pro Leu Phe Pro Gly Pro Ser Lys
                355                 360                 365

Pro Phe Trp Val Leu Val Val Val Gly Gly Val Leu Ala Cys Tyr Ser
                370                 375                 380

Leu Leu Val Thr Val Ala Phe Ile Ile Phe Trp Val Arg Ser Lys Arg
385                 390                 395                 400

Ser Arg Leu Leu His Ser Asp Tyr Met Asn Met Thr Pro Arg Arg Pro
                405                 410                 415

Gly Pro Thr Arg Lys His Tyr Gln Pro Tyr Ala Pro Pro Arg Asp Phe
                420                 425                 430

Ala Ala Tyr Arg Ser Arg Val Lys Phe Ser Arg Ser Ala Asp Ala Pro
                435                 440                 445

Ala Tyr Gln Gln Gly Gln Asn Gln Leu Tyr Asn Glu Leu Asn Leu Gly
                450                 455                 460

Arg Arg Glu Glu Tyr Asp Val Leu Asp Lys Arg Arg Gly Arg Asp Pro
465                 470                 475                 480

Glu Met Gly Gly Lys Pro Gln Arg Arg Lys Asn Pro Gln Glu Gly Leu
```

485                 490                 495
Tyr Asn Glu Leu Gln Lys Asp Lys Met Ala Glu Ala Tyr Ser Glu Ile
                500                 505                 510

Gly Met Lys Gly Glu Arg Arg Gly Lys Gly His Asp Gly Leu Tyr
                515                 520                 525

Gln Gly Leu Ser Thr Ala Thr Lys Asp Thr Tyr Asp Ala Leu His Met
530                 535                 540

Gln Ala Leu Pro Pro Arg
545                 550

<210> SEQ ID NO 22
<211> LENGTH: 528
<212> TYPE: PRT
<213> ORGANISM: Artificial Sequence
<220> FEATURE:
<223> OTHER INFORMATION: Synthetic Construct

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
        130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Thr Thr Thr Pro Ala Pro Arg Pro Pro Thr Pro
                260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala

```
                290                 295                 300
Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Thr Lys Phe Arg Gly Phe
                325                 330                 335

Cys Phe Ile Cys Tyr Lys Thr Ala Gln Arg Leu Val Phe Lys Asp His
                340                 345                 350

Pro Gln Gly Thr Glu Pro Asp Met Tyr Lys Tyr Asp Ala Tyr Leu Cys
                355                 360                 365

Phe Ser Ser Lys Asp Phe Thr Trp Val Gln Asn Ala Leu Leu Lys His
370                 375                 380

Leu Asp Thr Gln Tyr Ser Asp Gln Asn Arg Phe Asn Leu Cys Phe Glu
385                 390                 395                 400

Glu Arg Asp Phe Val Pro Gly Glu Asn Arg Ile Ala Asn Ile Gln Asp
                405                 410                 415

Ala Ile Trp Asn Ser Arg Lys Ile Val Cys Leu Val Ser Arg His Phe
                420                 425                 430

Leu Arg Asp Gly Trp Cys Leu Glu Ala Phe Ser Tyr Ala Gln Gly Arg
                435                 440                 445

Cys Leu Ser Asp Leu Asn Ser Ala Leu Ile Met Val Val Val Gly Ser
                450                 455                 460

Leu Ser Gln Tyr Gln Leu Met Lys His Gln Ser Ile Arg Gly Phe Val
465                 470                 475                 480

Gln Lys Gln Gln Tyr Leu Arg Trp Pro Glu Asp Phe Gln Asp Val Gly
                485                 490                 495

Trp Phe Leu His Lys Leu Ser Gln Gln Ile Leu Lys Lys Glu Lys Glu
                500                 505                 510

Lys Lys Lys Asp Asn Asn Ile Pro Leu Gln Thr Val Ala Thr Ile Ser
                515                 520                 525

<210> SEQ ID NO 23
<211> LENGTH: 490
<212> TYPE: PRT
<213> ORGANISM: Artificial Sequence
<220> FEATURE:
<223> OTHER INFORMATION: Synthetic Construct

<400> SEQUENCE: 23

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
                35                  40                  45

Asp Ile Ser Lys Tyr Leu Asn Trp Tyr Gln Gln Lys Pro Asp Gly Thr
50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
                115                 120                 125

Gly Gly Gly Gly Ser Gly Gly Gly Gly Ser Gly Gly Gly Gly Ser Glu
```

```
            130                 135                 140
Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Asp Glu Glu Val Leu Lys Ser Leu Lys Phe
                260                 265                 270

Ser Leu Phe Ile Val Cys Thr Val Thr Leu Thr Leu Phe Leu Met Thr
        275                 280                 285

Ile Leu Thr Val Thr Lys Phe Arg Gly Phe Cys Phe Ile Cys Tyr Lys
    290                 295                 300

Thr Ala Gln Arg Leu Val Phe Lys Asp His Pro Gln Gly Thr Glu Pro
305                 310                 315                 320

Asp Met Tyr Lys Tyr Asp Ala Tyr Leu Cys Phe Ser Ser Lys Asp Phe
                325                 330                 335

Thr Trp Val Gln Asn Ala Leu Leu Lys His Leu Asp Thr Gln Tyr Ser
            340                 345                 350

Asp Gln Asn Arg Phe Asn Leu Cys Phe Glu Glu Arg Asp Phe Val Pro
        355                 360                 365

Gly Glu Asn Arg Ile Ala Asn Ile Gln Asp Ala Ile Trp Asn Ser Arg
    370                 375                 380

Lys Ile Val Cys Leu Val Ser Arg His Phe Leu Arg Asp Gly Trp Cys
385                 390                 395                 400

Leu Glu Ala Phe Ser Tyr Ala Gln Gly Arg Cys Leu Ser Asp Leu Asn
                405                 410                 415

Ser Ala Leu Ile Met Val Val Gly Ser Leu Ser Gln Tyr Gln Leu
            420                 425                 430

Met Lys His Gln Ser Ile Arg Gly Phe Val Gln Lys Gln Gln Tyr Leu
        435                 440                 445

Arg Trp Pro Glu Asp Phe Gln Asp Val Gly Trp Phe Leu His Lys Leu
    450                 455                 460

Ser Gln Gln Ile Leu Lys Lys Glu Lys Glu Lys Lys Lys Asp Asn Asn
465                 470                 475                 480

Ile Pro Leu Gln Thr Val Ala Thr Ile Ser
                485                 490

<210> SEQ ID NO 24
<211> LENGTH: 635
<212> TYPE: PRT
<213> ORGANISM: Artificial Sequence
<220> FEATURE:
<223> OTHER INFORMATION: Synthetic Construct

<400> SEQUENCE: 24

Met Ala Leu Pro Val Thr Ala Leu Leu Leu Pro Leu Ala Leu Leu Leu
```

-continued

```
1               5                   10                  15
His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Ile Glu Val Met Tyr Pro
                325                 330                 335

Pro Pro Tyr Leu Asp Asn Glu Lys Ser Asn Gly Thr Ile Ile His Val
            340                 345                 350

Lys Gly Lys His Leu Cys Pro Ser Pro Leu Phe Pro Gly Pro Ser Lys
            355                 360                 365

Pro Phe Trp Val Leu Val Val Gly Gly Val Leu Ala Cys Tyr Ser
    370                 375                 380

Leu Leu Val Thr Val Ala Phe Ile Ile Phe Trp Val Arg Ser Lys Arg
385                 390                 395                 400

Ser Arg Leu Leu His Ser Asp Tyr Met Asn Met Thr Pro Arg Arg Pro
                405                 410                 415

Gly Pro Thr Arg Lys His Tyr Gln Pro Tyr Ala Pro Pro Arg Asp Phe
            420                 425                 430
```

Ala Ala Tyr Arg Ser Thr Lys Phe Arg Gly Phe Cys Phe Ile Cys Tyr
            435                 440                 445

Lys Thr Ala Gln Arg Leu Val Phe Lys Asp His Pro Gln Gly Thr Glu
450                 455                 460

Pro Asp Met Tyr Lys Tyr Asp Ala Tyr Leu Cys Phe Ser Ser Lys Asp
465                 470                 475                 480

Phe Thr Trp Val Gln Asn Ala Leu Leu Lys His Leu Asp Thr Gln Tyr
                485                 490                 495

Ser Asp Gln Asn Arg Phe Asn Leu Cys Phe Glu Arg Asp Phe Val
            500                 505                 510

Pro Gly Glu Asn Arg Ile Ala Asn Ile Gln Asp Ala Ile Trp Asn Ser
            515                 520                 525

Arg Lys Ile Val Cys Leu Val Ser Arg His Phe Leu Arg Asp Gly Trp
530                 535                 540

Cys Leu Glu Ala Phe Ser Tyr Ala Gln Gly Arg Cys Leu Ser Asp Leu
545                 550                 555                 560

Asn Ser Ala Leu Ile Met Val Val Gly Ser Leu Ser Gln Tyr Gln
                565                 570                 575

Leu Met Lys His Gln Ser Ile Arg Gly Phe Val Gln Lys Gln Tyr
            580                 585                 590

Leu Arg Trp Pro Glu Asp Phe Gln Asp Val Gly Trp Phe Leu His Lys
            595                 600                 605

Leu Ser Gln Gln Ile Leu Lys Lys Glu Lys Lys Lys Asp Asn
            610                 615                 620

Asn Ile Pro Leu Gln Thr Val Ala Thr Ile Ser
625                 630                 635

<210> SEQ ID NO 25
<211> LENGTH: 570
<212> TYPE: PRT
<213> ORGANISM: Artificial Sequence
<220> FEATURE:
<223> OTHER INFORMATION: Synthetic Construct

<400> SEQUENCE: 25

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

```
Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Thr Lys Phe Arg Gly Phe Cys Phe Ile Cys Tyr Lys
    370                 375                 380

Thr Ala Gln Arg Leu Val Phe Lys Asp His Pro Gln Gly Thr Glu Pro
385                 390                 395                 400

Asp Met Tyr Lys Tyr Asp Ala Tyr Leu Cys Phe Ser Ser Lys Asp Phe
                405                 410                 415

Thr Trp Val Gln Asn Ala Leu Leu Lys His Leu Asp Thr Gln Tyr Ser
            420                 425                 430

Asp Gln Asn Arg Phe Asn Leu Cys Phe Glu Glu Arg Asp Phe Val Pro
        435                 440                 445

Gly Glu Asn Arg Ile Ala Asn Ile Gln Asp Ala Ile Trp Asn Ser Arg
    450                 455                 460

Lys Ile Val Cys Leu Val Ser Arg His Phe Leu Arg Asp Gly Trp Cys
465                 470                 475                 480

Leu Glu Ala Phe Ser Tyr Ala Gln Gly Arg Cys Leu Ser Asp Leu Asn
                485                 490                 495

Ser Ala Leu Ile Met Val Val Gly Ser Leu Ser Gln Tyr Gln Leu
            500                 505                 510

Met Lys His Gln Ser Ile Arg Gly Phe Val Gln Lys Gln Gln Tyr Leu
        515                 520                 525

Arg Trp Pro Glu Asp Phe Gln Asp Val Gly Trp Phe Leu His Lys Leu
    530                 535                 540

Ser Gln Gln Ile Leu Lys Lys Glu Lys Glu Lys Lys Asp Asn Asn
545                 550                 555                 560

Ile Pro Leu Gln Thr Val Ala Thr Ile Ser
                565                 570
```

<210> SEQ ID NO 26
<211> LENGTH: 603
<212> TYPE: PRT
<213> ORGANISM: Artificial Sequence
<220> FEATURE:
<223> OTHER INFORMATION: Synthetic Construct

<400> SEQUENCE: 26

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Asp Glu Glu Val Leu Lys Ser Leu Lys Phe
            260                 265                 270

Ser Leu Phe Ile Val Cys Thr Val Thr Leu Thr Leu Phe Leu Met Thr
        275                 280                 285

Ile Leu Thr Val Thr Lys Phe Arg Gly Phe Cys Phe Ile Cys Tyr Lys
    290                 295                 300

Thr Ala Gln Arg Leu Val Phe Lys Asp His Pro Gln Gly Thr Glu Pro
305                 310                 315                 320

Asp Met Tyr Lys Tyr Asp Ala Tyr Leu Cys Phe Ser Ser Lys Asp Phe
                325                 330                 335

Thr Trp Val Gln Asn Ala Leu Leu Lys His Leu Asp Thr Gln Tyr Ser
            340                 345                 350

Asp Gln Asn Arg Phe Asn Leu Cys Phe Glu Glu Arg Asp Phe Val Pro
        355                 360                 365
```

```
Gly Glu Asn Arg Ile Ala Asn Ile Gln Asp Ala Ile Trp Asn Ser Arg
    370                 375                 380
Lys Ile Val Cys Leu Val Ser Arg His Phe Leu Arg Asp Gly Trp Cys
385                 390                 395                 400
Leu Glu Ala Phe Ser Tyr Ala Gln Gly Arg Cys Leu Ser Asp Leu Asn
                405                 410                 415
Ser Ala Leu Ile Met Val Val Gly Ser Leu Ser Gln Tyr Gln Leu
            420                 425                 430
Met Lys His Gln Ser Ile Arg Gly Phe Val Gln Lys Gln Tyr Leu
            435                 440                 445
Arg Trp Pro Glu Asp Phe Gln Asp Val Gly Trp Phe Leu His Lys Leu
    450                 455                 460
Ser Gln Gln Ile Leu Lys Lys Glu Lys Lys Lys Asp Asn Asn
465                 470                 475                 480
Ile Pro Leu Gln Thr Val Ala Thr Ile Ser Arg Val Lys Phe Ser Arg
                485                 490                 495
Ser Ala Asp Ala Pro Ala Tyr Gln Gln Gly Gln Asn Gln Leu Tyr Asn
            500                 505                 510
Glu Leu Asn Leu Gly Arg Arg Glu Glu Tyr Asp Val Leu Asp Lys Arg
    515                 520                 525
Arg Gly Arg Asp Pro Glu Met Gly Gly Lys Pro Gln Arg Arg Lys Asn
    530                 535                 540
Pro Gln Glu Gly Leu Tyr Asn Glu Leu Gln Lys Asp Lys Met Ala Glu
545                 550                 555                 560
Ala Tyr Ser Glu Ile Gly Met Lys Gly Glu Arg Arg Arg Gly Lys Gly
                565                 570                 575
His Asp Gly Leu Tyr Gln Gly Leu Ser Thr Ala Thr Lys Asp Thr Tyr
            580                 585                 590
Asp Ala Leu His Met Gln Ala Leu Pro Pro Arg
            595                 600

<210> SEQ ID NO 27
<211> LENGTH: 1458
<212> TYPE: DNA
<213> ORGANISM: Artificial Sequence
<220> FEATURE:
<223> OTHER INFORMATION: Synthetic Construct

<400> SEQUENCE: 27
atggctctgc ctgtgacagc tctgctgctg cctctggccc tgctgctgca tgccgccaga      60
cccgatatcc agatgaccca gaccaccagc agcctgagcg ccagcctggg cgatagagtg     120
accatcagct gcagagccag ccaggacatc agcaagtacc tgaactggta tcagcagaaa     180
cccgacggca ccgtgaagct gctgatctac cacaccagca gactgcacag cggcgtgccc     240
agcagatttt ctggcagcgg ctccggcacc gactacagcc tgaccatctc caacctggaa     300
caggaagata tcgctaccta cttctgtcag caaggcaaca ccctgcccta ccttcggc      360 ggaggcacca agctggaaat cacaggcggc ggaggatctg gcggaggcgg aagtggcgga     420
gggggatctg aagtgaaact gcaggaaagc ggccctggcc tggtggcccc catctcagtct     480 ctgagcgtga cctgtaccgt gtccggcgtg tccctgcctg actatggcgt gtcctggatc     540
agacagcccc ccagaaaggg cctggaatgg ctgggagtga tctggggcag cgagacaacc     600
tactacaaca gcgccctgaa gtcccggctg accatcatca aggacaactc caagagccag     660
gtgttcctga agatgaacag cctgcagacc gacgacaccg ccatctacta ctgcgccaag     720
```

```
cactactact acggcggcag ctacgccatg gactactggg gccagggcac cagcgtgacc      780
gtgacaacaa caccegeccc tagacctcca accectgecc caacaatcgc cagecagect      840 ctgtctctga ggcccgaggc ttgtagacca gctgctggcg gagccgtgca caccagagga      900
ctggatttcg cctgcgacat ctacatctgg gcccctctgg ccggcacatg tggcgtgctg      960
ctgctgagcc tcgtgatcac cctgtactgc aagcggggca gaaagaaact gctgtacatc     1020
tttaagcagc ccttcatgcg gcccgtgcag accacccagg aagaggacgg ctgctcctgc     1080
agattccccg aggaagaaga aggcggctgc gagctgagag tgaagttcag cagatccgcc     1140
gacgcccctg cctaccagca gggacagaac cagctgtaca cgagctgaa cctgggcaga      1200 cgggaagagt acgacgtgct ggacaagcgg agaggccggg atcctgaaat gggcggcaag     1260
ccccagcgga aagaacccc tcaggaaggc ctgtataacg aactgcagaa agacaagatg      1320
gccgaggcct acagcgagat cggaatgaag ggcgagcgga aagaggcaa gggccacgat      1380 ggcctgtacc agggcctgag caccgccacc aaggacacct atgacgccct gcacatgcag     1440
gccctgcccc ctagataa                                                    1458

<210> SEQ ID NO 28
<211> LENGTH: 1653
<212> TYPE: DNA
<213> ORGANISM: Artificial Sequence
<220> FEATURE:
<223> OTHER INFORMATION: Synthetic Construct

<400> SEQUENCE: 28
atggctctgc ctgtgacagc tctgctgctg cctctggccc tgctgctgca tgccgccaga       60
cccgatatcc agatgaccca gaccaccagc agcctgagcg ccagcctggg cgatagagtg      120
accatcagct gcagagccag ccaggacatc agcaagtacc tgaactggta tcagcagaaa      180
cccgacggca ccgtgaagct gctgatctac cacaccagca gactgcacag cggcgtgccc      240
agcagatttt ctggcagcgg ctccggcacc gactacagcc tgaccatctc caacctggaa      300
caggaagata tcgctaccta cttctgtcag caaggcaaca ccctgcccta caccttcggc      360
ggaggcacca gctggaaaat cacaggcggc ggaggatctg gcggaggcgg aagtggcgga      420
gggggatctg aagtgaaact gcaggaaagc ggccctggcc tggtggcccc atctcagtct      480
ctgagcgtga cctgtaccgt gtccggcgtg tccctgcctg actatggcgt gtcctggatc      540
agacagcccc cagaaaggg cctggaatgg ctgggagtga tctggggcag cgagacaacc      600
tactacaaca gcgccctgaa gtccggctg accatcatca aggacaactc caagagccag      660
gtgttcctga agatgaacag cctgcagacc gacgacaccg ccatctacta ctgcgccaag      720
cactactact acggcggcag ctacgccatg gactactggg gccagggcac cagcgtgacc      780
gtgacaacaa caccegeccc tagacctcca accectgecc caacaatcgc cagecagect      840 ctgtctctga ggcccgaggc ttgtagacca gctgctggcg gagccgtgca caccagagga      900
ctggatttcg cctgcgacat ctacatctgg gcccctctgg ccggcacatg tggcgtgctg      960
ctgctgagcc tcgtgatcac cctgtactgc atcgaagtga tgtacccccc tccctacctg     1020
gacaacgaga agtccaacgg caccatcatc acgtgaagg caagcacct gtgccccagc       1080 cctctgtttc ctggccctag caagccettc tgggtgctgg tggtcgtggg cggagtgctg     1140
gcctgttata gcctgctcgt gacagtggcc ttcatcatct tttgggtgcg cagcaagcgg     1200
agccggctgc tgcactccga ctacatgaac atgacccca gacggccagg ccccacccgg      1260
aaacactatc agccttacgc ccctcccaga gacttcgccg cctaccggtc cagagtgaag     1320
```

```
ttcagcagat ccgccgacgc ccctgcctac cagcagggac agaaccagct gtacaacgag    1380
ctgaacctgg gcagacggga agagtacgac gtgctggaca gcggagagg ccgggatcct    1440 gaaatgggcg gcaagcccca gcggagaaag aaccctcagg aaggcctgta taacgaactg    1500
cagaaagaca gatggccga ggcctacagc gagatcggc tgaagggcga gcggagaaga    1560
ggcaagggcc acgatggcct gtaccagggc ctgagcaccg ccaccaagga cacctatgac    1620
gccctgcaca tgcaggccct gccccctaga taa                                1653
```

<210> SEQ ID NO 29
<211> LENGTH: 1587
<212> TYPE: DNA
<213> ORGANISM: Artificial Sequence
<220> FEATURE:
<223> OTHER INFORMATION: Synthetic Construct

<400> SEQUENCE: 29

```
atggctctgc ctgtgacagc tctgctgctg cctctggccc tgctgctgca tgccgccaga     60
cccgatatcc agatgaccca gaccaccagc agcctgagcg ccagcctggg cgatagagtg    120
accatcagct gcagagccag ccaggacatc agcaagtacc tgaactggta tcagcagaaa    180
cccgacggca ccgtgaagct gctgatctac cacaccagca gactgcacag cggcgtgccc    240
agcagatttt ctggcagcgg ctccggcacc gactacagcc tgaccatctc caacctggaa    300
caggaagata tcgctaccta cttctgtcag caaggcaaca ccctgcccta caccttcggc    360
ggaggcacca gctggaaat acaggcggc ggaggatctg gcggaggcgg aagtggcgga    420
gggggatctg aagtgaaact gcaggaaagc ggccctggcc tggtggcccc atctcagtct    480
ctgagcgtga cctgtaccgt gtccggcgtg tccctgcctg actatggcgt gtcctggatc    540
agacagcccc ccagaaaggg cctggaatgg ctgggagtga tctggggcag cgagacaacc    600
tactacaaca gcgccctgaa gtcccggctg accatcatca aggacaactc caagagccag    660
gtgttcctga agatgaacag cctgcagacc gacgacaccg ccatctacta ctgcgccaag    720
cactactact acggcggcag ctacgccatg gactactggg gccagggcac cagcgtgacc    780
gtgacaacaa cacccgcccc tagacctcca acccctgccc caacaatcgc cagccagcct    840
ctgtctctga gccccgaggc ttgtagacca gctgctggcg gagccgtgca caccagagga    900
ctggatttcg cctgcgacat ctacatctgg gcccctctgg ccggcacatg tggcgtgctg    960
ctgctgagcc tcgtgatcac cctgtactgt accaagttcc ggggcttctg cttcatctgc   1020
tacaagaccc ccagcggct ggtgttcaag gaccaccctc agggcaccga gcccgacatg   1080
tataagtacg acgcctacct gtgcttcagc agcaaggact tcacctgggt gcagaacgcc   1140
ctgctgaaac cctggacac ccagtacagc gaccagaaca gattcaacct gtgtttcgag   1200
gaacgggact tcgtgcccgg cgagaaccgg atcgccaaca tccaggacgc catctggaac   1260
agccggaaga tctgtgcct ggtgtcccgg cacttcctga gatgggctg gtgcctggaa   1320 gcctttagct acgcccaggg cagatgcctg agcgacctga actccgccct gatcatggtg   1380
gtcgtgggca gcctgtccca gtaccagctg atgaagcacc agagcatcag aggcttcgtg   1440
cagaagcagc agtacctgcg gtgggcccgag gacttccagg atgtgggctg gttcctgcac   1500
aagctgagcc agcagatcct gaagaaagaa aagagaagaa gaaggacaa caatatcccc   1560 ctgcagacag tggccacaat cagctga                                        1587
```

<210> SEQ ID NO 30

```
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 30
atggctctgc ctgtgacagc tctgctgctg cctctggccc tgctgctgca tgccgccaga    60
cccgatatcc agatgaccca gaccaccagc agcctgagcg ccagcctggg cgatagagtg   120
accatcagct gcagagccag ccaggacatc agcaagtacc tgaactggta tcagcagaaa   180
cccgacggca ccgtgaagct gctgatctac cacaccagca gactgcacag cggcgtgccc   240
agcagatttt ctggcagcgg ctccggcacc gactacagcc tgaccatctc caacctggaa   300
caggaagata tcgctaccta cttctgtcag caaggcaaca ccctgcccta caccttcggc   360
ggaggcacca agctggaaat cacaggcggc ggaggatctg gcggaggcgg aagtggcgga   420
gggggatctg aagtgaaact gcaggaaagc ggccctggcc tggtggcccc atctcagtct   480
ctgagcgtga cctgtaccgt gtccggcgtg tccctgcctg actatggcgt gtcctggatc   540
agacagcccc cagaaaaggg cctggaatgg ctgggagtga tctggggcag cgagacaacc   600
tactacaaca gcgccctgaa gtcccggctg accatcatca ggacaactc caagagccag   660
gtgttcctga agatgaacag cctgcagacc gacgacaccg ccatctacta ctgcgccaag   720
cactactact acggcggcag ctacgccatg gactactggg gccagggcac cagcgtgacc   780
gtggatgagg aagaggtgct gaagtctctg aagttcagcc tgttcatcgt gtgcaccgtg   840
accctgaccc tgttcctgat gaccatcctg accgtgacca agttccgggg cttctgcttc   900
atctgctaca agaccgccca gcggctggtg ttcaaggacc accctcaggg caccgagccc   960
gacatgtata gtacgacgc ctacctgtgc ttcagcagca aggacttcac ctgggtgcag  1020
aacgccctgc tgaaacacct ggacacccag tacagcgacc agaacagatt caacctgtgt  1080
ttcgaggaac gggacttcgt gcccggcgag aaccggatcg ccaacatcca ggacgccatc  1140
tggaacagcc ggaagatcgt gtgcctggtg tcccggcact tcctgagaga tggctggtgc  1200
ctggaagcct tagctacgc ccagggcaga tgcctgagcg acctgaactc cgccctgatc  1260
atggtggtcg tgggcagcct gtcccagtac cagctgatga agcaccagag catcagaggc  1320
ttcgtgcaga agcagcagta cctgcggtgg ccgaggact ccaggatgt gggctggttc  1380
ctgcacaagc tgagccagca gatcctgaag aaagaaaaag agaagaagaa ggacaacaac  1440
atcccctgc agacagtggc cacaatcagc tga                                1473

<210> SEQ ID NO 31
<211> LENGTH: 1908
<212> TYPE: DNA
<213> ORGANISM: Artificial Sequence
<220> FEATURE:
<223> OTHER INFORMATION: Synthetic Construct

<400> SEQUENCE: 31
atggccctgc ctgtgacagc tctgctgctg cctctggccc tgctgctgca tgccgccaga    60
cccgatatcc agatgaccca gaccaccagc agcctgagcg ccagcctggg cgatagagtg   120
accatcagct gcagagccag ccaggacatc agcaagtacc tgaactggta tcagcagaaa   180
cccgacggca ccgtgaagct gctgatctac cacaccagca gactgcacag cggcgtgccc   240
agcagatttt ctggcagcgg ctccggcacc gactacagcc tgaccatctc caacctggaa   300
caggaagata tcgctaccta cttctgtcag caaggcaaca ccctgcccta caccttcggc   360
```

```
ggaggcacca agctggaaat cacaggcggc ggaggatctg gcggaggcgg aagtggcgga      420
gggggatctg aagtgaaact gcaggaaagc ggccctggcc tggtggcccc atctcagtct      480
ctgagcgtga cctgtaccgt gtccggcgtg tccctgcctg actatggcgt gtcctggatc      540
agacagcccc ccagaaaggg cctggaatgg ctggagtga tctggggcag cgagacaacc       600
tactacaaca gcgccctgaa gtcccggctg accatcatca aggacaactc caagagccag      660
gtgttcctga agatgaacag cctgcagacc gacgacaccg ccatctacta ctgcgccaag      720
cactactact acggcggcag ctacgccatg gactactggg gccagggcac cagcgtgacc      780
gtgacaacaa cacccgcccc tagacctcca acccctgccc caacaatcgc cagccagcct      840
ctgtctctga ggcccgaggc ttgtagacca gctgctggcg gagccgtgca caccagagga      900
ctggatttcg cctgcgacat ctacatctgg gcccctctgg ccggcacatg tggcgtgctg      960
ctgctgagcc tcgtgatcac cctgtactgc atcgaagtga tgtaccccc tccctacctg      1020 gacaacgaga gtccaacgg caccatcatc acgtgaagg gcaagcacct gtgccccagc       1080
cctctgtttc ctggccctag caagcccttc tgggtgctgg tggtcgtggg cggagtgctg      1140
gcctgttata gcctgctcgt gacagtggcc ttcatcatct tttgggtgcg cagcaagcgg      1200
agccggctgc tgcactccga ctacatgaac atgacccca gacggccagg ccccacccgg      1260
aaacactatc agcctaacgc ccctcccaga gacttcgccg cctaccggtc taccaagttc      1320
cggggcttct gcttcatctg ctacaagacc gcccagcggc tggtgttcaa ggaccaccct      1380
cagggcaccg agcccgacat gtataagtac gacgcctacc tgtgcttcag cagcaaggac     1440
ttcacctggg tgcagaacgc cctgctgaaa cacctggaca cccagtacag cgaccagaac      1500
agattcaacc tgtgtttcga ggaacggga ttcgtgcccg gcgagaaccg gatcgccaac      1560
atccaggacg ccatctggaa cagccggaag atcgtgtgcc tggtgtcccg gcacttcctg     1620
agagatggct ggtgcctgga agcctttagc tacgcccagg gcagatgcct gagcgacctg      1680
aactccgccc tgatcatggt ggtcgtggga agcctgagcc agtaccagct gatgaagcac      1740
cagagcatca aggcttcgt gcagaagcag cagtacctgc ggtggcccga ggacttccag      1800
gatgtgggct ggttcctgca aagctgagc cagcagatcc tgaagaaaga aaaagagaag      1860
aagaaggaca caatatcccc cctgcagact gtggccacca ttagctga                  1908
```

<210> SEQ ID NO 32
<211> LENGTH: 1713
<212> TYPE: DNA
<213> ORGANISM: Artificial Sequence
<220> FEATURE:
<223> OTHER INFORMATION: Synthetic Construct

<400> SEQUENCE: 32

```
atggctctgc ctgtgacagc tctgctgctg cctctggccc tgctgctgca tgccgccaga       60
cccgatatcc agatgaccca gaccaccagc agcctgagcg ccagcctggg cgatagagtg      120
accatcagct gcagagccag ccaggacatc agcaagtacc tgaactggta tcagcagaaa      180
cccgacggca ccgtgaagct gctgatctac cacaccagca gactgcacag cggcgtgccc      240
agcagatttt ctggcagcgg ctccggcacc gactacagct tgaccatctc caacctggaa      300
caggaagata tcgctaccta cttctgtcag caaggcaaca ccctgcccta caccttcggc      360
ggaggcacca agctggaaat cacaggcggc ggaggatctg gcggaggcgg aagtggcgga      420
gggggatctg aagtgaaact gcaggaaagc ggccctggcc tggtggcccc atctcagtct      480
```

```
ctgagcgtga cctgtaccgt gtccggcgtg tccctgcctg actatggcgt gtcctggatc    540
agacagcccc ccagaaaggg cctggaatgg ctgggagtga tctggggcag cgagacaacc    600
tactacaaca gcgccctgaa gtcccggctg accatcatca aggacaactc caagagccag    660
gtgttcctga agatgaacag cctgcagacc gacgacaccg ccatctacta ctgcgccaag    720
cactactact acggcggcag ctacgccatg gactactggg gccagggcac cagcgtgacc    780
gtgacaacaa cacccgcccc tagacctcca cccctgccc caacaatcgc cagccagcct    840
ctgtctctga ggcccgaggc ttgtagacca gctgctggcg gagccgtgca ccagagga    900 ctggatttcg cctgcgacat ctacatctgg gccctctgg ccggcacatg tggcgtgctg    960
ctgctgagcc tcgtgatcac cctgtactgc aagcggggca gaaagaaact gctgtacatc   1020
tttaagcagc ccttcatgcg gcccgtgcag accacccagg aagaggacgg ctgctcctgc   1080
agattccccg aggaagaaga aggcggctgc gagctgacca gttccgggg cttctgcttc   1140 atctgctaca agaccgccca gcggctggtg ttcaaggacc accctcaggg caccgagccc   1200
gacatgtata agtacgacgc ctacctgtgc ttcagcagca aggacttcac ctgggtgcag   1260
aacgccctgc tgaaacacct ggacacccag tacagcgacc agaacagatt caacctgtgt   1320
ttcgaggaac gggacttcgt gcccggcgag aaccggatcg ccaacatcca ggacgccatc   1380
tggaacagcc ggaagatcgt gtgcctggtg tcccggcact tcctgagaga tggctggtgc   1440
ctggaagcct ttagctacgc ccagggcaga tgcctgagcg acctgaactc cgccctgatc   1500
atggtggtcg tgggcagcct gtcccagtac cagctgatga agcaccagag catcagaggc   1560
ttcgtgcaga agcagcagta cctgcggtgg cccgaggact ccaggatgt gggctggttc   1620 ctgcacaagc tgagccagca gatcctgaag aaagaaaaag agaagaagaa agacaacaat   1680
atccccctgc agacagtggc cacaatcagc tga                                1713

<210> SEQ ID NO 33
<211> LENGTH: 1812
<212> TYPE: DNA
<213> ORGANISM: Artificial Sequence
<220> FEATURE:
<223> OTHER INFORMATION: Synthetic Construct

<400> SEQUENCE: 33
atggctctgc tgtgtgacagc tctgctgctg cctctggccc tgctgctgca tgccgccaga     60
cccgatatcc agatgaccca gaccaccagc agcctgagcg ccagcctggg cgatagagtg    120
accatcagct gcagagccag ccaggacatc agcaagtacc tgaactggta tcagcagaaa    180
cccgacggca ccgtgaagct gctgatctac cacaccagca gactgcacag cggcgtgccc    240
agcagatttt ctggcagcgg ctccggcacc gactacagcc tgaccatctc caacctggaa    300
caggaagata tcgctaccta cttctgtcag caaggcaaca ccctgcccta caccttcggc    360
ggaggcacca agctggaaat cacaggcggc ggaggatctg gcggaggcgg aagtggcgga    420
gggggatctg aagtgaaact gcaggaaagc ggccctggcc tggtggcccc atctcagtct    480
ctgagcgtga cctgtaccgt gtccggcgtg tccctgcctg actatggcgt gtcctggatc    540
agacagcccc ccagaaaggg cctggaatgg ctgggagtga tctggggcag cgagacaacc    600
tactacaaca gcgccctgaa gtcccggctg accatcatca aggacaactc caagagccag    660
gtgttcctga agatgaacag cctgcagacc gacgacaccg ccatctacta ctgcgccaag    720
cactactact acggcggcag ctacgccatg gactactggg gccagggcac cagcgtgacc    780
gtggatgagg aagaggtgct gaagtctctg aagttcagcc tgttcatcgt gtgcaccgtg    840
```

```
accctgaccc tgttcctgat gaccatcctg accgtgacca agttccgggg cttctgcttc    900
atctgctaca agaccgccca gcggctggtg ttcaaggacc accctcaggg caccgagccc    960
gacatgtata agtacgacgc ctacctgtgc ttcagcagca aggacttcac ctgggtgcag   1020
aacgccctgc tgaaacacct ggacacccag tacagcgacc agaacagatt caacctgtgt   1080
ttcgaggaac gggacttcgt gcccggcgag aaccggatcg ccaacatcca ggacgccatc   1140
tggaacagcc ggaagatcgt gtgcctggtg tcccggcact tcctgagaga tggctggtgc   1200
ctggaagcct ttagctacgc ccagggcaga tgcctgagcg acctgaactc cgccctgatc   1260
atggtggtcg tgggcagcct gtcccagtac cagctgatga agcaccagag catcagaggc   1320
ttcgtgcaga agcagcagta cctgcggtgg cccgaggact tccaggatgt gggctggttc   1380
ctgcacaagc tgagccagca gatcctgaag aaagaaaaag agaagaagaa ggacaacaac   1440 atcccctgc agacagtggc caccatcagc agagtgaagt tctccagaag cgccgacgcc   1500
cctgcctacc agcagggaca gaaccagctg tacaacgagc tgaacctggg cagacgggaa   1560
gagtacgacg tgctggacaa gcggagaggc cgggatcctg aaatgggcgg caagccccag   1620
cggagaaaga accctcagga aggcctgtat aacgaactgc agaaagacaa gatggccgag   1680
gcctacagcg agatcggcat gaagggcgag cggagaagag gcaagggcca cgatggcctg   1740
taccagggcc tgagcaccgc caccaaggac acctatgacg ccctgcacat gcaggccctg   1800 cccctagat aa                                                         1812

<210> SEQ ID NO 34
<211> LENGTH: 15
<212> TYPE: PRT
<213> ORGANISM: Artificial Sequence
<220> FEATURE:
<223> OTHER INFORMATION: Synthetic Construct

<400> SEQUENCE: 34

Gly Gly Gly Gly Ser Gly Gly Gly Gly Ser Gly Gly Gly Gly Ser
1               5                  10                 15
```

CHIMERIC RECEPTORS AND METHODS OF USE THEREOF

CROSS-REFERENCE TO RELATED APPLICATIONS

This application claims the benefit of U.S. Provisional Application No. 62/327,954, filed Apr. 26, 2016, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001200SEQLIST.TXT, date recorded: Apr. 18, 2017, size: 71 KB).

FIELD OF THE INVENTION

The present disclosure relates to chimeric receptors and therapeutic uses of such chimeric receptors.

BACKGROUND OF THE INVENTION

The innate immune system plays an important role in anti-tumor immunity. The major effector cells of the innate immune system that target cancer cells include natural killer (NK) cells and myeloid cells such as dendritic cells (DCs), macrophages, and neutrophils. Although myeloid cells can promote tumor immunity by presenting tumor antigens to cytotoxic T cells and phagocytosing apoptotic tumor cells, myeloid cells are also major contributors to the chronic inflammation that drives an immunosuppressive environment benefiting tumor growth. For example, myeloid cells accumulating in tumor-bearing subjects may play an important role in tumor non-responsiveness by suppressing antigen-specific T cell responses. In addition, tumor associated macrophages (TAMs), a major inflammatory cell component of tumors, can promote immunosuppression, tumor progression, and metastases. Myeloid-derived suppressor cells (MDSCs) are also known to accumulate in cancer patients, and function by suppressing both innate and adaptive immune responses.

Therefore, myeloid cells represent an attractive therapeutic target for cancer. For example, targeted modification of myeloid cell trafficking, activation, and function may have a substantial positive impact on cancer progression. Accordingly, there is a need for approaches that enhance one or more myeloid cell activities, such as myeloid cell activation, proliferation, survival, phagocytosis, and/or functionality against pathologies associated with cancer.

All references cited herein, including patent applications and publications, are hereby incorporated by reference in their entirety.

SUMMARY OF THE INVENTION

In order to meet the above needs, certain aspects of the present disclosure relate to a polynucleotide encoding a chimeric receptor, wherein the chimeric receptor comprises: (1) an extracellular ligand-binding domain, wherein the ligand is an agent associated with cancer; (2) a transmembrane domain; and (3) a signaling domain, wherein binding of the ligand to the chimeric receptor expressed in an innate immune cell activates the signaling domain, and the activated signaling domain induces and/or enhances (i) an M1 phenotype in the innate immune cell, (ii) secretion of one or more pro-inflammatory cytokines from the innate immune cell, (iii) the innate immune cell's activity in inhibiting an immune checkpoint molecule, (iv) the innate immune cell's activity in inhibiting myeloid derived suppressor cell (MDSC) suppressor signaling, (v) the innate immune cell's activity in inducing cytotoxic T cell (CTL) activation, (vi) the innate immune cell's activity in depressing a T cell, or any combination thereof. In certain embodiments, the polynucleotide comprises a nucleic acid sequence selected from the group consisting of SEQ ID NOs: 27-33.

Other aspects of the present disclosure relate to an isolated polynucleotide encoding a chimeric receptor, wherein the polynucleotide comprises a nucleic acid sequence selected from the group consisting of SEQ ID NOs: 27-33. In certain embodiments that may be combined with any of the preceding embodiments, the chimeric receptor comprises an amino acid sequence selected form the group consisting of SEQ ID Nos: 20-26. In certain embodiments that may be combined with any of the preceding embodiments, the ligand-binding domain is selected from the group consisting of a single-domain antibody, a nanobody, a heavy-chain antibody, a $V_{NAR}$ fragment, a single-chain Fv domain (scFv), a $V_L$ domain linked to a $V_H$ domain by a flexible linker, an antibody Fab, and an extracellular domain of a receptor. In certain embodiments that may be combined with any of the preceding embodiments, the agent associated with cancer is a tumor antigen. In certain embodiments that may be combined with any of the preceding embodiments, the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1, and MAGE A3. In certain embodiments that may be combined with any of the preceding embodiments, the ligand-binding domain is a CD19 single-chain variable fragment (scFv) domain. In certain embodiments that may be combined with any of the preceding embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, and any combination thereof. In certain embodiments that may be combined with any of the preceding embodiments, the transmembrane domain is a transmembrane domain from a protein selected from the group consisting of a receptor tyrosine kinase (RTK), an M-CSF receptor, CSF-1R, Kit, TIE3, an ITAM-containing protein, DAP12, DAP10, an Fc receptor, FcR-gamma, FcR-epsilon, FcR-beta, TCR-zeta, CD3-gamma, CD3-delta, CD3-epsilon, CD3-zeta, CD3-eta, CD5, CD22, CD79a, CD79b, CD66d, TNF-alpha, NF-kappaB, a TLR (toil-like receptor), TLR5, Myd88, lymphocyte receptor chain, IL-2 receptor, IgE, IgG, CD16a, FcγRIII, FcγRII, CD28, 4-1BB, CD4, and CD8. In certain embodiments that may be combined with any of the preceding embodiments, the transmembrane domain is a transmembrane domain selected from the group consisting of a CD8 transmembrane domain, a DAP12 transmembrane domain, a CASF-1R transmembrane domain, and a TLR5 transmembrane domain. In certain embodiments that may be combined with any of the preceding embodiments, the signaling domain is a signaling domain selected from the group consisting of a 4-1BB intracellular domain, a CSF-1R receptor tyrosine kinase (RTK) intracellular domain, a TLR5 intracellular domain, a CD28 intracellular domain, and any combination thereof. In certain embodiments that may be combined with any of the preceding embodiments, the innate immune cell is an innate immune cell selected from the group consisting of macrophages, M1 macrophages, activated M1 macrophages, M2 macrophages, neutrophils, activated neutrophils, NK cells, dendritic cells, monocytes, osteoclasts, Langerhans cells, Kupffer cells, microglia, M1 microglia, activated M1 microglia, M2 microglia, astrocytes, A1 astrocytes, A2 astrocytes, and any combination thereof. In certain embodiments that may be combined with any of the preceding embodiments, the innate immune cell is a myeloid cell. In certain embodiments that may be combined with any of the preceding embodiments, the chimeric receptor further comprises one or more additional signaling domains. In certain embodiments that may be combined with any of the preceding embodiments, the one or more additional signaling domains comprise a signaling domain from one or more proteins selected from the group consisting of a receptor tyrosine kinase (RTK), an M-CSF receptor, CSF-1R, Kit, TIE3, DAP12, DAP10, an Fc receptor, FcR-gamma, FcR-epsilon, FcR-beta, TCR-zeta, CD3-gamma, CD3-delta, CD3-epsilon, CD3-zeta, CD3-eta, CD5, CD22, CD79a, CD79b, CD66d, TNF-alpha, NF-KappaB, a TLR (toll-like receptor), TLR5, Myd88, TOR/CD3 complex, lymphocyte receptor chain, IL-2 receptor, IgE, IgG, CD16a, FcγRIII, FcγRII, CD28, 4-1BB, and any combination thereof. In certain embodiments that may be combined with any of the preceding embodiments, the one or more additional signaling domains comprise a signaling domain selected from the group consisting of a CD3-zeta ITAM domain, a CD3-zeta intracellular domain, a DAP12 intracellular domain, a TCR-zeta intracellular domain, a DAP10 intracellular domain, an FcR-gamma intracellular domain, and any combination thereof. In certain embodiments that may be combined with any of the preceding embodiments, the chimeric receptor further comprises a flexible linker located between the transmembrane domain and the signaling domain. In certain embodiments that may be combined with any of the preceding embodiments, the flexible linker is a flexible linker selected from the group consisting of a CD8 hinge domain, a TLR5 hinge domain, and a CSF-1R linker domain. In certain embodiments that may be combined with any of the preceding embodiments, the chimeric receptor further comprises a signal peptide at the N-terminus of the chimeric receptor. In certain embodiments that may be combined with any of the preceding embodiments, the signal peptide is a CD8 secretory signal peptide. In certain embodiments that may be combined with any of the preceding embodiments, the chimeric receptor further comprises a heterodimerization domain. In certain embodiments that may be combined with any of the preceding embodiments, the heterodimerization domain is an inducible heterodimerization domain. In certain embodiments that may be combined with any of the preceding embodiments, the heterodimerization domain is a FK506 binding protein (FKBP) heterodimerization domain. In certain embodiments that may be combined with any of the preceding embodiments, the heterodimerization domain is a T2089L mutant of FKBP-rapamycin binding domain (FRB*) heterodimerization domain. In certain embodiments that may be combined with any of the preceding embodiments, binding of the ligand to the chimeric receptor expressed in the innate immune cell induces one or more innate immune cell activities selected from: a. TREM1 phosphorylation; b. DAP12 phosphorylation; c. activation of one or more tyrosine kinases; d. activation of phosphatidylinositol 3-kinase (PI3K); e. activation of protein kinase B; f. recruitment of phospholipase C-gamma (PLC-gamma) to a cellular plasma membrane, activation of PLC-gamma, or both; g. recruitment of TEC-family kinase dVav to a cellular plasma membrane; h. activation of nuclear factor-rB (NF-rB); i. inhibition of MAPK signaling; j. phosphorylation of linker for activation of T cells (LAT), linker for activation of B cells (LAB), or both; k. activation of IL-2-induced tyrosine kinase (ilk); l. modulation of one or more pro-inflammatory mediators selected from the group consisting of IFN-γ, IL-1α, IL-1β, TNF-α, IL-6, IL-8, CRP, IL-20 family members, IL-33, IFN-gamma, OSM, CNTF, GM-CSF, IL-11, IL-12, IL-17, IL-18, IL-23, CXCL10, MCP-1, and any combination thereof; m. modulation of one or more anti-inflammatory mediators selected from the group consisting of IL-4, IL-10, TGF-β, IL-13, IL-35, IL-16, IFN-α, IL-1Rα, VEGF, G-CSF, soluble receptors for TNF, soluble receptors for IL-6, and any combination thereof; n. phosphorylation of extracellular signal-regulated kinase (ERK); o. modulated expression of C—C chemokine receptor 7 (CCR7); p. induction of microglial cell chemotaxis toward CCL19 and CCL21 expressing cells; q. normalization of disrupted ITAM-dependent gene expression; r. recruitment of Syk, ZAP70, or both to an ITAM complex; s. increased activity of one or more ITAM-dependent genes or CSF-1R-dependent genes; t. increased maturation of dendritic cells, monocytes, microglia, M1 microglia, activated M1 microglia, and M2 microglia, macrophages, M1 macrophages, activated M1 macrophages, M2 macrophages, astrocytes, A1 astrocytes, A2 astrocytes, or any combination thereof; u. increased ability of dendritic cells, monocytes, microglia, M1 microglia, activated M1 microglia, and M2 microglia, macrophages, M1 macrophages, activated M1 macrophages, M2 macrophages, astrocytes, A1 astrocytes, A2 astrocytes, or any combination thereof to prime or modulate the function of T cells; v. enhanced ability, normalized ability, or both of bone marrow-derived dendritic cells to prime or modulate function of antigen-specific T cells; w. induction of osteoclast production, increased rate of osteoclastogenesis, or both; x. increased survival of dendritic cells, macrophages, M1 macrophages, activated M1 macrophages, M2 macrophages, monocytes, osteoclasts, Langerhans cells, Kupffer cells, microglia, M1 microglia, activated M1 microglia, M2 microglia, Astrocytes, A1 astrocytes, A2 astrocytes, or any combination thereof; y. increased function of dendritic cells, macrophages, M1 macrophages, activated M1 macrophages, M2 macrophages, microglia, M1 microglia, activated M1 microglia, M2 microglia, astrocytes, A1 astrocytes, A2 astrocytes, or any combination thereof; z. increasing phagocytosis by dendritic cells, macrophages, M1 macrophages, activated M1 macrophages, M2 macrophages, monocytes, microglia, M1 microglia, activated M1 microglia, M2 microglia, astrocytes, A1 astrocytes, A2 astrocytes, or any combination thereof; aa. induction of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, disease-causing nucleic acid clearance, tumor cell clearance, and any combination thereof; bb. induction of phagocytosis of one or more of apoptotic neurons, nerve tissue debris, non-nerve tissue debris, dysfunctional synapses, bacteria, other foreign bodies, disease-causing proteins, disease-causing peptides, disease-causing nucleic acids, tumor cells, or any combination thereof; cc. increased expression of one or more stimulatory molecules selected from the group consisting of CD83, CD86 MHC class II, CD40, and any combination thereof; dd. modulated expression of one or more proteins selected from the group consisting of C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, VEGF, and any combination thereof; ee. activation of tumor cell killing by one or more of microglia, macrophages, dendritic cells, bone marrow-derived dendritic cells, neutrophils, or any combination thereof; ff. activating anti-tumor cell proliferation activity of one or more of microglia, macrophages, dendritic cells, bone marrow-derived dendritic cells, neutrophils, or any combination thereof; gg. activating anti-tumor cell metastasis activity of one or more of microglia, macrophages, dendritic cells, bone marrow-derived dendritic cells, neutrophils, or any combination thereof; hh. decreasing tumor volume; ii. decreasing tumor growth rate; and jj. increasing efficacy of one or more immune-therapies that modulate anti-tumor T cell responses, optionally wherein the one or more immune-therapies are selected from PD1/PDL1 blockade, CTLA-4 blockade, and cancer vaccines. In certain embodiments that may be combined with any of the preceding embodiments, the polynucleotide is a DNA polynucleotide. In certain embodiments that may be combined with any of the preceding embodiments, the polynucleotide is an RNA polynucleotide.

Other aspects of the present disclosure relate to a vector comprising the polynucleotide of any of the preceding embodiments. In certain embodiments, the vector is a lentiviral vector, a retroviral vector, a sleeping beauty vector, an AAV vector, or a non-viral plasmid vector.

Other aspects of the present disclosure relate to an isolated chimeric receptor encoded by the polynucleotide of any of the preceding embodiments.

Other aspects of the present disclosure relate to an isolated innate immune cell comprising the polynucleotide of any of the preceding embodiments. Other aspects of the present disclosure relate to an isolated innate immune cell comprising the vector of any of the preceding embodiments. Other aspects of the present disclosure relate to an isolated innate immune cell comprising the chimeric receptor of any of the preceding embodiments. In certain embodiments that may be combined with any of the preceding embodiments, the cell is a myeloid cell. In certain embodiments that may be combined with any of the preceding embodiments, the cell is selected from the group consisting of a macrophage, an M1 macrophage, an activated M1 macrophage, an M2 macrophage, a neutrophil, a NK cell, a dendritic cell, a monocyte, an osteoclast, a Langerhans cell, a Kupffer cell, a microglial cell, an M1 microglial cell, an activated M1 microglial cell, an M2 microglial cell, an astrocyte, an A1 astrocyte, and an A2 astrocyte. In certain embodiments that may be combined with any of the preceding embodiments, the cell lacks one or more genes encoding one or more immune molecules that allow for recognition by the adaptive immune system. In certain embodiments that may be combined with any of the preceding embodiments, the one or more immune molecules are MHC class I molecules, MHC class I co-receptors, MHC class II molecules, MHC class II co-receptors, or any combination thereof. In certain embodiments that may be combined with any of the preceding embodiments, the one or more genes were deleted using a nuclease selected from the group consisting of a Cas9 nuclease, a TALEN, and a ZFN.

Other aspects of the present disclosure relate to an isolated myeloid cell expressing the chimeric receptor of any of the preceding embodiments, wherein the cell phenotype is modified in vitro or in vivo by addition of one or more of GM-CSF, MCSF, IL-1, IL-4, IL-10, IL-12, TNF-α, TGF-beta, LPS, or any combination thereof.

Other aspects of the present disclosure relate to a method of producing an innate immune cell expressing a chimeric receptor, comprising: (a) isolating an innate immune cell; (b) introducing the vector of any of the preceding embodiments into the cell; and (c) culturing the cell so that the chimeric receptor is expressed. In certain embodiments that may be combined with any of the preceding embodiments, the innate immune cell is a myeloid cell. In certain embodiments that may be combined with any of the preceding embodiments, the innate immune cell is selected from the group consisting of a macrophage, an M1 macrophage, an activated M1 macrophage, an M2 macrophage, a neutrophil, a NK cell, a dendritic cell, a monocyte, an osteoclast, a Langerhans cell, a Kupffer cell, a microglial cell, an M1 microglial cell, an activated M1 microglial cell, an M2 microglial cell, an astrocyte, an A1 astrocyte, and an A2 astrocyte. Other aspects of the present disclosure relate to an isolated innate immune cell comprising a chimeric receptor produced by the method of any one of the preceding embodiments.

In certain embodiments that may be combined with any of the preceding embodiments, the cell further expresses one or more signaling factors that promote an M2 phenotype by inhibiting a TNF-alpha/NF-KappaB pathway a TLR/MyD88 pathway, or both. In certain embodiments that may be combined with any of the preceding embodiments, the one or more signaling factors that promote an M2 phenotype by inhibiting a TNF-alpha/NF-KappaB pathway are selected from the group consisting of a dominant negative IKK-alpha, a dominant negative IKK-alpha IKK-beta, a dominant negative IKK-alpha IKBa (IKBa-DN), a MEKK isoform, and any combination thereof. In certain embodiments that may be combined with any of the preceding embodiments, the one or more signaling factors that promote an M2 phenotype by inhibiting a TLR/MyD88 pathway are one or more dominant negative forms of MyD88.

Other aspects of the present disclosure relate to a pharmaceutical composition comprising the polynucleotide of any of the preceding embodiments, and a pharmaceutically acceptable carrier. Other aspects of the present disclosure relate to a pharmaceutical composition comprising the vector of any of the preceding embodiments, and a pharmaceutically acceptable carrier. Other aspects of the present disclosure relate to a pharmaceutical composition comprising the chimeric receptor of any of the preceding embodiments, and a pharmaceutically acceptable carrier. Other aspects of the present disclosure relate to a pharmaceutical composition comprising the isolated cell of any of the preceding embodiments, and a pharmaceutically acceptable carrier.

Other aspects of the present disclosure relate to a method of preventing, reducing risk, or treating cancer, comprising administering to an individual in need thereof a therapeutically effective amount of the isolated cell of any of the preceding embodiments. Other aspects of the present disclosure relate to an isolated cell of any of the preceding embodiments for use in preventing, reducing risk, or treating cancer in an individual in need thereof. Other aspects of the present disclosure relate to use of an isolated cell of any of the preceding embodiments in the manufacture of a medicament for preventing, reducing risk, or treating cancer in an individual in need thereof.

Other aspects of the present disclosure relate to a method of preventing, reducing risk, or treating cancer in an individual in need thereof, comprising: (a) obtaining a plurality of isolated innate immune cells; (b) introducing the vector of any of the preceding embodiments into the plurality of isolated innate immune cells; and (c) administering to the individual a therapeutically effective amount of the plurality of isolated innate immune cells containing the vector. Other aspects of the present disclosure relate to an isolated innate immune cells containing the vector of any of the preceding embodiments for use in preventing, reducing risk, or treating cancer in an individual in need thereof. Other aspects of the present disclosure relate to use of an isolated innate immune cells containing the vector of any of the preceding embodiments in the manufacture of a medicament for preventing, reducing risk, or treating cancer in an individual in need thereof.

In certain embodiments that may be combined with any of the preceding embodiments, binding of the ligand to the chimeric receptor expressed in the cell induces an increase in myeloid cell activation, proliferation, survival, phagocytosis, and/or functionality. In certain embodiments that may be combined with any of the preceding embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, and any combination thereof. In certain embodiments that may be combined with any of the preceding embodiments, the cells are selected from the group consisting of macrophages, M1 macrophages, activated M1 macrophages, M2 macrophages, neutrophils, NK cells, dendritic cells, monocytes, osteoclasts, Langerhans cells, Kupffer cells, microglia, M1 microglia, activated M1 microglia, M2 microglia, astrocytes, A1 astrocytes, A2 astrocytes, and any combination thereof. In certain embodiments that may be combined with any of the preceding embodiments, the administering induces one or more activities selected from: a. TREM1 phosphorylation; b. DAP12 phosphorylation; c. activation of one or more tyrosine kinases; d. activation of phosphatidylinositol 3-kinase (PI3K); e. activation of protein kinase B; f. recruitment of phospholipase C-gamma (PLC-gamma) to a cellular plasma membrane, activation of PLC-gamma, or both; g. recruitment of TEC-family kinase dVav to a cellular plasma membrane; h. activation of nuclear factor-rB (NF-rB); i. inhibition of MAPK signaling; j. phosphorylation of linker for activation of T cells (LAT), linker for activation of B cells (LAB), or both; is. activation of IL-2-induced tyrosine kinase (ilk); l. modulation of one or more pro-inflammatory mediators selected from the group consisting of IFN-γ, IL-1α, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, MCP-1, and any combination thereof; m. modulation of one or more anti-inflammatory mediators selected from the group consisting of IL-4, IL-10, TGF-β, IL-13, IL-35, IL-16, IFN-α, IL-1Rα, VEGF, G-CSF, soluble receptors for TNF, soluble receptors for IL-6, and any combination thereof; n. phosphorylation of extracellular signal-regulated kinase (ERK); o. modulated expression of C—C chemokine receptor 7 (CCR7); p. induction of microglial cell chemotaxis toward CCL19 and CCL21 expressing cells; q. normalization of disrupted ITAM-dependent gene expression; r. recruitment of Syk, ZAP70, or both to an ITAM complex; s. increased activity of one or more ITAM-dependent genes or CSF-1R-dependent genes; t. increased maturation of dendritic cells, monocytes, microglia, M1 microglia, activated M1 microglia, and M2 microglia, macrophages, M1 macrophages, activated M1 macrophages, M2 macrophages, astrocytes, A1 astrocytes, A2 astrocytes, or any combination thereof; u. increased ability of dendritic cells, monocytes, microglia, M1 microglia, activated M1 microglia, and M2 microglia, macrophages, M1 macrophages, activated M1 macrophages, M2 macrophages, astrocytes, A1 astrocytes, A2 astrocytes, or any combination thereof to prime or modulate the function of T cells; v. enhanced ability, normalized ability, or both of bone marrow-derived dendritic cells to prime or modulate function of antigen-specific T cells; w. induction of osteoclast production, increased rate of osteoclastogenesis, or both; x. increased survival of dendritic cells, macrophages, M1 macrophages, activated M1 macrophages, M2 macrophages, monocytes, osteoclasts, Langerhans cells, Kupffer cells, microglia, M1 microglia, activated M1 microglia, M2 microglia, Astrocytes, A1 astrocytes, A2 astrocytes, or any combination thereof; y. increased function of dendritic cells, macrophages, M1 macrophages, activated M1 macrophages, M2 macrophages, microglia, M1 microglia, activated M1 microglia, M2 microglia, astrocytes, A1 astrocytes, A2 astrocytes, or any combination thereof; z. increasing phagocytosis by dendritic cells, macrophages, M1 macrophages, activated M1 macrophages, M2 macrophages, monocytes, microglia, M1 microglia, activated M1 microglia, M2 microglia, astrocytes, A1 astrocytes, A2 astrocytes, or any combination thereof; aa. induction of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, disease-causing nucleic acid clearance, tumor cell clearance, and any combination thereof; bb. induction of phagocytosis of one or more of apoptotic neurons, nerve tissue debris, non-nerve tissue debris, dysfunctional synapses, bacteria, other foreign bodies, disease-causing proteins, disease-causing peptides, disease-causing nucleic acids, tumor cells, or any combination thereof; cc. increased expression of one or more stimulatory molecules selected from the group consisting of CD83, CD86 MHC class II, CD40, and any combination thereof; dd. modulated expression of one or more proteins selected from the group consisting of C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, VEGF, and any combination thereof; ee. activation of tumor cell killing by one or more of microglia, macrophages, dendritic cells, bone marrow-derived dendritic cells, neutrophils, or any combination thereof; ff. activating anti-tumor cell proliferation activity of one or more of microglia, macrophages, dendritic cells, bone marrow-derived dendritic cells, neutrophils, or any combination thereof; gg. activating anti-tumor cell metastasis activity of one or more of microglia, macrophages, dendritic cells, bone marrow-derived dendritic cells, neutrophils, or any combination thereof; hh. decreasing tumor volume; ii. decreasing tumor growth rate; and jj. increasing efficacy of one or more immune-therapies that modulate anti-tumor T cell responses, optionally wherein the one or more immune-therapies are selected from PD1/PDL1 blockade, CTLA-4 blockade, and cancer vaccines. In certain embodiments that may be combined with any of the preceding embodiments, the method further comprises administering to the individual at least one antibody that specifically binds to an inhibitory checkpoint molecule, and/or one or more standard or investigational anti-cancer therapies. In certain embodiments that may be combined with any of the preceding embodiments, the at least one antibody that specifically binds to an inhibitory checkpoint molecule is administered in combination with the cells. In certain embodiments that may be combined with any of the preceding embodiments, the at least one antibody that specifically binds to an inhibitory checkpoint molecule is selected from the group consisting of an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-AZAR antibody, an anti-LAG-3 antibody, an anti-phosphatidylserine antibody, an anti-CD27 antibody, an anti-TNF-α antibody, an anti-CD33 antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, and any combination thereof. In certain embodiments that may be combined with any of the preceding embodiments, the one or more standard or investigational anti-cancer therapies are selected from the group consisting of radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy. hi certain embodiments that may be combined with any of the preceding embodiments, the method further comprises administering to the individual at least one antibody that specifically binds to an inhibitory cytokine. In certain embodiments that may be combined with any of the preceding embodiments, the at least one antibody that specifically binds to an inhibitory cytokine is administered in combination with the cells. In certain embodiments that may be combined with any of the preceding embodiments, the at least one antibody that specifically binds to an inhibitory cytokine is selected from the group consisting of an anti-CCL2 antibody, an anti-CSF-1 antibody, an anti-IL-2 antibody, and any combination thereof. In certain embodiments that may be combined with any of the preceding embodiments, the method further comprises administering to the individual at least one agonistic antibody that specifically binds to a stimulatory checkpoint protein. In certain embodiments that may be combined with any of the preceding embodiments, the at least one agonistic antibody that specifically binds to a stimulatory checkpoint protein is administered in combination with the cells. In certain embodiments that may be combined with any of the preceding embodiments, the at least one agonistic antibody that specifically binds to a stimulatory checkpoint protein is selected from the group consisting of an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof. In certain embodiments that may be combined with any of the preceding embodiments, the method further comprises administering to the individual at least one stimulatory cytokine. In certain embodiments that may be combined with any of the preceding embodiments, the at least one stimulatory cytokine is administered in combination with the cells. In certain embodiments that may be combined with any of the preceding embodiments, the at least one stimulatory cytokine is selected from the group consisting of IFN-α4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, MCP-1, MIP-1-beta, and any combination thereof.

BRIEF DESCRIPTION OF THE DRAWINGS

FIG. 1A and FIG. 1B show a schematic of the SMART1 chimeric receptor structure (FIG. 1A) and a schematic of a vector that harbors this receptor cloned into pCDNA3.4-Topo from Life Technologies (FIG. 1B). SMART1 is composed of the elements: CD8 secretory signal sequence (SS)>>anti-CD19 scFv>>CD8 Hinge domain>>CD8 transmembrane domain (TM)>>4-1BB intracellular>>CD3Zeta ITAM domain.

FIG. 3A and FIG. 3B show a schematic of the SMART12 chimeric receptor structure (FIG. 3A) and a schematic of a vector that harbors this receptor cloned into pCDNA3.4-Topo from Life Technologies (FIG. 3B). SMART12 is composed of the elements: CD8 SS>>anti-CD19 SCfV>>CD8 Hinge>>CD8TM>>TLR5 intracellular domain.

Figure 2A:
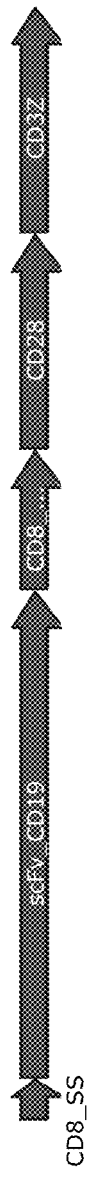
FIG. 2A and FIG. 2B show a schematic of the SMART11 chimeric receptor structure (FIG. 2A) and a schematic of a vector that harbors this receptor cloned into pCDNA3.4-Topo from Life Technologies (FIG. 2B). SMART11 is composed of the elements: CD8 SS>>anti-CD19 SCfV>>CD8 Hinge>>CD8TM>>CD28>>CD3Zeta ITAM.

SCfV>>TLR5 hinge and transmembrane>> TLR5 intracellular>>CD3zeta intracellular domain.

DETAILED DESCRIPTION OF THE INVENTION

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual,* and *Animal Cell Culture* (R. I. Freshney, ed. (1987)); *Oligonucleotide Synthesis* (M. J. Gait, ed., 1984); *Methods in Molecular Biology,* Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction,* (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the chimeric receptors to elicit a desired response in the individual. A therapeutically effective amount is also one in which any toxic or detrimental effects of the chimeric receptors are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., Basic and Clinical Immunology, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, 4$^{th}$ ed. (W.B. Saunders Co., 2000).

The "variable region" or "variable domain" of an antibody, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10):1057-1062 (1995)); single-chain antibody molecules and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment includes an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment includes of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding. For a review of the sFv, see Plückthun in The Pharmacology of Monoclonal Antibodies, vol. 113, Rosenburg and Moore eds., Springer-Verlag, New York, pp. 269-315 (1994).

"Functional fragments" of antibodies, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Nat'l Acad. Sci. USA 90:6444-48 (1993).

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu in Methods in Molecular Biology 248:1-25 (Lo, ed., Human Press, Totowa, N.J., 2003)).

As use herein, the term "specifically recognizes" or "specifically binds" refers to measurable and reproducible interactions such as attraction or binding between a ligand and a chimeric receptor that is determinative of the presence of the target in the presence of a heterogeneous population of molecules including biological molecules. For example, a chimeric receptor of the present disclosure, that specifically or preferentially binds to a ligand or target with greater affinity, avidity, more readily, and/or with greater duration than it binds to other ligands or targets. It is also understood by reading this definition that, for example, a chimeric receptor that specifically or preferentially binds to a first target may or may not specifically or preferentially bind to a second target. As such, "specific binding" or "preferential binding" does not necessarily require (although it can include) exclusive binding. An chimeric receptor that specifically binds to a target may have an association constant of at least about $10^3 M^{-1}$ or $10^4 M^{-1}$, sometimes about $10^5 M^{-1}$ or $10^6 M^{-1}$, in other instances about $10^6 M^{-1}$ or $10^7 M^{-1}$, about $10^8 M^{-1}$ to $10^9 M^{-1}$, or about $10^{10} M^{-1}$ to $10^{11} M^{-1}$ or higher. A variety of immunoassay formats can be used to select chimeric receptors specifically immunoreactive with a particular protein. See, e.g., Harlow and Lane (1988) Antibodies, A Laboratory Manual, Cold Spring Harbor Publications, New York, for a description of immunoassay formats and conditions that can be used to determine specific immunoreactivity.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

The term "isolated" refers a molecule or cell that is identified and separated from at least one contaminant molecule or cell with which it is ordinarily associated in the environment in which it was produced. Preferably, the isolated molecule or cell is free of association with all components associated with the production environment. The isolated molecule or cell is in a form other than in the form or setting in which it is found in nature.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

The term "ligand" as used herein refers to a molecule that binds to another molecule, such as a receptor or an antibody. For example, as used herein, a ligand is any compound or agent bound by a chimeric receptor's ligand-binding domain. Exemplary ligands include nucleic acids, peptides, or proteins associated with cancer.

The term "nanobody," also called a single-domain antibody, as used herein refers to an antibody fragment that includes a single monomeric variable antibody domain that binds to a specific antigen. Nanobodies may include a peptide chain of about 110 amino acids and may have one variable domain of a heavy-chain antibody or of a common IgG.

The term "$V_{NAR}$" as used herein refers to a single variable new antigen receptor (NAR) domain antibody fragment. $V_{NAR}$ fragments are single-domain antibody fragments derived from heavy-chain antibodies, such as shark immunoglobulin new antigen receptor antibodies (IgNARs).

The term "extracellular receptor domain" as used herein refers to the portion of a cell bound receptor protein that is found externally on a cell. The extracellular receptor domain functions by binding to a ligand. For example, nucleic acids, peptides, proteins, or atomic ions may each bind to an extracellular receptor domain as a ligand.

The term "autologous" refers to any material derived from the same individual to whom it is later to be re-introduced.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the disclosures described herein include "comprising," "consisting," and "consisting essentially of" aspects and embodiments.

Overview

The present disclosure relates to chimeric receptors comprising an extracellular ligand-binding domain that binds an agent associated with cancer; a transmembrane domain; and a signaling domain. Some embodiments of the present disclosure include polynucleotides encoding chimeric receptors, and vectors comprising said polynucleotides. Further embodiments include innate immune cells expressing said chimeric receptors and methods of producing such innate immune cells by introducing polynucleotides or vectors encoding chimeric receptors into the cells. In some embodiments, innate immune cells expressing chimeric receptors of the present disclosure are administered to an individual to treat or prevent cancer. In some embodiments, binding of the ligand to the chimeric receptor expressed in an innate immune cell activates the signaling domain, and the activated signaling domain induces and/or enhances an M1 phenotype in the innate immune cell, secretion of one or more pro-inflammatory cytokines from the innate immune cell, the innate immune cell's activity in inhibiting an immune checkpoint molecule, the innate immune cell's activity in inhibiting myeloid derived suppressor cell (MDSC) signaling, the innate immune cell's activity in inducing cytotoxic T cell (CTL) activation, or the innate immune cell's activity in depressing a T cell.

In some embodiments, the chimeric receptors of the present disclosure can be used to increase myeloid cell activation, proliferation, survival, phagocytosis, and/or functionality against pathologies associated with cancer.

Chimeric Receptors

Certain aspects of the present disclosure relate to a chimeric receptor. A chimeric receptor, as used herein, refers to a set of polypeptides, which when in an innate immune cell, provides the cell with specificity for a target ligand and with intracellular signal generation. In some aspects, the set of polypeptides are contiguous with each other, e.g., are in the same polypeptide chain (e.g., comprise a chimeric fusion protein). In some embodiments, the set of polypeptides are not contiguous with each other, e.g., are in different polypeptide chains. A chimeric receptor described herein at least comprises an extracellular ligand-binding domain, a transmembrane domain, and a cytoplasmic signaling domain (also referred to herein as "an intracellular signaling domain") comprising a functional signaling domain derived from a stimulatory molecule and/or costimulatory molecule. In one aspect, the cytoplasmic signaling domain further comprises one or more functional signaling domains derived from at least one costimulatory molecule. In some embodiments, the extracellular domain of the chimeric receptor binds a ligand and transmits a signal to the cytoplasmic domain which transduces an effector function signal to the cell in which the receptor is expressed.

In some embodiments, the chimeric receptor includes two proteins, with each protein including one or more domains. For example, a chimeric receptor of the present disclosure can be a two-component receptor. Two-component chimeric receptors include two separate polypeptides that can associate, dimerize, or multimerize through an interaction domain. In some embodiments the chimeric receptor further comprises a flexible linker located between the transmembrane domain and the signaling domain. The flexible linker allows the ligand-binding domain to orient in different directions to facilitate ligand recognition and binding. Exemplary flexible linkers include, without limitation, a CD8 hinge domain, a TLR5 hinge domain, and a CSF-1R linker domain. In some embodiments, the chimeric receptor further comprises a signal peptide at the N-terminus of the chimeric receptor. The signal peptide directs the nascent chimeric receptor protein into the endoplasmic reticulum. This allows the receptor to be glycosylated and anchored in the cell membrane. In some embodiments, the signal peptide is a CD8 secretory signal peptide.

Ligand-Binding Domains

In some embodiments, chimeric receptors of the present disclosure include a ligand-binding domain. A ligand-binding domain refers to any suitable protein which binds to a specific ligand. The binding domain may include a part of antibody that binds to an antigen, such as an immunoglobulin chain or fragment comprising at least one immunoglobulin variable domain sequence. The portion of the chimeric receptor that includes an antibody or antibody fragment may exist in a variety of forms where the antigen binding domain is expressed as part of a contiguous polypeptide chain. The ligand-binding domain can be any domain that binds to a ligand including but not limited to a monoclonal antibody, a polyclonal antibody, a recombinant antibody, a murine antibody, a human antibody, a humanized antibody, and a functional fragment thereof, including but not limited to a single-domain antibody such as a heavy chain variable domain (VH), a light chain variable domain (VL), a variable domain (VHH) of a camelid derived nanobody, a heavy-chain antibody, a single domain antibody fragment ($V_{NAR}$) fragment, a single-chain Fv domain (scFv), a $V_L$ domain linked to a $V_H$ domain by a flexible linker, or an antibody Fab. In some embodiments, the ligand-binding domain is a scFv. ScFv molecules can be produced by linking VH and VL regions together using flexible polypeptide linkers. In some embodiments, scFv molecules comprise a linker (e.g., a Ser-Gly linker) with an optimized length and/or amino acid composition. The linker length can greatly affect how the variable regions of a scFv fold and interact. The linker sequence may comprise any naturally occurring amino acid. In some embodiments, the linker sequence comprises amino acids glycine and serine.

In some instances, it is beneficial for the ligand-binding domain to be derived from the same species in which the chimeric receptor will ultimately be used in. For example, for use in humans, it may be beneficial for the ligand-binding domain of the chimeric receptor to comprise human or humanized residues for the ligand-binding domain of an antibody or antibody fragment.

The ligand-binding domain may alternatively include a ligand-binding portion of a cell receptor protein. For example, the ligand-binding portion can include an extracellular receptor domain. An extracellular receptor domain includes the portion of a cell bound receptor protein that is found externally on the cell. Exemplary extracellular receptor domains, include, without limitation, those derived from a TCRs, MHC molecules, TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CD8, CD7, CD287, LIGHT, NKG2C, NKG2D, SLAMF7, NKp80, NKp30, NKp44, NKp46, CD160, B7-H3, and a ligand that specifically binds with CD83.

The ligand-binding domain of the present disclosure may bind any suitable ligand. Exemplary ligands include, without limitation, peptides, proteins, and nucleic acids. The choice of extracellular ligand-binding domain depends upon the type and number of ligands that define the target of the chimeric receptor. In some embodiments, the ligand-binding domain may be chosen to recognize an agent that is associated with a disease state. In some embodiments, the ligand-binding domain may bind an agent associated with cancer. Exemplary cancers include, without limitation, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, and thyroid cancer.

In some embodiments, the chimeric receptor-mediated immune cell response can be directed to an agent of interest by way of engineering a ligand-binding domain that specifically binds a desired agent into the chimeric receptor. The ligand-binding domain can be designed to specifically target an agent associated with cancer. In some embodiments, the agent is a nucleic acid, peptide, or protein associated with cancer. In some embodiments, the agent is a wild-type nucleic acid, peptide, or protein. In some embodiments, the agent is a mutant nucleic acid, peptide, or protein.

In some embodiments, the agent associated with cancer is a tumor antigen. Exemplary tumor antigens include, without limitation, CD19, CD20, CD22, receptor tyrosine kinase-like orphan receptor 1 (ROR1), mesothelin, CD33/interleukin-3 receptor alpha (IL3Ra), c-Met, prostate-specific membrane antigen (PSMA), Glycolipid F77, type III epidermal growth factor receptor mutation (EGFRvIII), disialoganglioside GD-2, NY-ESO-1 (also known as cancer/testis antigen 1B or CTAG1B), and Melanoma-associated antigen 3 (MAGE A3). In some embodiments, the tumor antigen-expressing cells express, or at any time expressed, mRNA encoding the tumor antigen. In some embodiments, the tumor antigen-expressing cells produce the tumor antigen protein (e.g., wild-type or mutant), and the tumor antigen protein may be present at normal levels or reduced levels. In one embodiment, the tumor antigen-expressing cells produced detectable levels of a tumor antigen protein at one point, and subsequently produced substantially no detectable tumor antigen protein.

In some embodiments, the ligand-binding domain binds to CD19. CD19 is a B-lymphocyte antigen that is expressed on the surface of B cells and functions as a B cell co-receptor by binding to CD81 and CD82 and enhancing signaling through the B cell receptor. In some embodiments, CD19 may be expresses on cells associated with proliferative diseases such as a cancer, malignancy, or a precancerous condition such as a myelodysplasia, a myelodysplasia syndrome, or a preleukemia. CD19 is expressed on most B lineage cancers, including, e.g., acute lymphoblastic leukaemia, chronic lymphocyte leukaemia and non-Hodgkin lymphoma. In some embodiments, the CD19 protein may include mutations, e.g., point mutations, fragments, insertions, deletions and splice variants of full length wild-type CD19. In some embodiments, the ligand-binding portion of the chimeric receptor recognizes and binds an antigen within the extracellular domain of the CD19 protein. In some embodiments, the CD19 protein is expressed on a cancer cell.

In some embodiments, the ligand-binding domain includes a single-chain variable fragment (scFv) domain that binds to a specific cancer agent. Exemplary scFV domains include, without limitation, CD19, EpCAM, CD20, CD16, CEA, PSMA, HER2, HER3, IGF1R, VEGF-A, Ang-2, WT1, PR1, E75, p53, Ras, AFP, URLC10, VEGFR1 and 2, MAGE, gp100, MART-1, Tyrosinase, NY-ESO-1, Survivin, mutant p53, and MUC-1. In some embodiments, the anti-CD19 scFV domain binds CD19. In some embodiments, the anti-EpCAM scFV domain binds EpCAM. In some embodiments, the anti-CD20 scFV domain binds CD20. In some embodiments, the anti-CD16 scFV domain binds CD16. In some embodiments, the anti-CEA scFV domain binds CEA. In some embodiments, the anti-PSMA scFV domain binds PSMA. In some embodiments, the anti-HER2 scFV domain binds HER2. In some embodiments, the anti-HER3 scFV domain binds HER3. In some embodiments, the anti-IGF1R scFV domain binds IGF1R. In some embodiments, the anti-VEGF-A scFV domain binds VEGF-A. In some embodiments, the anti-Ang-2 scFV domain binds Ang-2. In some embodiments, the anti-WT1 scFV domain binds WT1. In some embodiments, the anti-PR1 scFV domain binds PR1. In some embodiments, the anti-E75 scFV domain binds E75. In some embodiments, the anti-p53 scFV domain binds p53. In some embodiments, the anti-Ras scFV domain binds Ras. In some embodiments, the anti-AFP scFV domain binds AFP. In some embodiments, the anti-URLC10 scFV domain binds URLC10. In some embodiments, the anti-VEGFR1 scFV domain binds VEGFR1. In some embodiments, the anti-VEGFR2 scFV domain binds VEGFR2. In some embodiments, the anti-MAGE scFV domain binds MAGE. In some embodiments, the anti-gp100 scFV domain binds gp100. In some embodiments, the anti-MART-1 scFV domain binds MART-1. In some embodiments, the anti-Tyrosinase scFV domain binds Tyrosinase. In some embodiments, the anti-NY-ESO-1 scFV domain binds NY-ESO-1. In some embodiments, the anti-Survivin scFV domain binds Survivin. In some embodiments, the anti-mutant p53 scFV domain binds mutant p53. In some embodiments, the anti-MUC-1 scFV domain binds MUC-1.

Transmembrane Domains

In some embodiments, chimeric receptors of the present disclosure comprise a transmembrane domain. As used herein, a transmembrane domain refers to a portion of a protein structure that is located in a membrane. Transmembrane domains may be a single alpha helix, a transmembrane beta barrel, or any other structure which is thermodynamically stable in a membrane. The transmembrane domain of the chimeric receptor may be derived from any membrane bound or transmembrane protein.

In some embodiments, the chimeric receptor may be designed to include a transmembrane domain that is fused to the extracellular ligand-binding domain of the chimeric receptor. In one embodiment, the transmembrane domain that naturally is associated with one of the domains in the chimeric receptor is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived from a natural source. For example, the domain may be derived from any membrane bound or transmembrane protein. Transmembrane regions for use in the chimeric receptors disclosed herein may be derived from a protein including, without limitation, a receptor tyrosine kinase (RTK), an macrophage colony-stimulating factor (M-CSF) receptor, colony stimulating factor 1 receptor (CSF-1R), Kit, Tetrahymena insertion-homing endonuclease 3 (TIE3), an immunoreceptor tyrosine-based activation motif (ITAM)-containing protein, DNAX-activation protein 12 (DAP12), DNAX-activation protein 10 (DAP10), an Fc receptor, FcR-gamma, FcR-epsilon, FcR-beta, T cell receptor zeta (TCR-zeta), cluster of differentiation (CD) 3-gamma, CD3-delta, CD3-epsilon, CD3-zeta, CD3-eta, CD5, CD22, CD79a, CD79b, CD66d, tumor necrosis factor (TNF)-alpha, nuclear factor kappa-light-chain-enhancer of activated B cells (NF-kappaB), a toll-like receptor (TLR), TLR5, myeloid differentiation primary response gene 88 (Myd88), lymphocyte receptor chain, interleukin-2 (IL-2) receptor, Immunoglobulin E (IgE), Immunoglobulin G (IgG), CD16α, FcγRIII, FcγRII, CD28, 4-1BB, CD4, and CD8. In some embodiments, the transmembrane domain is a CD8 transmembrane domain, a DAP12 transmembrane domain, a cCSF-1R transmembrane domain, or a TLR5 transmembrane domain.

Signaling Domains

In some embodiments, chimeric receptors of the present disclosure comprise a signaling domain. As used herein, a signaling domain refers to the functional portion of a protein which acts by transmitting information within the cell to regulate cellular activity via defined signaling pathways by generating second messengers or functioning as effectors by responding to such messengers.

In some embodiments, a signaling domain of the present disclosure may refer to the portion of a chimeric receptor which transduces the effector function signal, resulting in functional activities of the innate immune cell in which the chimeric receptor has been placed. Functional activities of an innate immune cell, for example, may be phagocytosis, secretion of cytokines, or trafficking. In some embodiments, the signaling domains promote function, migration, survival, and proliferation of immune cells. The entire intracellular signaling domain can be employed, or a truncated portion of the intracellular signaling domain can be used. To the extent that a truncated portion of the intracellular signaling domain is used, such truncated portion may be used in place of the entire intracellular signaling domain as long as it transduces the effector function signal. The term intracellular signaling domain is thus meant to include any truncated portion of the intracellular signaling domain sufficient to transduce the effector function signal.

In some embodiments binding of the ligand to the chimeric receptor expressed in an innate immune cell activates the signaling domain, and the activated signaling domain induces and/or enhances an immune cell function including, without limitation, cell survival of the immune cell, proliferation of the immune cell, migration of the immune cell, or functionality of the immune cell. In some embodiments, signaling is induced through multimerization or clustering of the chimeric receptors upon binding to ligand. In some embodiments, signaling is induced when multiple copies of the ligand are present. In some embodiments, ligand binding and subsequent signaling through the chimeric receptors may be involved in survival and localization of immune cells at cites of pathology occurring in cancer.

Examples of intracellular signaling domains for use in the chimer receptor include the cytoplasmic sequences of the T cell receptor (TCR) and co-receptors that act in concert to initiate signal transduction following receptor engagement, as well as any derivative or variant of these sequences and any recombinant sequence that has the same functional capability. It is known that signals generated through the TCR alone are insufficient for full activation of the cell and that a secondary and/or costimulatory signal is also required. Thus, cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain). A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs. Examples of ITAM containing primary intracellular signaling domains that may be used in the chimeric receptors disclosed herein include those of CD3 zeta, common FcR gamma (FCERIG), Fc gamma RIIa, FcR beta (Fc Epsilon Rib), CD3 gamma, CD3 delta, CD3 epsilon, CD79a, CD79b, DAP10, and DAP12. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs. Further examples of molecules containing a primary intracellular signaling domain for use in the chimeric receptors disclosed herein include those of DAP10, DAP12, and CD32.

The intracellular signaling domain of the chimeric receptor can comprise the CD3-zeta signaling domain by itself or it can be combined with any other desired intracellular signaling domain(s). For example, the intracellular signaling domain of the chimeric receptor can comprise a CD3 zeta chain portion and a costimulatory signaling domain. The costimulatory signaling domain refers to a portion of the chimeric receptor comprising the intracellular domain of a costimulatory molecule. As used herein, a costimulatory molecule refers to the cognate binding partner on a cell that specifically binds with a costimulatory ligand, thereby mediating a costimulatory response by the cell. Costimulatory molecules are cell surface molecules other than antigen receptors or their ligands that contribute to an efficient immune response. Examples of such costimulatory molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83. Further examples of such costimulatory molecules include CD8, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 id, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

In some embodiments, the signaling domain is from one or more proteins including, without limitation, a receptor tyrosine kinase (RTK), an M-CSF receptor, CSF-1R, Kit, TIE3, an ITAM-containing protein, DAP12, DAP10, an Fc receptor, FcR-gamma, FcR-epsilon, FcR-beta, TCR-zeta, CD3-gamma, CD3-delta, CD3-epsilon, CD3-zeta, CD3-eta, CD5, CD22, CD79a, CD79b, CD66d, TNF-alpha, NF-KappaB, a TLR (toll-like receptor), TLR5, Myd88, target of rapamycin (TOR)/CD3 complex, lymphocyte receptor chain, IL-2 receptor, IgE, IgG, CD16α, FcγRIII, FcγRII, CD28, or 4-1BB. In some embodiments, the signaling domain selected from a 4-1BB intracellular domain, a CD3-zeta ITAM domain, a CD3-zeta intracellular domain, a CSF-1R receptor tyrosine kinase (RTK) intracellular domain, a DAP12 intracellular domain, a TCR-zeta intracellular domain, a TLR5 intracellular domain, a CD28 intracellular domain, a DAP10 intracellular domain, or an FcR-gamma intracellular domain.

Signaling through DAP12 or TCR3Zeta receptor ITAM intracellular domains leads to downstream signaling events such as Syk kinase activation, which promotes survival, functionality, phagocytosis, and proliferation in cells (Turnbull and Colonna, Nat Rev Immunol, 155-161, 2007) (Poliani, Wang et al., J Clin Invest, 2161-2170, 2015) (Wang, Ou j et al., Zhongguo Shi Yan Xue Ye Xue Za Zhi, 568-572, 2015). Major signaling pathways that lead to cell survival are derived from CSF1R and other receptor tyrosine kinase family members such as Kit, the TREM receptor family, and other signaling pathways such as PI3K/AKT. CSF1R and other tyrosine receptor kinase (RTK) activation lead to a pro-survival and proliferation signal for microglia and other immune and/or support cells in the brain, such as astrocytes (Hamilton, Nat Rev Immunol, 533-544, 2008).

The intracellular signaling sequences within the cytoplasmic portion of the chimeric receptor may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences. In one embodiment, a glycine-serine doublet can be used as a suitable linker. In one embodiment, a single amino acid, e.g., an alanine, a glycine, can be used as a suitable linker. In one embodiment, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein.

Two-Component Chimeric Receptors

In some embodiments, a chimeric receptor of the present disclosure can be a two-component receptor. Two-component chimeric receptors include two separate polypeptides that can associate, dimerize, or multimerize through an interaction domain. In some embodiments, the chimeric receptor comprises a heterodimerization domain, such as an inducible heterodimerization domain. This two-component approach allows one component to harbor a ligand binding domain, together with a linker, transmembrane domain, and inducible heterodimerization domain, and the second polypeptide to harbor a transmembrane domain along with signaling domains and an inducible heterodimerization domain. In some embodiments, one or more signaling components can be located on one of the two-components whereas other signaling domains are located on the other component.

The components can be delivered via two lentiviral vectors or by transfection and selection using two selectable markers. In a exemplary embodiment of a two-component receptor system, a host cell contains (e.g., has been transduced with): (1) a vector containing a polynucleotide that encodes an extracellular ligand-binding domain, wherein the ligand is an agent associated with cancer; a flexible linker; a transmembrane domain, and a heterodimerization domain; and (2) a second vector containing a second polynucleotide encoding: a flexible linker, a transmembrane domain, a signaling domain, and a heterodimerization domain. Upon addition of a dimerization-inducing agent, signaling is enhanced due to dimerization or multimerization of both components.

The chimeric receptor can be expressed constitutively after transfer or inducibly to allow for regulation. Induction can be achieved through induced expression using a doxycycline responsive promoter vector or through small molecule-induced receptor dimerization, such as with rapamycin or Rapasyn, a rapamycin analog that is less immunosuppressive. Such an inducible system can allow for limiting the receptor activation period, and/or limiting the location of receptor activation so as to minimize toxicity and maximize dosing. In some embodiments, the inducible heterodimerization domain is a FK506 binding protein (FKBP) heterodimerization domain. In some embodiments, the inducible heterodimerization domain is a T2089L mutant of FKBP-rapamycin binding domain (FRB*) heterodimerization domain.

In another exemplary embodiment of a two-component receptor system, an isolated cell contains (1) a first polynucleotide encoding a chimeric receptor, wherein the chimeric receptor comprises an extracellular ligand-binding domain, wherein the ligand is an agent associated with cancer, a flexible linker, a transmembrane domain, and a heterodimerization domain; and (2) a second polynucleotide encoding a flexible linker, a transmembrane domain, a signaling domains, and a heterodimerization domain. In some embodiments, the ligand-binding domain of the chimeric receptor is a single-chain Fv domain (scFv), the agent associated with cancer of the chimeric receptor is amyloid beta, the flexible linker of the chimeric receptor is a CD8 hinge domain, the transmembrane domain of the chimeric receptor is a CD8 transmembrane domain, and the heterodimerization domain of the chimeric receptor is an inducible FK506 binding protein (FKBP) heterodimerization domain. In some embodiments, the flexible linker encoded by the second polynucleotide is a CSF-1R linker domain, the transmembrane domain encoded by the second polynucleotide is a CSF-1R1 transmembrane domain, the one or more signaling domains encoded by the second polynucleotide are a CSF-1R receptor tyrosine kinase (RTK) intracellular domain and a CD3-zeta ITAM domain, and the heterodimerization domain encoded by the second polynucleotide is an inducible T2089L mutant of FKBP-rapamycin binding domain (FRB*) heterodimerization domain. In some embodiments, the first polynucleotide and the second polynucleotide each encode a polypeptide further comprising a CD8 secretory signal peptide at the N-terminus of the encoded polypeptide. In this example, upon addition of rapamycin, FKBP binds FRB*, resulting in association of the first and second components of the two-component chimeric receptor.

Functional Activities of Chimeric Receptors

In some embodiments, binding of the ligand to the chimeric receptor expressed in an innate immune cell activates the signaling domain, and the activated signaling domain induces and/or enhances one or more activities, including, without limitation, an increase in myeloid cell activation, proliferation, survival, phagocytosis, and/or functionality against pathologies associated with cancer. These activities can include, without limitation, TREM1 or DAP12 phosphorylation; activation of one or more tyrosine kinases; activation of phosphatidylinositol 3-kinase (PI3K); activation of protein kinase B; recruitment of phospholipase C-gamma (PLC-gamma) to a cellular plasma membrane; activation of PLC-gamma; recruitment of TEC-family kinase dVav to a cellular plasma membrane; activation of nuclear factor-kB (NF-kB), inhibition of MAPK signaling; phosphorylation of linker for activation of T cells (LAT) or linker for activation of B cells (LAB); activation of IL-2-induced tyrosine kinase (Itk); modulation of one or more pro-inflammatory mediators; modulation of one or more anti-inflammatory mediators; phosphorylation of extracellular signal-regulated kinase (ERK); modulated expression of C—C chemokine receptor 7 (CCR7); induction of microglial cell chemotaxis toward CCL19 and CCL21 expressing cells; normalization of disrupted ITAM-dependent gene expression; recruitment of Syk, ZAP70, or both to an ITAM complex; increased activity of one or more ITAM-dependent genes or CSF-1R-dependent genes; increased maturation or survival of dendritic cells, monocytes, microglia, M1 microglia, activated M1 microglia, and M2 microglia, macrophages, M1 macrophages, activated M1 macrophages, M2 macrophages, astrocytes, A1 astrocytes, or A2 astrocytes; increased ability of dendritic cells, monocytes, microglia, M1 microglia, activated M1 microglia, and M2 microglia, macrophages, M1 macrophages, activated M1 macrophages, M2 macrophages, astrocytes, A1 astrocytes, or A2 astrocytes, to prime or modulate the function of T cells; enhanced or normalized ability of bone marrow-derived dendritic cells to prime or modulate function of antigen-specific T cells; induction of osteoclast production; increased rate of osteoclastogenesis; increasing phagocytosis by dendritic cells, macrophages, M1 macrophages, activated M1 macrophages, M2 macrophages, monocytes, microglia, M1 microglia, activated M1 microglia, M2 microglia, astrocytes, A1 astrocytes, A2 astrocytes; induction of one or more types of clearance including apoptotic neuron clearance, nerve tissue debris clearance, non-nerve tissue debris clearance, bacteria clearance, other foreign body clearance, disease-causing protein clearance, disease-causing peptide clearance, disease-causing nucleic acid clearance; induction of phagocytosis of one or more of apoptotic neurons, nerve tissue debris, non-nerve tissue debris, dysfunctional synapses, bacteria, other foreign bodies, disease-causing proteins, disease-causing peptides, disease-causing nucleic acids; increased expression of one or more stimulatory molecules; modulated expression of one or more proteins; activation of tumor cell killing; activation of anti-tumor cell proliferation activity; activation of anti-tumor cell metastasis activity; decreased tumor volume or growth rate; and increased efficacy of one or more immune-therapies that modulate anti-tumor T cell responses.

In some embodiments, binding of the ligand to the chimeric receptor expressed in an innate immune cell activates the signaling domain, and the activated signaling domain induces and/or enhances an M1 phenotype in the innate immune cell, secretion of one or more pro-inflammatory cytokines from the innate immune cell, the innate immune cell's activity in inhibiting an immune checkpoint molecule, the innate immune cell's activity in inhibiting myeloid derived suppressor cell (MDSC) s signaling, the innate immune cell's activity in inducing cytotoxic T cell (CTL) activation, the innate immune cell's activity in depressing a T cell, or any combination thereof.

TREM2 and/or DAP12 Phosphorylation

In some embodiments, binding of the ligand to the chimeric receptor expressed in the innate immune cell may induce TREM2 phosphorylation after binding to a TREM2 and/or DAP12 protein expressed by a cell. In other embodiments, binding of the ligand to the chimeric receptor expressed in the innate immune cell may induce DAP12 phosphorylation after binding to a TREM2 and/or DAP12 protein expressed in a cell. In other embodiments, TREM2 and/or DAP12 phosphorylation is induced by one or more SRC family tyrosine kinases. Examples of Src family tyrosine kinases include, without limitation, Src, Yes, Fyn, Fgr, Lck, Hck, Blk, Lyn, and Frk.

DAP12 is variously referred to as TYRO protein tyrosine kinase-binding protein, TYROBP, KARAP, and PLOSL. DAP12 is a transmembrane signaling protein that contains an immunoreceptor tyrosine-based activation motif (ITAM) in its cytoplasmic domain. In certain embodiments, binding of the ligand to the chimeric receptor expressed in the innate immune cell may induce DAP12 phosphorylation in its ITAM motif. Any method known in the art for determining protein phosphorylation, such as DAP12 phosphorylation, may be used.

In some embodiments, DAP12 is phosphorylated by SRC family kinases, resulting in the recruitment and activation of the Syk kinase, ZAP70 kinase, or both, to DAP12. Thus, in certain embodiments, the binding of the ligand to the chimeric receptor expressed in the innate immune cell may recruit Syk, ZAP70, or both to a DAP12/TREM2 complex.

Without wishing to be bound by theory, it is believed that binding of the ligand to the chimeric receptor expressed in the innate immune cell may be useful for preventing, lowering the risk of, or treating conditions and/or diseases associated with decreased levels of DAP12 activity, DAP12 phosphorylation, or recruitment of Syk, ZAP70, or both to a DAP12/TREM2 complex, including cancer.

PI3K Activation

In some embodiments, binding of the ligand to the chimeric receptor expressed in the innate immune cell may induce may induce PI3K activation in a cell.

PI3Ks are a family of related intracellular signal transducer kinases capable of phosphorylating the 3-position hydroxyl group of the inositol ring of phosphatidylinositol (PtdIns). The PI3K family is divided into three different classes (Class I, Class II, and Class III) based on primary structure, regulation, and in vitro lipid substrate specificity.

Activated PI3K produces various 3-phosphorylated phosphoinositides, including without limitation, PtdIns3P, PtdIns (3,4)P2, PtdIns(3,5)P2, and PtdIns(3,4,5)P3. These 3-phosphorylated phosphoinositides function in a mechanism by which signaling proteins are recruited to various cellular membranes. These signaling proteins contain phosphoinositide-binding domains, including without limitation, PX domains, pleckstrin homology domains (PH domains), and FYVE domains. Any method known in the art for determining PI3K activation may be used.

Without wishing to be bound by theory, it is believed that binding of the ligand to the chimeric receptor expressed in the innate immune cell may be beneficial for preventing, lowering the risk of, or treating conditions and/or diseases associated with decreased levels of PI3K activity, including cancer.

Modulated Expression of Anti-Inflammatory Mediators

In some embodiments, binding of the ligand to the chimeric receptor expressed in the innate immune cell may modulate (e.g., increase or decrease) anti-inflammatory activities. In certain embodiments, binding of the ligand to the chimeric receptor expressed in the innate immune cell increases or decreases the expression of anti-inflammatory mediators (e.g., cytokines) and/or modulates the expression of pro-inflammatory mediators.

Inflammation is part of a complex biological response of vascular tissues to harmful stimuli, such as pathogens, damaged cells, and irritants. The classical signs of acute inflammation are pain, heat, redness, swelling, and loss of function. Inflammation is a protective attempt by an organism to remove the injurious stimuli and to initiate the healing process. Inflammation can be classified as either acute inflammation or chronic inflammation. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Chronic inflammation is prolonged inflammation that leads to a progressive shift in the type of cells present at the site of inflammation and is characterized by simultaneous destruction and healing of the tissue from the inflammatory process.

As used herein, anti-inflammatory mediators are proteins involved either directly or indirectly (e.g., by way of an anti-inflammatory signaling pathway) in a mechanism that reduces, inhibits, or inactivates an inflammatory response. Any method known in the art for identifying and characterizing anti-inflammatory mediators may be used. Examples of anti-inflammatory mediators include, without limitation, cytokines, such as IL-4, IL-10, TGF-β, IL-13, IL-35, IL-16, IFN-α, IL-1Rα, VEGF, G-CSF, soluble receptors for TNF, and soluble receptors for IL-6.

In some embodiments, binding of the ligand to the chimeric receptor expressed in the innate immune cell may modulate expression of anti-inflammatory mediators, such as IL-4, IL-10, TGF-β, IL-13, IL-35, IL-16, IFN-α, IL-1Rα, VEGF, G-CSF, soluble receptors for TNF, and soluble receptors for IL-6. In certain embodiments, modulated expression of the anti-inflammatory mediators occurs in macrophages, dendritic cells, and/or microglial cells. Modulated expression may include, without limitation, modulated in gene expression, modulated transcriptional expression, or modulated protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

As used herein, an anti-inflammatory mediator may have increased expression if its expression in one or more cells expressing a chimeric receptor of the present disclosure is greater than the expression of the same anti-inflammatory mediator expressed in one or more cells that is not expressing a chimeric receptor. In some embodiments, binding of the ligand to the chimeric receptor expressed in the innate immune cell may increase anti-inflammatory mediator expression in one or more cells by at least 10%, at least 50%, at least 100%, or at least 200% for example, as compared to anti-inflammatory mediator expression in one or more cells that does not express a chimeric receptor. In other embodiments, binding of the ligand to the chimeric receptor expressed in the innate immune cell increases anti-inflammatory mediator expression in one or more cells by at least 1.5 fold, at least 2.0 fold, or at least 10 fold, for example, as compared to anti-inflammatory mediator expression in one or more cells that does not express a chimeric receptor.

As used herein, an anti-inflammatory mediator may have decreased expression if its expression in one or more cells expressing a chimeric receptor of the present disclosure is less than the expression of the same anti-inflammatory mediator expressed in one or more cells that is not expressing a chimeric receptor. In some embodiments, binding of the ligand to the chimeric receptor expressed in the innate immune cell may decrease anti-inflammatory mediator expression in one or more cells by at least 10%, at least 50%, at least 100%, or at least 200% for example, as compared to anti-inflammatory mediator expression in one or more cells that does not express a chimeric receptor. In other embodiments, binding of the ligand to the chimeric receptor expressed in the innate immune cell decreases anti-inflammatory mediator expression in one or more cells by at least 1.5 fold, at least 2.0 fold, or at least 10 fold, for example, as compared to anti-inflammatory mediator expression in one or more cells that does not express a chimeric receptor.

Without wishing to be bound by theory, it is believed that, in some embodiments, binding of the ligand to the chimeric receptor expressed in the innate immune cell is useful for preventing, lowering the risk of, or treating conditions and/or diseases associated with decreased or increased levels of one or more anti-inflammatory mediators, including cancer.

Modulated Expression of Pro-Inflammatory Mediators

In some embodiments, binding of the ligand to the chimeric receptor expressed in the innate immune cell may modulate (e.g., increase or decrease) the expression of pro-inflammatory mediators in a cell.

As used herein, pro-inflammatory mediators are proteins involved either directly or indirectly (e.g., by way of pro-inflammatory signaling pathways) in a mechanism that induces, activates, promotes, or otherwise increases an inflammatory response. Any method known in the art for identifying and characterizing pro-inflammatory mediators may be used. Examples of pro-inflammatory mediators include, without limitation, cytokines, such as IFN-γ, IL-1α, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, and MCP-1.

In some embodiments, binding of the ligand to the chimeric receptor expressed in the innate immune cell may modulate functional expression and/or secretion of pro-inflammatory mediators, such as IFN-γ, IL-1α, IL-1β, TNF-α, IL-6, IL-8, CRP, IL-20 family members, IL-33, LW, IFN-gamma, OSM, CNTF, GM-CSF, IL-11, IL-12, IL-17, IL-18, IL-23, CXCL10, and MCP-1. In certain embodiments, modulated expression of the pro-inflammatory mediators occurs in macrophages, dendritic cells, monocytes, osteoclasts, Langerhans cells of skin, Kupffer cells, and/or microglial cells. Modulated expression may include, without limitation, modulated gene expression, modulated transcriptional expression, or modulated protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

In certain embodiments, pro-inflammatory mediators include inflammatory cytokines. Accordingly, in certain embodiments, binding of the ligand to the chimeric receptor expressed in the innate immune cell may reduce secretion of one or more inflammatory cytokines. Examples of inflammatory cytokines whose secretion may be modulated by binding of the ligand to the chimeric receptor expressed in the innate immune cell may include, without limitation, IFN-γ, IL-1α, IL-1β, TNF-α, IL-6, IL-8, CRP, IL-20 family members, IL-33, LW, IFN-gamma, OSM, CNTF, GM-CSF, IL-11, IL-12, IL-17, IL-18, IL-23, CXCL10, MCP-1.

As used herein, a pro-inflammatory mediator may have increased expression if its expression in one or more cells of a subject expressing a chimeric receptor of the present disclosure is higher than the expression of the same pro-inflammatory mediator expressed in one or more cells that does not express a chimeric receptor. In some embodiments, the binding of the ligand to the chimeric receptor expressed in the innate immune cell may increase pro-inflammatory mediator expression in one or more cells by at least 10%, at least 50%, at least 100%, or at least 200% for example, as compared to pro-inflammatory mediator expression in one or more cells that does not express a chimeric receptor. In other embodiments, binding of the ligand to the chimeric receptor expressed in the innate immune cell may increase pro-inflammatory mediator expression in one or more cells by at least at least 1.5 fold, at least 2.0 fold, or at least 10 fold, for example, as compared to pro-inflammatory mediator expression in one or more cells that does not express a chimeric receptor.

As used herein, a pro-inflammatory mediator may have decreased expression if its expression in one or more cells of a subject expressing a chimeric receptor of the present disclosure is less than the expression of the same pro-inflammatory mediator expressed in one or more cells that does not express a chimeric receptor. In some embodiments, the binding of the ligand to the chimeric receptor expressed in the innate immune cell may decrease pro-inflammatory mediator expression in one or more cells by at least 10%, at least 50%, at least 100%, or at least 200% for example, as compared to pro-inflammatory mediator expression in one or more cells that does not express a chimeric receptor. In other embodiments, binding of the ligand to the chimeric receptor expressed in the innate immune cell may decrease pro-inflammatory mediator expression in one or more cells by at least at least 1.5 fold, at least 2.0 fold, or at least 10 fold, for example, as compared to pro-inflammatory mediator expression in one or more cells that does not express a chimeric receptor.

Without wishing to be bound by theory, it is believed that binding of the ligand to the chimeric receptor expressed in the innate immune cell may be useful for preventing, lowering the risk of, or treating conditions and/or diseases associated with increased levels of one or more pro-inflammatory mediators, including cancer.

ERK Phosphorylation

In some embodiments, binding of the ligand to the chimeric receptor expressed in the innate immune cell may induce extracellular signal-regulated kinase (ERK) phosphorylation.

Extracellular-signal-regulated kinases (ERKs) are widely expressed protein kinase intracellular signaling kinases that are involved in, for example, the regulation of meiosis, mitosis, and postmitotic functions in differentiated cells. Various stimuli, such as growth factors, cytokines, virus infection, ligands for heterotrimeric G protein-coupled receptors, transforming agents, and carcinogens, activate ERK pathways. Phosphorylation of ERKs leads to the activation of their kinase activity.

Without wishing to be bound by theory, it is believed that binding of the ligand to the chimeric receptor expressed in the innate immune cell is beneficial for preventing, lowering the risk of, or treating conditions and/or diseases associated with decreased levels of ERK phosphorylation, including cancer.

Modulated Expression of C—C Chemokine Receptor 7

In some embodiments, binding of the ligand to the chimeric receptor expressed in the innate immune cell may modulate expression of C—C chemokine receptor 7 (CCR7). Modulated expression may include, without limitation, modulated gene expression, modulated transcriptional expression, or modulated protein expression. Any method known in the art for determining gene, transcript (e.g., mRNA), and/or protein expression may be used. For example, Northern blot analysis may be used to determine gene expression levels, RT-PCR may be used to determine the level of transcription, and Western blot analysis may be used to determine protein levels.

C—C chemokine receptor 7 (CCR7) is a member of the G protein-coupled receptor family. CCR7 is expressed in various lymphoid tissues and can activate B-cells and T-cells. In some embodiments, CCR7 may modulate the migration of memory T-cells to secondary lymphoid organs, such as lymph nodes. In other embodiments, CCR7 may stimulate dendritic cell maturation. CCR7 is a receptor protein that can bind the chemokine (C—C motif) ligands CCL19/ELC and CCL21.

As used herein, CCR7 may have increased expression if its expression in one or more cells expressing a chimeric receptor of the present disclosure is greater than the expression of CCR7 expressed in one or more cells that does not express a chimeric receptor. In some embodiments, binding of the ligand to the chimeric receptor expressed in the innate immune cell may increase CCR7 expression in one or more cells by at least 10%, at least 50%, at least 100%, or at least 200% for example, as compared to CCR7 expression in one or more cells that does not express a chimeric receptor. In other embodiments, binding of the ligand to the chimeric receptor expressed in the innate immune cell increases CCR7 expression in one or more cells by at least 1.5 fold, at least 2.0 fold, or at least 10 fold, for example, as compared to CCR7 expression in one or more cells that does not express a chimeric receptor.

As used herein, CCR7 may have decreased expression if its expression in one or more cells expressing a chimeric receptor of the present disclosure is lower than the expression of CCR7 expressed in one or more cells that does not express a chimeric receptor. In some embodiments, binding of the ligand to the chimeric receptor expressed in the innate immune cell may decrease CCR7 expression in one or more cells by at least 10%, at least 50%, at least 100%, or at least 200% for example, as compared to CCR7 expression in one or more cells that does not express a chimeric receptor. In other embodiments, binding of the ligand to the chimeric receptor expressed in the innate immune cell decreases CCR7 expression in one or more cells by at least 1.5 fold, at least 2.0 fold, or at least 10 fold, for example, as compared to CCR7 expression in one or more cells that does not express a chimeric receptor.

In some embodiments, modulated expression of CCR7 occurs in macrophages, dendritic cells, and/or microglial cells. Increased expression of CCR7 may induce microglial cell chemotaxis toward cells expressing the chemokines CCL19 and CCL21. Accordingly, in certain embodiments, binding of the ligand to the chimeric receptor expressed in the innate immune cell may induce microglial cell chemotaxis toward CCL19 and CCL21 expressing cells.

Without wishing to be bound by theory, it is believed that, in some embodiments, binding of the ligand to the chimeric receptor expressed in the innate immune cell is useful for preventing, lowering the risk of, or treating conditions and/or diseases associated with decreased levels of CCR7, including cancer.

Enhanced Ability or Normalized Ability of Cells to Prime or Modulate Function of Antigen-Specific T Cells In some embodiments, binding of the ligand to the chimeric receptor expressed in the innate immune cell may enhance and/or normalize the ability of dendritic cells (e.g., bone marrow-derived dendritic cells), monocytes, microglia, M1 microglia, activated M1 microglia, and M2 microglia, macrophages, M1 macrophages, activated M1 macrophages, M2 macrophages, astrocytes, A1 astrocytes, A2 astrocytes to prime or modulate antigen-specific T-cells. T cell priming occurs upon first contact of a T cell with its specific antigen. T cell priming involves antigen uptake, processing, and cell surface expression bound to class II MHC molecules by an antigen presenting cell such as a dendritic cell, recirculation and antigen-specific trapping of helper T cell precursors in lymphoid tissue. T cell priming subsequently results in proliferation and differentiation of naïve T cells into effector T cells. In some embodiments, binding of the ligand to the chimeric receptor expressed in the innate immune cell may enhance and/or normalize the ability of bone marrow-derived dendritic cells to induce antigen-specific T-cell proliferation.

In some embodiments, binding of the ligand to the chimeric receptor expressed in the innate immune cell may enhance and/or normalize the ability of dendritic cells (e.g., bone marrow-derived dendritic cells), monocytes, microglia, M1 microglia, activated M1 microglia, and M2 microglia, macrophages, M1 macrophages, activated M1 macrophages, M2 macrophages, astrocytes, A1 astrocytes, A2 astrocytes to induce antigen-specific T-cell proliferation by at least 10%, at least 50%, at least 100%, or at least 200% for example, as compared to the ability of cells that do not contain a chimeric antigen receptor to induce antigen-specific T-cell proliferation. In other embodiments, binding of the ligand to the chimeric receptor expressed in the innate immune cell may enhance and/or normalize the ability of dendritic cells (e.g., bone marrow-derived dendritic cells), monocytes, microglia, M1 microglia, activated M1 microglia, and M2 microglia, macrophages, M1 macrophages, activated M1 macrophages, M2 macrophages, astrocytes, A1 astrocytes, A2 astrocytes to induce antigen-specific T-cell proliferation by at least at least 1.5 fold, at least 2.0 fold, or at least 10 fold, for example, as compared to the ability of cells that do not contain a chimeric receptor to induce antigen-specific T-cell proliferation.

Without wishing to be bound by theory, it is believed that binding of the ligand to the chimeric receptor expressed in the innate immune cell is beneficial for preventing, lowering the risk of, or treating conditions and/or diseases associated with an decreased or dysregulated ability of dendritic cells (e.g., bone marrow-derived dendritic cells), monocytes, microglia, M1 microglia, activated M1 microglia, and M2 microglia, macrophages, M1 macrophages, activated M1 macrophages, M2 macrophages, astrocytes, A1 astrocytes, A2 astrocytes to prime or modulate function of antigen-specific T cells, including cancer.

Osteoclast Production and Osteoclastogenesis

In some embodiments, binding of the ligand to the chimeric receptor expressed in the innate immune cell may induce osteoclast production and/or increase the rate of osteoclastogenesis.

As used herein, an osteoclast is a type of bone cell that can remove bone tissue by removing its mineralized matrix and breaking up the organic bone (e.g., bone resorption). Osteoclasts can be formed by the fusion of cells of the monocyte-macrophage cell line. In some embodiments, osteoclasts may be characterized by high expression of tartrate resistant acid phosphatase (TRAP) and cathepsin K.

As used herein, the rate of osteoclast production or osteoclastogenesis may be increased if the rate of osteoclast production or osteoclastogenesis in a subject treated with chimer receptor-expressing cells of the present disclosure is greater than the rate of osteoclast production or osteoclastogenesis in a corresponding subject that is not treated with chimeric receptor-expressing cells. In some embodiments, binding of the ligand to the chimeric receptor expressed in the innate immune cell may increase the rate of osteoclastogenesis in a subject by at least 10%, at least 50%, at least 100%, or at least 200% for example, as compared to rate of osteoclast production or osteoclastogenesis in a corresponding subject that is not treated with chimeric receptor-expressing cells. In other embodiments, binding of the ligand to the chimeric receptor expressed in the innate immune cell may increase the rate of osteoclast production or osteoclastogenesis in a subject by at least 1.5 fold, at least 2.0 fold, or at least 10 fold, for example, as compared to rate of osteoclast production or osteoclastogenesis in a corresponding subject that is not treated with chimeric receptor-expressing cells.

Without wishing to be bound by theory, it is believed that binding of the ligand to the chimeric receptor expressed in the innate immune cell is beneficial for preventing, lowering the risk of, or treating conditions and/or diseases associated with a reduction in osteoclast production and/or the rate of osteoclastogenesis, including cancer.

Function, Maturation, and Survival of Macrophages, Microglial Cells, Dendritic Cells Monocytes, Astrocytes, Osteoclasts, Langerhans Cells of Skin, and Kupffer Cells In some embodiments, binding of the ligand to the chimeric receptor expressed in the innate immune cell may increase the function, maturation, survival, and/or function of dendritic cells, macrophages, M1 macrophages, activated M1 macrophages, M2 macrophages, monocytes, osteoclasts, Langerhans cells, Kupffer cells, microglia, M1 microglia, activated M1 microglia, M2 microglia, astrocytes, A1 astrocytes, and A2 astrocytes.

In some embodiments, binding of the ligand to the chimeric receptor expressed in the innate immune cell may increase the expression of one or more stimulatory molecules selected from CD83, CD86, MHC class II, and CD40 on macrophages, microglial cells, dendritic cells monocytes, astrocytes, osteoclasts, Langerhans cells of skin, and Kupffer cells.

As used herein, the function, maturation, survival, and/or function of macrophages, microglial cells, dendritic cells monocytes, astrocytes, osteoclasts, Langerhans cells of skin, and Kupffer cells may include increased proliferation, maturation, survival, and/or function of macrophages, microglial cells, dendritic cells monocytes, astrocytes, osteoclasts, Langerhans cells of skin, and Kupffer cells in a subject treated with chimeric receptor-expressing cells of the present disclosure compared to the level of proliferation, maturation, survival, and/or function of macrophages, microglia, dendritic cells monocytes, osteoclasts, Langerhans cells of skin, and/or Kupffer cells in a corresponding subject that is not treated with the chimeric receptor-expressing cells. In some embodiments, binding of the ligand to the chimeric receptor expressed in the innate immune cell may increase proliferation, maturation, survival, and/or function of macrophages, microglial cells, dendritic cells monocytes, astrocytes, osteoclasts, Langerhans cells of skin, and Kupffer cells in a subject by at least 10%, at least 50%, at least 100%, or at least 200% for example, as compared to the proliferation, maturation, survival, and/or function of macrophages, microglial cells, dendritic cells monocytes, astrocytes, osteoclasts, Langerhans cells of skin, and Kupffer cells in a corresponding subject that is not treated with the chimeric receptor-expressing cells. In other embodiments, binding of the ligand to the chimeric receptor expressed in the innate immune cell may increase proliferation, maturation, survival, and/or function of macrophages, microglial cells, dendritic cells monocytes, astrocytes, osteoclasts, Langerhans cells of skin, and Kupffer cells in a subject by at least 1.5 fold, at least 2.0 fold, or at least 10 fold, for example, as compared to the proliferation, maturation, survival, and/or function of macrophages, microglial cells, dendritic cells monocytes, astrocytes, osteoclasts, Langerhans cells of skin, and Kupffer cells in a corresponding subject that is not treated with chimeric receptor-expressing cells.

Without wishing to be bound by theory, it is believed that binding of the ligand to the chimeric receptor expressed in the innate immune cell is beneficial for preventing, lowering the risk of, or treating conditions and/or diseases associated with a reduction in proliferation, maturation, survival, and/or function of macrophages, microglial cells, dendritic cells monocytes, astrocytes, osteoclasts, Langerhans cells of skin, and Kupffer cells, including cancer.

Clearance and Phagocytosis

In some embodiments, binding of the ligand to the chimeric receptor expressed in the innate immune cell may induce clearance and/or phagocytosis of one or more agents associated with cancer. Exemplary agents that may be phagocytosed or cleared include, without limitation, an apoptotic neuron, nerve tissue debris, non-nerve tissue debris, bacteria, other foreign body, disease-causing protein, disease-causing peptide, and disease-causing nucleic acid. Disease causing proteins include amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, and Repeat-associated non-ATG (RAN) translation products. Disease-causing peptides include DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. An exemplary disease-causing nucleic acid is antisense GGCCCC (G2C4) repeat-expansion RNA.

In some embodiments, binding of the ligand to the chimeric receptor expressed in the innate immune cell may induce phagocytosis of one or more of apoptotic neurons, nerve tissue debris, non-nerve tissue debris, bacteria, other foreign bodies, disease-causing proteins, disease-causing peptides, or disease-causing nucleic acid.

In some embodiments, phagocytosis by dendritic cells, macrophages, M1 macrophages, activated M1 macrophages, M2 macrophages, monocytes, microglia, M1 microglia, activated M1 microglia, M2 microglia, astrocytes, A1 astrocytes, or A2 astrocytes is increased. In some embodiments, binding of the ligand to the chimeric receptor expressed in the innate immune cell may increase phagocytosis by macrophages, dendritic cells, monocytes, and/or microglia under conditions of reduced levels of macrophage colony-stimulating factor (MCSF). Alternatively, in some embodiments, binding of the ligand to the chimeric receptor expressed in the innate immune cell may decrease phagocytosis by macrophages, dendritic cells, monocytes, and/or microglia in the presence of normal levels of macrophage colony-stimulating factor (MCSF).

Without wishing to be bound by theory, it is believed that binding of the ligand to the chimeric receptor expressed in the innate immune cell is beneficial for preventing, lowering the risk of, or treating conditions and/or diseases associated with apoptotic neurons, nerve tissue debris of the nervous system, non-nerve tissue debris of the nervous system, bacteria, other foreign bodies, or disease-causing proteins, including cancer.

Kinase Activation and Phosphorylation

In some embodiments, binding of the ligand to the chimeric receptor expressed in the innate immune cell may induce activation or phosphorylation of one or more kinases (e.g., tyrosine kinase, spleen tyrosine kinase (Syk), protein kinase B, or IL-2-induced tyrosine kinase (Itk)).

Spleen tyrosine kinase (Syk) is an intracellular signaling molecule that functions downstream of TREM2 by phosphorylating several substrates, thereby facilitating the formation of a signaling complex leading to cellular activation and inflammatory processes.

Protein kinase B is a serine/threonine-specific protein kinase that plays a key role in multiple cellular processes such as glucose metabolism, apoptosis, cell proliferation, transcription and cell migration.

Itk is an intracellular tyrosine kinase expressed in T-cells. Itk may play a role in T-cell proliferation, differentiation, and the development and effector function of Th2 and Th17 cells.

Without wishing to be bound by theory, it is believed that binding of the ligand to the chimeric receptor expressed in the innate immune cell is beneficial for preventing, lowering the risk of, or treating conditions and/or diseases associated with decreased levels of kinase activation and phosphorylation, including cancer.

Modulated Expression of Proteins

In some embodiments, binding of the ligand to the chimeric receptor expressed in the innate immune cell may modulate expression of C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF. Modulated expression may include, without limitation, modulated gene expression, modulated transcriptional expression, or modulated protein expression. Any method known in the art for determining gene, transcript (e.g., mRNA), and/or protein expression may be used. For example, Northern blot analysis may be used to determine gene expression levels, RT-PCR may be used to determine the level of transcription, and Western blot analysis may be used to determine protein levels.

As used herein, C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF may have increased expression if its expression in one or more cells expressing a chimeric receptor of the present disclosure is greater than the expression of C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expressed in one or more cells that does not express a chimeric receptor. In some embodiments, binding of the ligand to the chimeric receptor expressed in the innate immune cell may increase C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells by at least 10%, at least 50%, at least 100%, or at least 200% for example, as compared to C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells that does not express a chimeric receptor. In other embodiments, binding of the ligand to the chimeric receptor expressed in the innate immune cell increases C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells by at least 1.5 fold, at least 2.0 fold, or at least 10 fold, for example, as compared to C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOXSAP, ITGAM, SLC7A7, CD4, ITGAX, PYCARD, or VEGF expression in one or more cells that does not express a chimeric receptor.

As used herein, C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOXSAP, ITGAM, SLC7A7, CD4, ITGAX, PYCARD, or VEGF may have decreased expression if its expression in one or more cells expressing a chimeric receptor of the present disclosure is lower than the expression of C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expressed in one or more cells that does not express a chimeric receptor. In some embodiments, binding of the ligand to the chimeric receptor expressed in the innate immune cell may decrease C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells by at least 10%, at least 50%, at least 100%, or at least 200% for example, as compared to C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells that does not express a chimeric receptor. In other embodiments, binding of the ligand to the chimeric receptor expressed in the innate immune cell decreases C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells by at least 1.5 fold, at least 2.0 fold, or at least 10 fold, for example, as compared to C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF expression in one or more cells that does not express a chimeric receptor.

In some embodiments, modulated expression of C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF occurs in macrophages, dendritic cells, and/or microglial cells.

Without wishing to be bound by theory, it is believed that, in some embodiments, binding of the ligand to the chimeric receptor expressed in the innate immune cell is useful for preventing, lowering the risk of, or treating conditions and/or diseases associated with dysregulated levels of C1QA, C1QB, C1QC, C1S, C1R, C4, C2, C3, ITGB2, HMOX1, LAT2, CASP1, CSTA, VSIG4, MS4A4A, C3AR1, GPX1, TYROBP, ALOX5AP, ITGAM, SLC7A7, CD4, ITGAX, PYCARD, or VEGF, including cancer.

Recruitment of Signaling Components

In some embodiments, binding of the ligand to the chimeric receptor expressed in the innate immune cell may modulate recruitment of signaling components. In some embodiments the modulated signaling involves recruitment of phospholipase C-gamma (PLC-gamma) to a cellular plasma membrane and subsequent activation of PLC-gamma, recruitment of TEC-family kinase dVav to a cellular plasma membrane, or recruitment of Syk and/or ZAP70 to an ITAM complex. In some embodiments, recruitment to the plasma membrane results in enhanced signaling and increased downstream effector functions.

PLC is a class of membrane-associated enzymes that cleave phospholipids at a point before a phosphate group and are involved in signal transduction pathways. PLC-gamma catalyzes the formation of inositol 1,4,5-trisphosphate and diacylglycerol from phosphatidylinositol 4,5-bisphosphate. This reaction uses calcium as a cofactor and plays an important role in the intracellular transduction of receptor-mediated tyrosine kinase activators.

TEC family kinases are involved in the intracellular signaling mechanisms of cytokine receptors, lymphocyte surface antigens, heterotrimeric G-protein-coupled receptors, and integrin molecules.

ZAP70, a protein-tyrosine kinase, is part of the TCR and plays an important role in T-cell signaling. Upon phosphorylation of ITAMs during intracellular signaling, ZAP-70 is able to bind to CD3-zeta. The tandem SH2-domains of ZAP-70 are engaged by the doubly phosphorylated ITAMs of CD3-zeta, which positions ZAP-70 to phosphorylate the transmembrane protein linker of activated T cells (LAT). Phosphorylated LAT, in turn, serves as a docking site to which a number of downstream signaling proteins bind.

Without wishing to be bound by theory, it is believed that, in some embodiments, binding of the ligand to the chimeric receptor expressed in the innate immune cell is useful for preventing, lowering the risk of, or treating conditions and/or diseases associated with dysregulated recruitment of signaling pathway components, including cancer.

Inhibition of MAPK Signaling

In some embodiments, binding of the ligand to the chimeric receptor expressed in the innate immune cell may inhibit MAPK signaling in a cell.

MAPK, or mitogen-activated protein kinases, are serine/threonine protein kinases that are involved in propagating signaling pathways directing cellular responses such as cell proliferation, differentiation, and survival. MAPKs are catalytically inactive in their base form, and require phosphorylation in their activation loops to become activated. Mitogens, cytokines, and cellular stresses promote the activation of different MAPK pathways, which in turn phosphorylate and activate downstream signaling mediators.

Inhibited signaling may include, without limitation, decreased gene expression, decreased transcriptional expression, or decreased protein expression. Any method known in the art for determining gene, transcript (e.g., mRNA), and/or protein expression may be used. For example, Northern blot analysis may be used to determine gene expression levels, RT-PCR may be used to determine the level of transcription, and Western blot analysis may be used to determine protein levels.

Without wishing to be bound by theory, it is believed that, in some embodiments, binding of the ligand to the chimeric receptor expressed in the innate immune cell is useful for preventing, lowering the risk of, or treating conditions and/or diseases associated with dysregulated MAPK signaling, including cancer.

Phosphorylation of Linker for Activation of T Cells (LAT) or Linker for Activation of B Cells (LAB)

In some embodiments, binding of the ligand to the chimeric receptor expressed in the innate immune cell may modulate phosphorylation of LAT or LAB in a cell.

LAT is phosphorylated by ZAP70/Syk protein tyrosine kinases following activation of the TCR signal transduction pathway. LAT localizes to lipid rafts (also known as glycosphingolipid-enriched microdomains or GEMs) and acts as a docking site for SH2 domain-containing proteins. Upon phosphorylation, LAT recruits multiple adaptor proteins and downstream signaling molecules into multimolecular signaling complexes.

LAB, also known as non-T-cell activation linker (NTAL), is expressed in B cells, NK cells, monocytes, and mast cells. NTAL becomes rapidly tyrosine-phosphorylated upon cross-linking of the B cell receptor (BCR) or of high-affinity Fcγ- and Fcε-receptors of myeloid cells and subsequently associates with cytoplasmic signaling molecules. In addition, LAB is required for TREM-2-mediated activation of Erk1/2 and modulates proximal TREM-2 signals, resulting in macrophages with proinflammatory properties.

Without wishing to be bound by theory, it is believed that, in some embodiments, binding of the ligand to the chimeric receptor expressed in the innate immune cell is useful for preventing, lowering the risk of, or treating conditions and/or diseases associated with dysregulated LAT or LAB phosphorylation, including cancer.

Modulated Activity of ITAM-Dependent Genes or CSF-1R-Dependent Genes

In some embodiments, binding of the ligand to the chimeric receptor expressed in the innate immune cell may modulate activity of ITAM-dependent or CSF-1R-dependent genes in a cell. hi some embodiments, binding of the ligand to the chimeric receptor expressed in the innate immune cell may modulate ITAM-dependent and/or CSF-1R-dependent gene expression. Suitable ITAM-dependent and CSF-1R-dependent genes that can be modified include, without limitation, PDL-1, PDL-2, ICOS, B7-H3, B7-H4, OX40L, FOXP3, IDO, CD39, CD73, CD80, CD86, CD83, CD11b, CD14, CD33, Siglec-5, Siglec-7, Siglec-9, IFN-gamma, IFN-alpha, IFN-beta, IL-18, IL-12, IL-10, IL-6, IL-2, IL-1 (beta and alpha), TNF-alpha, TGF-beta, IRF1, IRF3, STAT1, STAT3, HIF1-alpha, GMZA, GMZB, GZMH, PRF1, GNLY, CXCL9, CXCL10, CCL5, CX3CL1, CCL2, MADCAM1, ICAM1, VCAM1, VEGF, GMCSF, MCSF, Slc7a2, Cxc19, Serpinb2, Ptgs2, Cxc13, Cd38, Arg1, Mgl2, Retnla, Earl 1, Tmem26, Mrc1, Socs2, Ch25h, Chi313, Slc17a2, Fltl, TIM3, LAG3, CD137, GAL9, OX40, GITR, Osteopontin, MID1, AXL, ITGAX, LPL, SPP1, ATP6VoD2, SIGLECH, CD33, TMEM119, EMR1, CDH23, GLO1, and RASGRF2. ITAM-dependent genes that may be modulated (i.e., upregulated or downregulated) include, without limitation Saa3, Cd38, C1qa, C1u, Cxc110, H2-T10, Cc15, Hpgd, Pyhin1, Emp2, Cx3cr1, Cd86, Abca1, Ifit1, Cc13, Gpr34, Sparc, Cxc19, Cd14, Aoah, Fcgr1, Slfn8, Itga9, Il18, Ebi3, Plxdc2, Edn1, Rasgrp3, Socs3, P2ry13, Aif1, Fam26f, Ccr7, Cp, Ltf, Hp, Ang, Cc14, Mmp9, 116, Arhgap22, Il7r, Actn1, Kctd12, Lgmn, Fcnb, Chst7, Lmna, Cc119, Parvg, Siglech, K1, Adcyap1r1, Psd, Sphk1, Cts1, Hsd11b1, Tmem47, Lag3, Bcar3, Tmem158, Slc7a5, Slc2a5, Gp9, Cxcl11, Flrt2, Vwf, Ccl12, Atp6v0a1, Plk2, Ccnd1, Mmp12, Atf3, Myc, and Egr2. ITAM-dependent and CSF-1R-dependent genes that can be modified in M2 macrophages include, without limitation, ACTN1, AMZ1, ATP6VOA1, ATP6VOD2, BCAR3, CD300LD, CD83, CHST7, CLEC10A, CLEC7A, EGR2, EMP2, FLRT2, GNB4, IL6ST, LMNA, MATK, MMP12, MMP9, MRC1, MYC, OLFM1, P2RY1, PLK2, PTGS1, PTPLA, RHOJ, SOCS6, TANC2, TCFEC, TIAM1, TMEM158, and VWF. ITAM-dependent and CSF-1R-dependent gene that can be modified in M1 macrophages include, without limitation, AOAH, ARHGAP24, CCRL2, CD300LF, CD38, CFB, CP, CPD, CXCL10, D14ERD668E, DDX58, DDX60, E030037K03RIK, EBI3, EPB4.1L3, F11R, FAM176B, FAM26F, FPR1, FPR2, GBP6, GNGT2, GPR18, H2-Q6, H2-T10, HERC6, HP, IFI44, IFIT1, IFIT2, IRAK3, ISF20, ISG15, ITGAL, LOC100503664, MARCO, MPA2L, MS4A4C, MX1, NFKBIZ, OASL1, PILR1, PROBE, PST-PIP2, PYHIN1, RSAD2, SAA3, SEPX1, SLFN1, SLFN4, SLFN8, STAT1, STAT2, TLR2, TUBA4A, XAF1, and ZPB1. CSF-1R-dependent genes that may be modulated (i.e., upregulated or downregulated) include, without limitation Ms4a6b, Mmp12, Selenbp1, Ndrg1, Bnip3, Klk1b11, Selenbp2, AW112010, Rgs17, Bnip3, Mrc1, Scd1, Cxcr4, Ero11, Ms4a7, Scd2, Cyp2ab1, Trib3, Ms4a6c, Plce1, Ms4a4c, Cyp11a1, NA, NA, Tmem71, Earl, Fabp5, Fabp5, 4930583H14Rik, Tcp1112, C3, Mmp13, Ghrh, Prelid2, F10, Ephx1, Lilra5, Aoah, Gpr162, Car6, Il7r, Snhg8, NA, Dkc1, Ccnd2, NA, Tsr1, Adapt, Snhg1, Ptgs2, Txnip, Mmp8, Met, NA, Ppbp, Epha2, Jag1, NA, Cxc13, NA, Cc17, NA, NA, Id3, Cd207, NA, NA, Id1, Tfrc, TREM1, and Cc112.

Without wishing to be bound by theory, it is believed that, in some embodiments, binding of the ligand to the chimeric receptor expressed in the innate immune cell is useful for preventing, lowering the risk of, or treating conditions and/or diseases associated with dysregulated ITAM or CSF-1R signaling pathways, including cancer.

Modulation of Anti-Cancer Responses

In some embodiments, binding of the ligand to the chimeric receptor expressed in the innate immune cell may modulate one or more anti-cancer responses in a subject. In some embodiments, the anti-cancer response is an anti-tumor response. Anti-tumor cell responses may include, without limitation, tumor cell killing, anti-tumor cell proliferation activity, anti-tumor cell metastasis activity, and efficacy of one or more immune-therapies that modulate anti-tumor T cell responses. In some embodiments, binding of the ligand to the chimeric receptor expressed in the innate immune cell increases tumor cell killing, anti-tumor cell proliferation activity, and/or anti-tumor cell metastasis activity mediated by microglia, macrophages, dendritic cells, bone marrow-derived dendritic cells, neutrophils, or any combination thereof. In some embodiments, binding of the ligand to the chimeric receptor expressed in the innate immune cell may reduce tumor volume and/or growth rate. In some embodiments, reduced tumor volume and growth rate, reduced number of tumor infiltrating immune suppressor macrophages, and increased effector T cell influx into the tumor may indicate the anti-cancer effects of chimeric receptor-expressing innate immune cells. Any method known in the art for determining tumor volume or growth rate may be used. For example, tumor volume or growth may be monitored visually, with a caliper, or via imaging methods such as X-ray imaging, CT scans, nuclear imaging (PET scans), ultrasound, magnetic resonance imaging (MRI), digital mammography, and virtual colonoscopy.

In some embodiments, binding of the ligand to the chimeric receptor expressed in the innate immune cell may increase efficacy of one or more immune-therapies that modulate anti-tumor T cell responses in a subject. Exemplary immune-therapies that modulate anti-tumor T cell responses include, without limitation, PD1/PDL1 blockade, CTLA-4 blockade, and cancer vaccines. In some embodiments, a decrease in tumor growth and an increase in percent survival may indicate that chimeric receptor-expressing cells have additive or synergistic therapeutic effects with one or more immune-therapies that modulate anti-tumor T cell responses.

Without wishing to be bound by theory, it is believed that, in some embodiments, binding of the ligand to the chimeric receptor expressed in the innate immune cell is useful for preventing, lowering the risk of, or treating conditions and/or diseases associated with decreased anti-tumor responses, including cancer.

Innate Immune Cell Functionality

In some embodiments, binding of the ligand to the chimeric receptor expressed in an innate immune cell activates the signaling domain, and the activated signaling domain induces and/or enhances one of more functions of the innate immune cell.

In some embodiments, the activated signaling domain induces and/or enhances an M1 phenotype in the innate immune cell. Cells with an M1 phenotype (e.g., M1 macrophages) can produce large amounts of the cytokines TNF, IL-12, and IL-23 and can help drive pro-inflammatory and antigen specific T cell responses. In some embodiments, the activated signaling domain induces and/or enhances the innate immune cell's activity in inhibiting an immune checkpoint molecule. Exemplary immune checkpoint molecules that can be inhibited include, without limitation, programmed death ligand 1 (PD-L1), cytotoxic T-lymphocyte-associated protein 4 (CTLA4), programmed death ligand 2 (PD-L2), programmed cell death protein 1 (PD-1), B7-H3, B7-H4, Herpesvirus entry mediator (HVEM), B- and T-lymphocyte attenuator (BTLA), Killer inhibitory receptor (KIR), galectin 9 (GAL9), T-cell immunoglobulin and mucin-domain containing-3 (TIM3), adenosine receptor Ata (AZAR), LAG-3, phosphatidylserine, CD27, TNF-α, CD33, Sialic acid-binding immunoglobulin-type lectin 5 (Siglec-5), Siglec-7, Siglec-9, Siglec-11, TREM1, and TREM2.

In some embodiments, the activated signaling domain induces and/or enhances the innate immune cell's activity in inhibiting myeloid derived suppressor cell (MDSC) signaling. MDSCs are a heterogeneous group of immune cells that have strong immunosuppressive abilities. MDSCs can suppress the activity and effector function of T cells, DCs, macrophages, and NK cells. MDSCs are also known to accumulate in cancer patients and can impair anti-tumor responses, including the ability of cytotoxic CD8+ T cells to kill cancer cells. In some embodiments, the activated signaling domain induces and/or enhances the innate immune cell's activity in inducing cytotoxic T cell (CTL) activation. CTLs, such as cytotoxic CD8+ T cells, mediate antigen-specific killing of cancerous and virally-infected cells through the release of the cytotoxins perforin, granzymes, and granulysin and through Fas/FasL-mediated apoptosis. In some embodiments, the activated signaling domain induces and/or enhances the innate immune cell's activity in depressing a T cell such as a regulatory T cell. Regulatory T cells (Tregs) can suppress induction and proliferation of effector T cells, and may limit the immune response generated against cancerous cells. Increased numbers of Tregs is associated with a poorer prognosis in several types of cancer, including ovarian, breast, renal, and pancreatic cancer. Thus, without wishing to be bound by theory, suppressing Tregs in the context of cancer may enhance the anti-cancer immune response.

Without wishing to be bound by theory, it is believed that, in some embodiments, binding of the ligand to the chimeric receptor expressed in the innate immune cell is useful for preventing, lowering the risk of, or treating conditions and/or diseases associated with dysregulated innate immune cell functionality, including cancer.

Polynucleotides Encoding Chimeric Receptors

Certain aspects of the present disclosure relate to an isolated polynucleotide encoding a chimeric receptor. The disclosure encompasses a polynucleotide construct comprising sequences of a chimeric receptor, wherein the sequence comprises the nucleic acid sequence of a ligand-binding domain operably linked to the nucleic acid sequence of a transmembrane domain and an intracellular domain. In some embodiments, by fusing a polynucleotide encoding a ligand binding domain to polynucleotides encoding transmembrane and signaling domains, a chimeric gene is obtained which combines a ligand binding site and intracellular signaling components into one continuous chain. In some embodiments the polynucleotide is a DNA polynucleotide. In some embodiments the polynucleotide is a RNA polynucleotide, such as an mRNA polynucleotide.

The polynucleotide sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques.

Alternatively, the polynucleotide of interest can be produced synthetically, rather than cloned.

Several chimeric receptor constructs are described herein, with each utilizing a different combination of ligand-binding, linker, transmembrane, and/or intracellular signaling domains. The chimeric receptors constructs can be used individually or can be used in any combination. The constructs can be introduced into the same cells or can be introduced into a mixed population of cells that express one or the other construct separately. In some embodiments, the chimeric receptors are referred to as synthetic myeloid activating receptor technology (SMART) receptors. Several SMART receptors are described herein. As used herein, the ">>" symbol indicates association between the different chimeric receptor domains. Chimeric receptor domains are listed, in order from 5'→3' of the polynucleotide sequence, as ligand-binding domain, linker, transmembrane domain, and signaling domain, with each domain separated by the ">>" symbol (e.g., ligand-binding domain>>linker>>transmembrane domain>>signaling domain). "SS" as used herein refers to a signal sequence. "TM" as used herein refers to a transmembrane domain.

In some embodiments, the polynucleotide comprises a nucleic acid sequence selected from SEQ ID NOs: 27-33. In some embodiments, the polynucleotide comprises a nucleic acid sequence with at least about 80%, about 85%, about 90%, about 95%, about 96%, about 97%, about 98%, or about 99% homology to the polynucleotide sequence selected from SEQ ID NOs: 27-33. In some embodiments, the chimeric receptor comprises an amino acid sequence selected from SEQ ID NOs: 20-26, or an amino acid sequence with at least about 95% homology to the amino acid sequence of SEQ ID NOs: 20-26. In some embodiments, the chimeric receptor comprises an amino acid sequence with at least about 80%, about 85%, about 90%, about 95%, about 96%, about 97%, about 98%, or about 99% homology to the amino acid sequence of SEQ ID NOs: 20-26. Certain aspects of the present disclosure relate to an isolated chimeric receptor encoded by the polynucleotide comprises a nucleic acid sequence selected from SEQ ID NOs: 27-33.

In some embodiments, the chimeric receptor is SMART1. SMART1 is composed of the elements: CD8 secretory signal sequence (SS)>>anti-CD19 scFv>>CD8 Hinge domain>>CD8 transmembrane domain (TM)>>4-1BB intracellular>>CD3Zeta ITAM domain. The amino acid sequence for SMART1 is provided in SEQ ID NO: 20 and the polynucleotide sequence for SMART1 is provided in SEQ ID NO: 27.

In some embodiments, the chimeric receptor is SMART11. SMART11 is composed of the elements: CD8SS>>antiCD19SCfV>>CD8Hinge>>CD8TM>>
CD28>>CD3Zeta ITAM. The amino acid sequence for SMART11 is provided in SEQ ID NO: 21 and the polynucleotide sequence for SMART11 is provided in SEQ ID NO: 28.

In some embodiments, the chimeric receptor is SMART12. SMART12 is composed of the elements: SMART12 is composed of the elements: CD8 SS>>anti-CD19 SCfV>>CD8 Hinge>>CD8TM>>TLR5 intracellular domain. The amino acid sequence for SMART12 is provided in SEQ ID NO: 22 and the polynucleotide sequence for SMART12 is provided in SEQ ID NO: 29.

In some embodiments, the chimeric receptor is SMART13. SMART13 is composed of the elements: CD8 SS>>anti-CD19SCfV>>TLR5 hinge and transmembrane>>TLR5 intracellular domain. The amino acid sequence for SMART13 is provided in SEQ ID NO: 23 and the polynucleotide sequence for SMART13 is provided in SEQ ID NO: 30.

In some embodiments, the chimeric receptor is SMART14. SMART14 is composed of the elements: CD8 SS>>anti-CD19 SCfV>>CD8 Hinge>>CD8TM>>CD28 intracellular domain>>TLR5 intracellular domain. The amino acid sequence for SMART14 is provided in SEQ ID NO: 24 and the polynucleotide sequence for SMART14 is provided in SEQ ID NO: 31.

In some embodiments, the chimeric receptor is SMART15. SMART15 is composed of the elements: CD8 SS>>anti-CD19 SCfV>>CD8 Hinge>>CD8TM>>4-1BB intracellular domain>>TLR5 intracellular domain. The amino acid sequence for SMART15 is provided in SEQ ID NO: 25 and the polynucleotide sequence for SMART15 is provided in SEQ ID NO: 32.

In some embodiments, the chimeric receptor is SMART16. SMART16 is composed of the elements: CD8 SS>>anti-CD19 SCfV>>TLR5 hinge and transmembrane>>TLR5 intracellular>>CD3zeta intracellular domain. The amino acid sequence for SMART16 is provided in SEQ ID NO: 26 and the polynucleotide sequence for SMART16 is provided in SEQ ID NO: 33.

In some embodiments, the chimeric receptor is a two-component receptor. In some embodiments, the two-component receptor includes a FK506 binding protein (FKBP) heterodimerization domain. An exemplary FKBP sequence is provided in SEQ ID NO: 18. In some embodiments, the inducible heterodimerization domain includes a FKBP-rapamycin binding domain (FRB*) heterodimerization domain. An exemplary FRB* sequence is provided in SEQ ID NO: 19.

In some embodiments, the amino acid sequence of the ligand-binding domain (or other portions or the entire chimeric receptor) can be modified, e.g., an amino acid sequence described herein can be modified, e.g., by a conservative substitution. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Vectors

Certain aspects of the present disclosure relate to a vector comprising a polynucleotide encoding a chimeric receptor. In some embodiments, one or more vectors (e.g., expression vectors) containing such polynucleotides are provided.

For recombinant production of a chimeric receptor of the present disclosure, a polynucleotide encoding the chimeric receptor is isolated and inserted into one or more vectors for further cloning and/or expression in a host cell. Such polynucleotides may be readily isolated and sequenced using conventional procedures (e.g., by using oligonucleotide probes that are capable of binding specifically to genes encoding the chimeric receptor domains).

Suitable vectors containing a polynucleotide encoding a chimeric receptor of the present disclosure include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors generally are replicable polynucleotide constructs that contain a polynucleotide of the present disclosure. The expression vector may replicable in the host cells either as episomes or as an integral part of the chromosomal DNA. Suitable expression vectors include but are not limited to plasmids, viral vectors, including adenoviruses, adeno-associated viruses (AAVs), lentiviral vectors, retroviral vectors, cosmids, a sleeping beauty vector, non-viral plasmid vectors and expression vector(s) disclosed in PCT Publication No. WO 87/04462. In some embodiments, the vector is pCDNA3.4-Topo from Life Technologies.

Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons. In one embodiment, the nucleic acid sequence in the vector further comprises a poly(A) tail. In one embodiment, the nucleic acid sequence in the vector further comprises a 3'UTR e.g., comprising at least one repeat of a 3'UTR derived from human beta-globulin.

In some embodiment, the vector comprises a promoter. Depending on the promoter, individual elements can function either cooperatively or independently to activate transcription. Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another.

Exemplary promoters for use in the present disclosure include, without limitation, the CMV IE gene, EF-1 promoter, ubiquitin C, phosphoglycerokinase (PGK) promoter, T2A promoter, and thymidine kinase (tk) promoter. In some embodiments, the promoter is an EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving chimeric receptor expression from transgenes cloned into a lentiviral vector. See, e.g., Milone et al., Mol. Ther. 17(8): 1453-1464 (2009). Another example of a promoter is the immediate early cytomegalovirus (CMV IE) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Inducible promoters are also contemplated for use in the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Host Cells

Certain aspects of the present disclosure relate to a host cell comprising a chimeric receptor. In some embodiments, a host cell containing a polynucleotide encoding a chimeric receptor is provided. In some embodiments, the host cell is an isolated host cell. As used herein, an "isolated cell" is a cell that is identified and separated from at least one contaminant cell with which it is ordinarily associated in the environment in which it was produced. In some embodiments, the isolated cell is free of association with all components associated with the production environment. The isolated cell is in a form other than in the form or setting in which it is found in nature. Isolated cells are distinguished from cells existing naturally in tissues, organs, or individuals. In some embodiments, the isolated cell is a host cell of the present disclosure. In some embodiments, the host cell contains (e.g., has been transduced with): a vector containing a polynucleotide that encodes an extracellular ligand-binding domain, wherein the ligand is an agent associated with cancer; a flexible linker; a transmembrane domain, and a signaling domain. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells. In some embodiments, a host cell of the present disclosure containing a polynucleotide encoding said chimeric receptor is cultured under conditions suitable for expression of the chimeric receptor.

Immune Cells

In some embodiments, the host cell is an innate immune cell. Any suitable innate immune cell known in the art may be used. Innate immune cells for use in the present disclosure may be in a resting or activated state. For example, in some embodiments, the innate immune cell is a cell that has been activated by the presence of antigen, cytokines, or other activating ligands.

In some embodiments, the innate immune cell is a NK cell. NK (natural killer) cells are innate lymphocytes which are differentiated from the common lymphoid progenitor (CLP). NK cells have diverse functions, including recognizing and killing virally-infected and tumor cells (mediated by the contents of their cytotoxic granules) and secreting cytokines such as IFNγ.

In some embodiments, the innate immune cell is a myeloid cell. Myeloid cells are derived from hematopoietic stem cells in the bone marrow. Myeloid cells include megakaryocytes, erythrocyte-precursors, mononuclear phagocytes (monocytes/macrophages) and all of the polymorphonuclear leukocytes (neutrophils, basophils, eosinophils). Exemplary myeloid cells include, without limitation, macrophages, monocytes, neutrophils, dendritic cells (DCs), osteoclasts, Langerhans cells, Kupffer cells, and microglia.

Monocytes are amoeboid shaped cells with agranulated cytoplasm and unilobar nuclei. Monocytes circulate in the bloodstream and can migrate in response to inflammatory signals. Upon migration from the bloodstream to other tissues, monocytes differentiate into tissue resident macrophages or DCs. Functional activities of monocytes, macrophages, and DCs include, without limitation, phagocytosis, antigen presentation, and cytokine production. Neutrophils, which contain a multilobulated nucleus, are recruited to sites of injury or infection by chemotaxis, and function via phagocytosis, release of soluble anti-microbials, and generation of neutrophil extracellular traps (NETs). Langerhans cells are resident dendritic cells of the skin and mucosa. The have a similar morphology and function as macrophages, including antigen presentation. Kupffer cells, also known as stellate macrophages, are resident macrophages of the liver that play a role in host defense and in the homeosatic responses of tissue. Kupffer cells are found in the hepatic sinusoids and function by endocytosing blood-borne materials which enter the liver. Osteoclasts are bone cells that are involved in the maintenance, repair, and remodeling of bones. Osteoclasts are derived from the myeloid lineage and are formed in the presence of receptor activator of nuclear factor κβ ligand (RANKL) and macrophage colony-stimulating factor (M-CSF) produced by stromal cells and osteoblasts.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most infections from reaching the vulnerable nervous tissue. In the case where infectious agents are directly introduced to the brain or cross the blood-brain barrier, microglial cells must react quickly to decrease inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T-cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

Some aspects of the present disclosure include an isolated myeloid cell comprising a chimeric receptor. In some embodiments, an isolated myeloid cell comprises a first polynucleotide encoding a chimeric receptor, wherein the chimeric receptor comprises an extracellular ligand-binding domain, wherein the ligand is an agent associated with cancer; a flexible linker; a transmembrane domain, and a heterodimerization domain; and a second polynucleotide encoding: a flexible linker, a transmembrane domain, a signaling domains, and a heterodimerization domain. In some embodiments, the ligand-binding domain of the chimeric receptor is a single-chain Fv domain (scFv), the agent associated with cancer of the chimeric receptor is amyloid beta, the flexible linker of the chimeric receptor is a CD8 hinge domain, the transmembrane domain of the chimeric receptor is a CD8 transmembrane domain, and the heterodimerization domain of the chimeric receptor is an inducible FK506 binding protein (FKBP) heterodimerization domain. In some embodiments, the flexible linker encoded by the second polynucleotide is a CSF-1R linker domain, the transmembrane domain encoded by the second polynucleotide is a CSF-1R1 transmembrane domain, the one or more signaling domains encoded by the second polynucleotide are a CSF-1R receptor tyrosine kinase (RTK) intracellular domain and a CD3-zeta ITAM domain, and the heterodimerization domain encoded by the second polynucleotide is an inducible T2089L mutant of FKBP-rapamycin binding domain (FRB*) heterodimerization domain. In some embodiments, the first polynucleotide and the second polynucleotide each encode a polypeptide further comprising a CD8 secretory signal peptide at the N-terminus of the encoded polypeptide.

In some embodiments, the cell phenotype of an isolated myeloid cell expressing a chimeric receptor is modified in vitro, ex vivo, or in vivo by addition of pro-inflammatory or anti-inflammatory agents or cytokines. Such cytokines can include, without limitation, GM-CSF, MCSF, IL-1, IL4, IL10, IL12, TNFα, TGF-beta, and LPS.

In some embodiments, the innate immune cell is an astrocyte. Astrocytes, also called astroglia, are specialized glial cells found in the brain and spinal cord. Astrocytes are derived from heterogeneous populations of progenitor cells in the neuroepithelium of the developing central nervous system. Astrocyte functions include endothelial cell support, regulation of blood flow, synapse function, maintenance of extracellular ion balance, and nervous system repair. Astrocytes also function as immune cells in the CNS via their production of cytokines and expression of class II MHC antigens and costimulatory molecules that are critical for antigen presentation and T-cell activation. Astrocytes are also involved in various neurological diseases, including Alzheimer's disease, amyotrophic lateral sclerosis, Parkinson's disease, and dementia. Early stages of neurological disease processes are thought to be associated with atrophy of astroglia, which causes disruptions in synaptic connectivity and neurotransmitter homeostasis, and neuronal death. At the later stages of disease, astrocytes may become activated and contribute to the neuroinflammatory component of neurological diseases. In some embodiments, the astrocyte is an A1 astrocyte or an A2 astrocyte. A1 astrocytes express the adenosine A1 receptor, while A2 astrocytes express the adenosine A2 receptor. Adenosine receptors have inhibitory functions, including decreasing metabolic activity and reducing synaptic vesicle release during nerve transmission.

In some embodiments, the innate immune cell has an M1 or M2 phenotype. In some embodiments, innate immune cells with an M1 phenotype are involved in inflammatory process and may secrete pro-inflammatory cytokines such as IL-1 and TNFα. In some embodiments, innate immune cells with an M2 phenotype are involved in resolution of inflammation and tissue repair. For example, macrophages can be polarized toward a classically activated (M1) phenotype in the presence of lipopolysaccharide (LPS) and IFNγ. M1 macrophages can produce large amounts of the cytokines TNF, IL-12, and IL-23 and can help drive pro-inflammatory and antigen specific T cell responses. Conversely, macrophages can be polarized toward an alternatively activated (M2) phenotype in the presence of IL-4. M2 macrophages can produce large amounts of the cytokines IL-10 and IL-1RA and function in immunoregulation and tissue remodeling. In some embodiments, the innate immune cell is an M1 macrophage, an M2 macrophage, a neutrophil, an activated neutrophil, an NK cell, an M1 microglia, or an M2 microglia.

In some embodiments, genetic manipulation of cells encoding chimeric receptors can allow polarization of cells in a directed manner. For example, cells can be polarized toward a protective/regenerative M2-like phenotype or an M1-like pro-inflammatory state through inhibition of components of the NFKappaB complex pathway (e.g., IKK). In some embodiments, the isolated host cell further expresses one or more signaling factors that promote an M2 phenotype by inhibiting a TNF-alpha/NF-KappaB pathway a TLR/MyD88 pathway, or both. Such signaling factors can include, without limitation, dominant negative IKK-alpha, a dominant negative IKK-alpha IKK-beta, a dominant negative IKK-alpha IKBa (IKBa-DN), a MEKK isoform, and any combination thereof. hi some embodiments, the one or more signaling factors that promote an M2 phenotype by inhibiting a TLR/MyD88 pathway are one or more dominant negative forms of MyD88.

Methods of Producing Chimeric Receptor-Expressing Cells

Certain aspects of the present disclosure include a method of producing an innate immune cell expressing a chimeric receptor. The vectors containing the polynucleotides encoding a chimeric receptor can be introduced into a host cell by any of a number of appropriate means. Vectors can be transferred to a host cell in vitro, ex vivo, or in vivo. For example, the expression vector can be transferred into a host cell by physical, chemical, or biological means. The choice of introducing vectors or polynucleotides will often depend on features of the host cell.

Physical methods for introduction include calcium phosphate precipitation, lipofection, particle bombardment, microinjection, and electroporation, and the like. Methods for producing cells comprising vectors and/or exogenous nucleic acids are well-known in the art. In some embodiments, the polynucleotide is introduced into a host cell by calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the polynucleotides or vectors into a host cell (in vitro, ex vivo or in vivo). In another aspect, the polynucleotide may be associated with a lipid. The polynucleotide or vector associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce polynucleotides into a host cell, in order to confirm the presence of the polynucleotide in the host cell, a variety of assays may be performed. Such assays include, for example, "molecular biological" assays well known to those of skill in the art, such as Southern and Northern blotting, RT-PCR and PCR;

Or "biochemical" assays, such as detecting the presence or absence of a particular peptide, e.g., by immunological means (ELISAs and Western blots).

In some embodiments, an innate immune cell expressing a chimeric receptor is produced by isolating an innate immune cell, introducing a vector encoding a chimeric receptor, and culturing the cell so that the chimeric receptor is expressed. In some embodiments, vector constructs expressing a chimeric receptor can be directly transduced into a cell. In some embodiments, an RNA construct encoding a chimeric receptor can be directly transfected into a cell. Upon transfection or transduction of such chimeric receptor-encoding polynucleotides into immune cells, the construct is expressed in the cell as a functional receptor and endows the cells with ligand specificity.

Allogeneic Cells

In some embodiments, the innate immune cell is an allogeneic cell. In some embodiments, the innate immune cell is modified to be an allogeneic cell. In some embodiments, the innate immune cell may be modified to lack one or more genes encoding one or more immune molecules that allow for recognition by the adaptive immune system. For example, heterologous chimeric receptor-expressing cells, such as from unrelated individuals or relatives, can be modified so as to minimize potential immunogenicity. Exemplary immune recognition molecules include, without limitation, MHC class I molecules, MHC class I co-receptors, MHC class II molecules, MHC class II co-receptors, HLA class I molecules, or HLA class II molecules.

In some embodiments, the allogeneic cell can be a cell which does not express or expresses at low levels an inhibitory molecule, e.g., by any method described herein. For example, the cell can be a cell that does not express or expresses at low levels an inhibitory molecule, e.g., that can decrease the ability of a chimer receptor-expressing cell to mount an immune effector response. Examples of inhibitory molecules include PD1, PD-L1, CTLA-4, TIM3, CEACAM (e.g., CEACAM-1, CEACAM-3 and/or CEACAM-5), LAG3, VISTA, BTLA, TIGIT, LAIR1, CD160, 2B4 and TGFR beta. Inhibition of an inhibitory molecule, e.g., by inhibition at the DNA, RNA or protein level, can optimize a chimeric receptor-expressing cell's function.

Allogeneic cells that lack expression of a functional MHC or HLA can be obtained by any suitable means, including a knock out or knock down of one or more subunit of HLA or MHC. For example, the cell can include a knock down of MHC or HLA using siRNA, shRNA, clustered regularly interspaced short palindromic repeats (CRISPR) transcription-activator like effector nuclease (TALEN), or zinc finger endo nuclease (ZFN). In some embodiments, an inhibitory nucleic acid, e.g., an inhibitory nucleic acid, e.g., a sRNA, e.g., an siRNA or shRNA, can be used.

In some embodiments, MHC or HLA expression can be inhibited using siRNA or shRNA that targets a nucleic acid encoding a MHC or HLA in a cell. Expression of siRNA and shRNAs in T cells can be achieved using any conventional expression system, e.g., such as a lentiviral expression system.

CRISPR, as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a MHC or HLA gene. The CRISPR/Cas system has been modified for use in gene editing (silencing, enhancing or changing specific genes) in eukaryotes such as mice or primates. This is accomplished by introducing into the cell a plasmid containing a specifically designed CRISPR and one or more appropriate Cas. The CRISPR/Cas system can thus be used to edit a gene (adding or deleting a basepair), or introducing a premature stop which thus decreases expression of a MHC or HLA. The CRISPR/Cas system can alternatively be used like RNA interference, turning off MHC or HLA gene in a reversible fashion. In a mammalian cell, for example, the RNA can guide the Cas protein to a MHC or HLA promoter, sterically blocking RNA polymerases.

A TALEN protein is a transcription activator-like effector nuclease, an artificial nuclease which can be used to edit the MHC or HLA gene. TALENs are produced artificially by fusing a TAL effector DNA binding domain to a DNA cleavage domain. They can be engineered to bind any desired DNA sequence, including a portion of the HLA or MHC gene. By combining an engineered TALE with a DNA cleavage domain, a restriction enzyme can be produced which is specific to any desired DNA sequence, including a HLA or MHC sequence. These can then be introduced into a cell, wherein they can be used for genome editing.

ZFNs are artificial nucleases which can be used to edit the HLA and/or MHC gene. Like a TALEN, a ZFN comprises a Fok1 nuclease domain (or derivative thereof) fused to a DNA-binding domain. In the case of a ZFN, the DNA-binding domain comprises one or more zinc fingers and must dimerize to cleave DNA. The two individual ZFNs must bind opposite strands of the DNA with their nucleases properly spaced apart. A ZFN can create a double-stranded break in the DNA, which can create a frame-shift mutation if improperly repaired, leading to a decrease in the expression and amount of HLA or MHC in a cell. ZFNs can also be used with homologous recombination to mutate in the HLA or MHC gene.

In some embodiments, genes encoding key immune molecules such as MHC class I and II, the Beta2-Microglobulin component of the MHC class I complex, or the invariant chain component of MHC class II can be mutated or deleted or otherwise rendered dysfunctional using CRISPR-Cas9, TALEN, or Zinc Finger nucleases. Vectors to deliver CRISPR-Cas9, TALEN, Zinc Finger nucleases or similar reagents can be transfected or transduced in the cells, or these factors could be introduced as RNA or proteins. Immune cells can then be screened or purified for the loss of expression of the immune molecules, such as MCH class I or II. Such methods may reduce the potential for antigenicity of the introduced chimeric receptor-expressing cells in the context of heterologous treatment therapies.

Pharmaceutical Compositions

Certain aspects of the present disclosure relate to pharmaceutical compositions comprising polynucleotides, vectors, or cells encoding chimeric receptors and a pharmaceutically acceptable carrier. Polynucleotides, vectors, or cells encoding the chimeric receptors of the present disclosure can be incorporated into a variety of formulations for therapeutic administration by combining the polynucleotides, vectors, or cells with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the polynucleotides, vectors, or cells encoding chimeric receptors of the present disclosure, in a biodegradable or bioerodible implant. The rate of release of the therapeutically active agent is controlled by the rate of transport through the polymeric matrix, and the biodegradation of the implant. The transport of agent through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e., having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions that may be employed include, without limitation, organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject disclosures. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing polynucleotides, vectors, or cells encoding chimeric receptors of the present disclosure may be administered to an individual in need of treatment, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the polynucleotides, vectors, or cells encoding chimeric receptors of the present disclosure, normal dosage amounts may vary depending on an individual's body weight and upon the route of administration. For repeated administrations over several days or longer, depending on the severity of the disease, disorder, or condition to be treated, the treatment is sustained until a desired suppression of symptoms is achieved.

Different dosage regimens may be useful, depending on the pattern of pharmacokinetic decay that the physician wishes to achieve. For example, dosing an individual from one to twenty-one times a week is contemplated herein. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the polynucleotides, vectors, or cells encoding chimeric receptors administered, can vary over time independently of the dose used.

Dosages for particular polynucleotides, vectors, or cells encoding chimeric receptors may be determined empirically in individuals who have been given one or more administrations of the polynucleotides, vectors, or cells encoding chimeric receptors. Individuals are given incremental doses of polynucleotides, vectors, or cells encoding chimeric receptors. To assess efficacy of polynucleotides, vectors, or cells encoding chimeric receptors, a clinical symptom of any of the diseases, disorders, or conditions of the present disclosure (e.g., cancer) can be monitored.

Administration of polynucleotides, vectors, or cells encoding chimeric receptors of the present disclosure can be continuous or intermittent, depending, for example, on the recipient's physiological condition, whether the purpose of the administration is therapeutic or prophylactic, and other factors known to skilled practitioners. The administration of polynucleotides, vectors, or cells encoding chimeric receptors may be essentially continuous over a preselected period of time or may be in a series of spaced doses.

Guidance regarding particular dosages and methods of delivery is provided in the literature; see, for example, U.S. Pat. No. 4,657,760; 5,206,344; or 5,225,212. It is within the scope of the disclosures that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

The innate immune cells expressing a chimeric receptor of the present disclosure may be used in therapeutic treatment processes. Not to be bound by theory, cancer could be suppressed by introducing modified immune cells that express a chimeric receptor and are programmed to be activated appropriately and selectively only in the presence of cancer pathology. Immune cells may be modified to express a chimeric receptor in vitro, ex vivo, or in vivo.

In some embodiments, a plurality of isolated immune cells expressing chimeric receptors is administered to a patient. In some embodiment the plurality of isolated immune cells is administered peripherally. In some embodiments, the plurality of isolated immune cells is administered peripherally into the individual without irradiation.

In some embodiments, the isolated immune cells are autologous cells. For example, the innate immune cells may be obtained from a subject in need of treatment, modified to express a chimeric receptor of the present disclosure, and transferred back into the same individual. In some embodiments, the cells are from an allogeneic donor. For example, the cells may be obtained from a different individual, modified to express a chimeric receptor, and transferred into a subject in need of treatment. In some embodiments, the allogeneic cells are modified to lack one or more genes encoding one or more immune molecules that allow for recognition by the adaptive immune system. For example, heterologous chimeric receptor-expressing cells, such as from unrelated individuals or relatives, can be modified so as to minimize potential immunogenicity. Exemplary immune recognition molecules include that can be modified include, without limitation, HLA class I molecules and HLA class II molecules.

In some embodiments, a source of cells is obtained from a subject prior to modification (e.g., delivery of a polynucleotide encoding a chimeric receptor). Cells can be obtained from a number of sources, including peripheral blood mononuclear cells, bone marrow, lymph node tissue, cord blood, thymus tissue, tissue from a site of infection, ascites, pleural effusion, spleen tissue, and brain. In some embodiments, cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps.

Some embodiments of the present disclosure involved a method of preventing, reducing risk, or treating cancer in an individual. For example, the method may include obtaining a plurality of isolated immune cells, introducing a vector containing polynucleotides encoding a chimeric receptor into the plurality of isolated immune cells, and administering to the individual a therapeutically effective amount of the plurality of isolated immune cells containing the vector. In some embodiments, myeloid cells isolated from a patient may be transfected with a polynucleotide encoding a chimeric receptor directed toward a cancer-associated ligand and then returned to the patient so that the cellular response generated by such cells is triggered. In some embodiments, the vector contained in the plurality of isolated immune cells is expressed after administration of the plurality of immune cells to the individual.

In some embodiments, a specific cell subpopulation can be selected prior to modification (e.g., delivery of a polynucleotide encoding a chimeric receptor). For example, cells can be immunolabeled by staining with antibodies for specific cell surface markers. The immunolabeled cells can then be subjected to selection via positive or negative of specific subpopulations. Techniques to select specific subpopulations include, without limitation, bead-based selection and fluorescence-activated cell sorting (FACS). For example, enrichment of a cell population by negative selection can be accomplished, e.g., with a combination of antibodies directed to surface markers unique to the negatively selected cells. Cell sorting and/or selection via negative magnetic immunoadherence or flow cytometry may be subsequently used to achieve enrichment of the desired cell population.

In some embodiments, administering the innate immune cells containing a chimeric receptor or polynucleotides encoding said receptor induces one or more activities, including without limitation, TREM1 or DAP12 phosphorylation, activation of one or more kinases, modulated signaling pathways, modulated expression or one or more proteins, modulation of one or more pro-inflammatory or anti-inflammatory mediators, modulated expression of C—C chemokine receptor 7 (CCR7), induction of microglial cell chemotaxis toward CCL19 and CCL21 expressing cells, maturation, function, or survival of dendritic cells, monocytes, microglia, macrophages, astrocytes, osteoclasts, Langerhans cells, or Kupffer cells, modified osteoclast production or rate of osteoclastogenesis, induction of clearance or phagocytosis of disease-associated factors (e.g., protein, nucleic acids, or cells), increased expression of one or more stimulatory molecules, activation of tumor cell killing, anti-tumor cell proliferation, or anti-tumor cell metastasis by one or more of microglia, macrophages, dendritic cells, bone marrow-derived dendritic cells, neutrophils, or any combination thereof, decreasing tumor volume or tumor growth rate, and increasing efficacy of one or more immune-therapies that modulate anti-tumor T cell responses.

In some embodiments, chimeric receptors of the present disclosure are used to treat or prevent cancer. In some embodiments, a cancer to be prevented or treated by the methods of the present disclosure includes, but is not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, the cancer is a cancer associated with expression of CD19. In some embodiments, the cancer associated with expression of CD19 is a hematological cancer such as leukemia or lymphoma. In some embodiments, the cancer associated with expression of CD19 is one or more acute leukemias, including without limitation, B-cell acute Lymphoid Leukemia (BALL), T-cell acute Lymphoid Leukemia (TALL), and acute lymphoid leukemia (ALL); or one or more chronic leukemias, including without limitation, chronic myelogenous leukemia (CML) and Chronic Lymphoid Leukemia (CLL). Additional cancers or hematologic conditions associated with expression of CD19 include, without limitation, B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma (MCL), Marginal zone lymphoma, multiple myeloma, myelodysplasia and myelodysplasia syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells.

Certain aspects of the present disclosure provide methods of preventing, reducing risk, or treating cancer comprising administering to an individual in need thereof a therapeutically effective amount of an isolated cell containing a chimeric receptor or polynucleotides encoding such chimeric receptors. For example, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, or myeloid-derived tumors, is treated by administering to the individual a therapeutically effective amount of a plurality of immune cells expressing the chimeric receptor.

Without wishing to be bound by theory, it is believed that administering a therapeutically effective amount of a plurality of isolated immune cells expressing a chimeric receptor of the present disclosure can prevent, reduce the risk, and/or treat cancer. In some embodiments, administering a therapeutically effective amount of the plurality of isolated immune cells expressing the chimeric receptor may induce one or more activities in an individual having cancer (e.g., myeloid cell activation, proliferation, survival, phagocytosis, and/or functionality against pathologies associated with cancer).

Additional Therapies

In some embodiments, the methods for preventing, reducing risk, or treating an individual having cancer further include administering to the individual at least one additional therapeutic agent.

In some embodiments, the method further includes administering to the individual at least one antibody that specifically binds to an inhibitory checkpoint molecule, and/or another standard or investigational anti-cancer therapy. In some embodiments, the at least one antibody that specifically binds to an inhibitory checkpoint molecule is administered in combination with innate immune cells expressing the chimeric receptor. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-AZAR antibody, an anti-LAG-3 antibody, an anti-phosphatidylserine antibody, an anti-CD27 antibody, an anti-TNF-α antibody, an anti-CD33 antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, and any combination thereof. In some embodiments, the standard or investigational anti-cancer therapy is one or more therapies selected from radiotherapy, cytotoxic chemotherapy, targeted therapy, imatinib (Gleevec®) therapy, trastuzumab (Herceptin®) therapy, etanercept therapy, adoptive cell transfer (ACT) therapy, chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with innate immune cells expressing the chimeric receptor. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory checkpoint protein. In some embodiments, the at least one agonistic antibody that specifically binds to a stimulatory checkpoint protein is administered in combination with innate immune cells expressing the chimeric receptor. hi some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with innate immune cells expressing the chimeric receptor. In some embodiments, the at least one stimulatory cytokine is selected from IFN-☐4, IFN-☐, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, MCP-1, MIP-1-beta, and any combination thereof.

Kits/Articles of Manufacture

The present disclosure also provides kits containing polynucleotides, vectors, or cells encoding chimeric receptors. Kits of the present disclosure may include one or more containers comprising polynucleotides, vectors, or cells encoding chimeric receptors of the present disclosure. hi some embodiments, the kits further include instructions for use in accordance with the methods of this disclosure. In some embodiments, these instructions comprise a description of administration of the polynucleotides, vectors, or cells encoding chimeric receptors of the present disclosure to prevent, reduce risk, or treat an individual having cancer, according to any methods of this disclosure. The kit may further comprise a description of selecting an individual suitable for treatment based on identifying whether that individual has the disease and the stage of the disease.

In some embodiments, the kits may further include an additional therapeutic agent. In some embodiments, the kits may further include instructions for using the additional therapeutic agent in combination with the polynucleotides, vectors, or cells encoding chimeric receptors of the present disclosure, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is a polynucleotide, vector, or cell a encoding chimeric receptor. The container may further comprise a second pharmaceutically active agent.

Kits may optionally provide additional components such as buffers and interpretive information. Normally, the kit comprises a container and a label or package insert(s) on or associated with the container.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Assembly, Production, Identification, and Characterization of SMART Vectors Introduction SMART chimeric receptors are composed minimally of a ligand-binding domain such as an scFv, a transmembrane domain, and one or more intracellular signaling domains. The intracellular domain may be from an ITAM protein domain such as those found in TCRzeta or DAP12.

The antigen binding domain may be composed of an scFv, which can be designed by connecting sequences from the heavy chain and light chain of an antibody via a linker domain. An exemplary linker is shown in SEQ ID NO: 12. Another possible linker for use in the SMART chimeric receptors disclosed herein is the sequence GGGGSGGGGSGGGGS (SEQ ID NO: 34), which is exemplified in the scFv sequence displayed in SEQ ID NO: 13. An example of a complete scFv sequences is provided in SEQ ID NO: 13 (CD19 scFv). To generate a SMART vector, these linkers must be preceded by a signal sequence to allow for membrane targeting. An exemplary signal sequence from the CD8 gene is shown in SEQ ID NO: 11. A hinge domain may be added downstream of the scFv, preceding the transmembrane domain, functioning as an additional linker. An exemplary hinge domain is shown in SEQ ID NO: 14 (from CD8), and can be followed by a transmembrane domain as shown in SEQ ID NO: 15 (from CD8).

Intracellular signaling domains are chosen for insertion into SMART vectors depending on the desired chimeric receptor activity. For example, ITAM domain signaling promotes survival and can in some contexts polarize towards an M2-type repair phenotype. An exemplary ITAM signaling domain is the CD3Zeta intracellular domain (shown in SEQ ID NO: 1 and SEQ ID NO: 2), which contains 3 ITAM sequences and is predicted to lead to strong signaling. SEQ ID NO: 17, which represents the entire DAP12 molecule minus the signal sequence, is an example of a very short extracellular domain followed by a transmembrane domain and an ITAM domain.

Another exemplary intracellular signaling domain class is derived from receptor tyrosine kinase molecules. One such receptor tyrosine kinase is CSF1R, which can be included as an intracellular domain only (SEQ ID NO: 5), together with the CSF1R transmembrane domain (SEQ ID NO: 4), or as the transmembrane plus extracellular linker/hinge together with the intracellular domain (SEQ ID NO: 3). Such domains can also be derived from other non-human species. Although the use of human derived sequences minimizes antigenicity in humans, sequences derived from non-human species can be used when performing testing in animal models. For example, mouse CSF1R intracellular (SEQ ID NO: 7) and transmembrane domains (SEQ ID NO: 6) can be used.

Signaling domains, such as TLR signaling intracellular domains (SEQ ID NO: 9), may also be used to polarize towards a pro-inflammatory M1-like phenotype. These signaling domains may be used alone, or may be place downstream of a transmembrane domain (SEQ ID NO: 8) and an extracellular linker. Another domain which may lead to pro-inflammatory and survival signaling in myeloid cells is the intracellular domain derived from CD28 (SEQ ID NO: 10). This domain may lead to NFKappaB, Syk, and PI3K signaling induction. Similarly, the 4-1BB intracellular domain (SEQ ID NO: 16), when expressed within SMART vectors in myeloid cells, may lead to pro-inflammatory polarization via induction of NFKappaB and beta-catenin signaling.

Several SMART constructs are described herein, with each utilizing a different combination of antigen binding, linker, transmembrane, and/or intracellular signaling domains. The SMART constructs can be used individually or multiple vectors can be used in any combination. The vectors can be introduced into the same cells or can be introduced into a mixed population of cells that express one or the other vector separately. SMART vectors that may polarize myeloid cells towards a pro-inflammatory state, for use in conditions such as cancer, have also been designed.

SMART1 is composed of the elements CD8 SS>>anti-CD19SCfV>>CD8 Hinge>>CD8TM>>4-1BB intracellular>>CD3Z ITAM. The SMART1 construct may target tumors expressing the CD19 marker. The sequences for SMART1 are provided in SEQ ID NO: 20 (amino acid) and SEQ ID NO: 27 (polynucleotide), and the vectors are shown in FIGS. 1A and 1B. Combined 4-1BB signaling and CD3Z through this receptor may lead to NFKappaB and ITAM pro-survival signaling and pro-inflammatory polarization of myeloid cells.

Figure 2B:
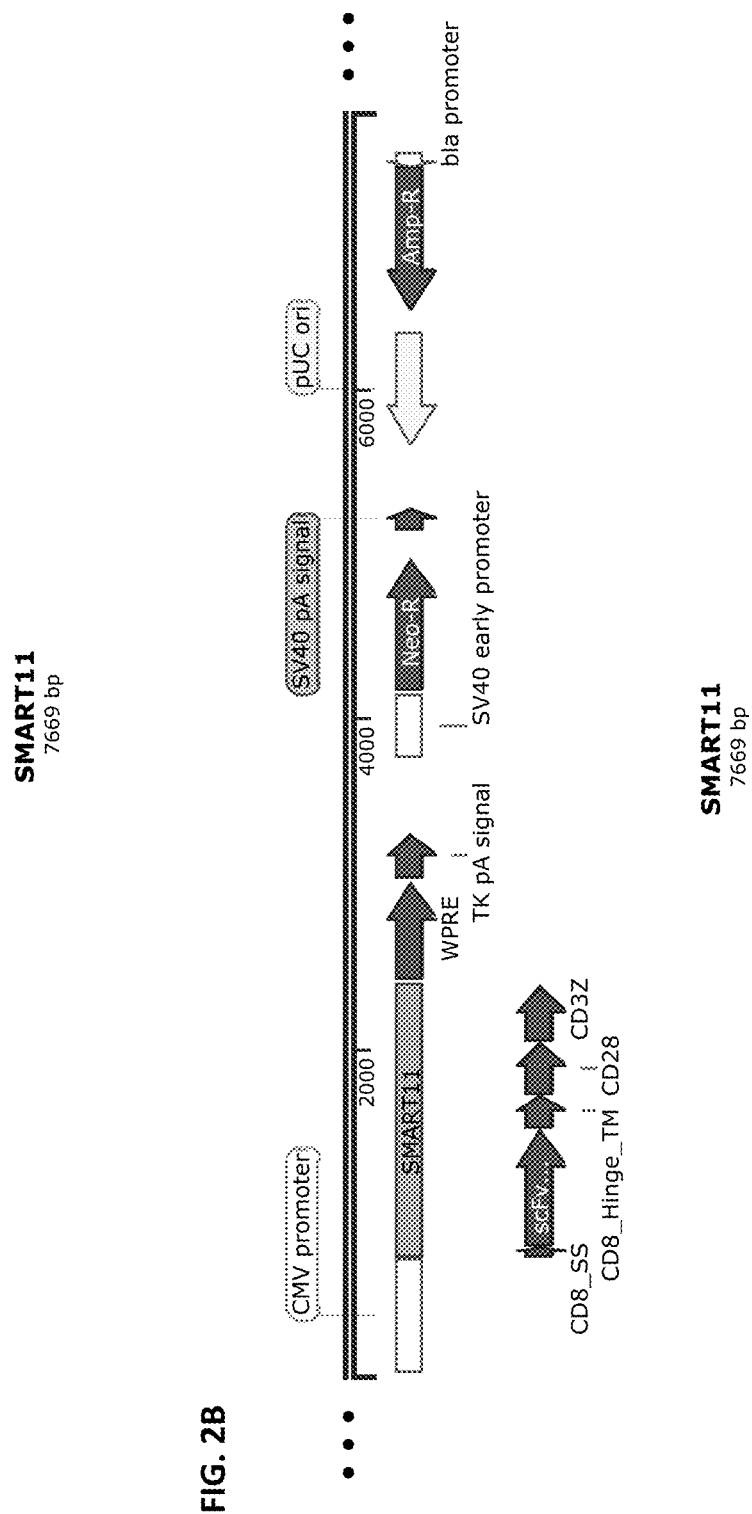

SMART11 is composed of the elements CD8 SS>>anti-CD19SCfV>>CD8 Hinge>>CD8TM>>CD28>>CD3Z ITAM. SMART13 may lead to CD28 and ITAM mediated survival and signaling and NFKB-mediated pro-inflammatory M1 polarization in the context of the CD19 tumor antigen. The sequences for SMART11 are provided in SEQ ID NO: 21 (amino acid) and SEQ ID NO: 28 (polynucleotide), and the vectors are shown in FIGS. 2A and 2B. This construct may allow a selective and local activation of myeloid cell activity in the context of tumor antigens, leading to pro-inflammatory activation of myeloid cells and CTL activation against tumors.

SMART12 is composed of the elements CD8 SS>>anti-CD19SCfV>>CD8 Hinge>>CD8TM>>TLR5 intracellular domain. SMART12 may lead to activation of survival and signaling via NFKB-mediated pro-inflammatory M1 polarization in the context of the CD19 tumor antigen. This signaling may subsequently lead to production of TNFa and other pro-inflammatory mediators of CU; activation and to inhibition of suppressive signaling from myeloid derived suppressor cells (MDSC). The sequences for SMART12 are provided in SEQ ID NO: 22 (amino acid) and SEQ ID NO: 29 (polynucleotide), and the vectors are shown in FIGS. 3A and 3B. This construct may allow a selective and local activation of myeloid cell activity in the context of tumor antigens, leading to pro-inflammatory activation of myeloid cells and CTL activation against tumors.

Figure 4A:
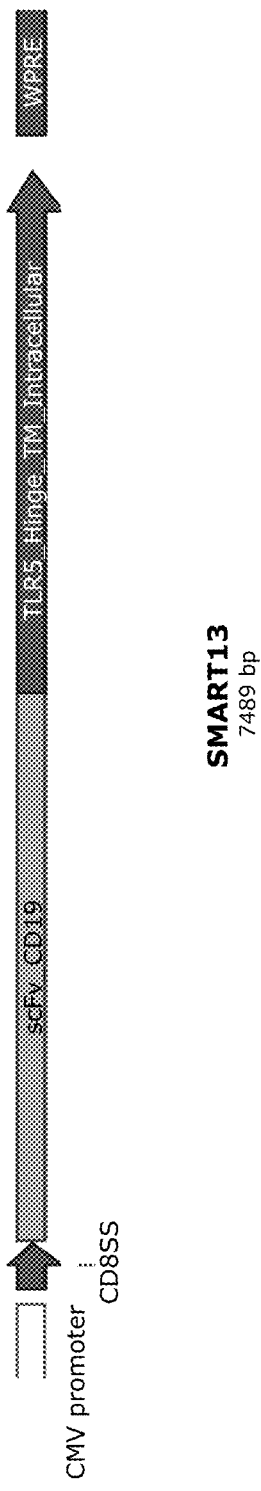
FIG. 4A and FIG. 4B show a schematic of the SMART13 chimeric receptor structure (FIG. 4A) and a schematic of a vector that harbors this receptor cloned into pCDNA3.4-Topo from Life Technologies (FIG. 4B). SMART13 is composed of the elements: CD8 SS>>anti-CD19SCfV>>TLR5 hinge and transmembrane>>TLR5 intracellular domain.
Figure 4B:
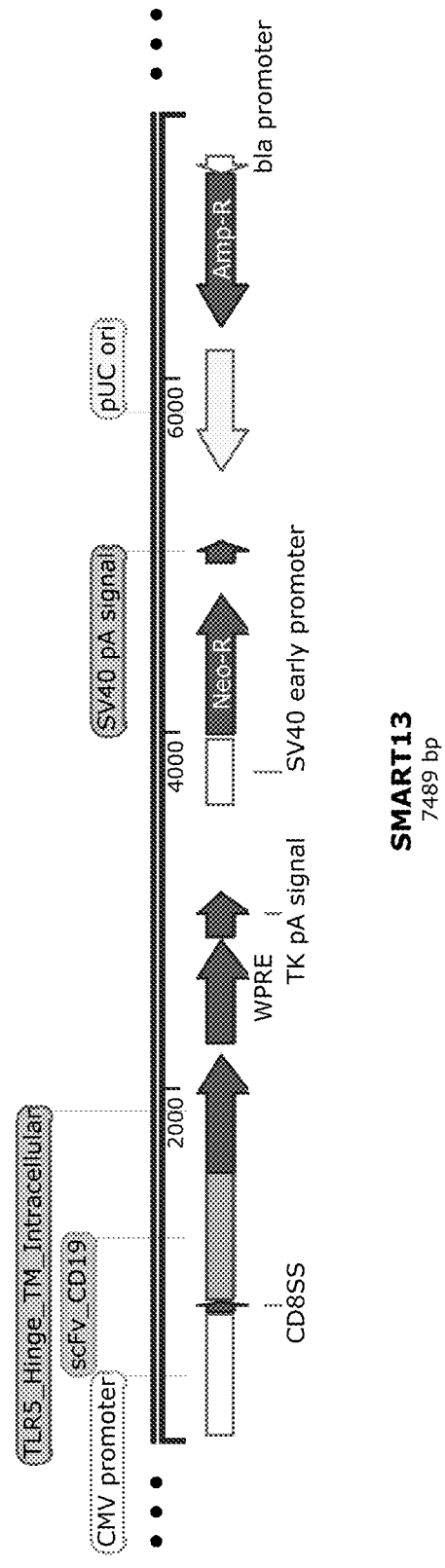

SMART13 is composed of the elements CD8 SS>>anti-CD19SCfV>>TLR5 hinge and transmembrane>>TLR5 intracellular domain. SMART13 may lead to activation of survival and signaling via NFKB-mediated pro-inflammatory M1 polarization in the context of the CD19 tumor antigen. The sequences for SMART13 are provided in SEQ ID NO: 23 (amino acid) and SEQ ID NO: 30 (polynucleotide), and the vectors are shown in FIGS. 4A and 4B. This construct may allow a selective and local activation of myeloid cell activity in the context of tumor antigens, leading to pro-inflammatory activation of myeloid cells and CTL activation against tumors. Compared to SMART12, SMART13 has a more native TLR5 structure and thus may display a more typical TLR5 signaling profile in the context of tumor antigen. This signaling may subsequently lead to production of TNFa and other pro-inflammatory mediators of CTL activation and to inhibition of suppressive signaling from myeloid derived suppressor cells (MDSC).

Figure 5A:
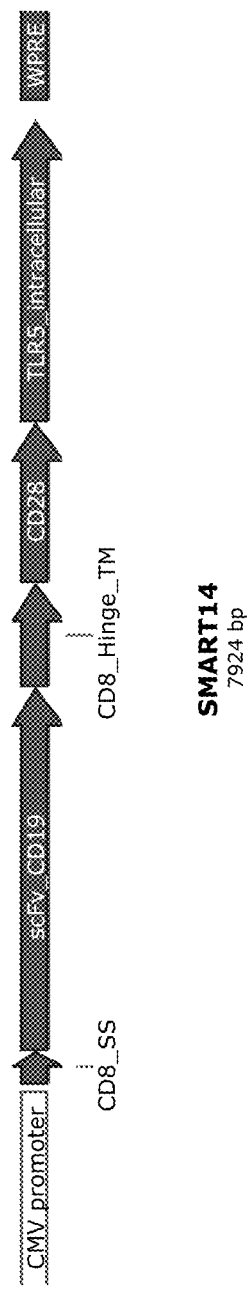
FIG. 5A and FIG. 5B show a schematic of the SMART14 chimeric receptor structure (FIG. 5A) and a schematic of a vector that harbors this receptor cloned into pCDNA3.4-Topo from Life Technologies (FIG. 5B). SMART14 is composed of the elements: CD8 SS>>anti-CD19 SCfV>>CD8 Hinge>>CD8TM>>CD28 intracellular domain>>TLR5 intracellular domain.
Figure 5B:
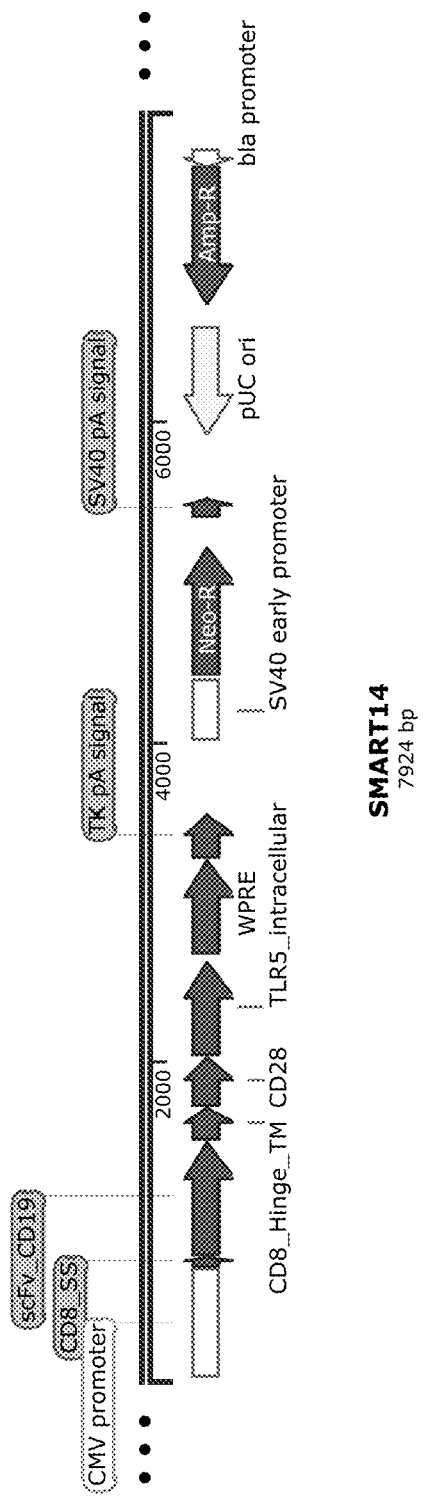

SMART14 is composed of the elements CD8 SS>>anti-CD19 SCfV>>CD8 Hinge>>CD8TM>>CD28 intracellular domain>>TLR5 intracellular domain. SMART14 may lead to activation of survival and signaling via NFKB-mediated pro-inflammatory M1 polarization in the context of the CD19 tumor antigen, and additional survival and inflammatory signaling can occur through CD28. The sequences for SMART14 are provided in SEQ ID NO: 74 (amino acid) and SEQ ID NO: 31 (polynucleotide), and the vectors are shown in FIGS. 5A and 5B. This construct may allow a selective and local activation of myeloid cell activity the context of tumor antigens, leading to pro-inflammatory activation of myeloid cells and CTL activation against tumors.

Figure 6A:
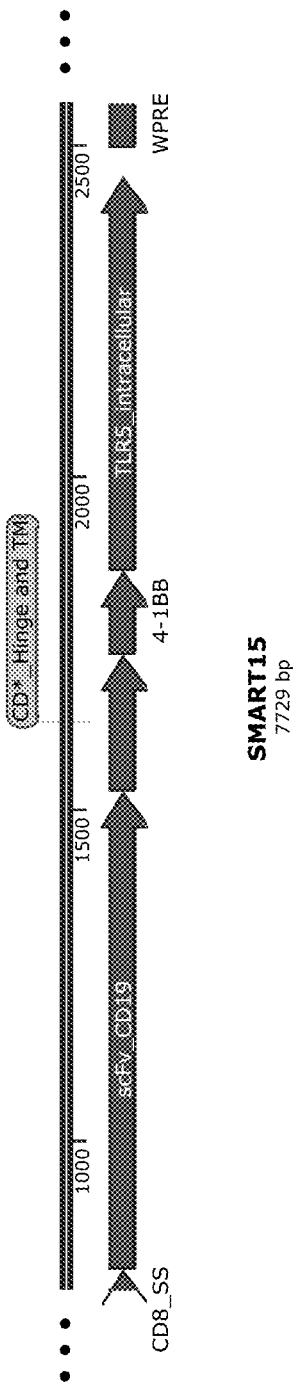
FIG. 6A and FIG. 6B show a schematic of the SMART15 chimeric receptor structure (FIG. 6A) and a schematic of a vector that harbors this receptor cloned into pCDNA3.4-Topo from Life Technologies (FIG. 6B). SMART15 is composed of the elements: CD8 SS>>anti-CD19 SCfV>>CD8 Hinge>>CD8TM>>4-1BB intracellular domain>>TLR5 intracellular domain.
Figure 6B:
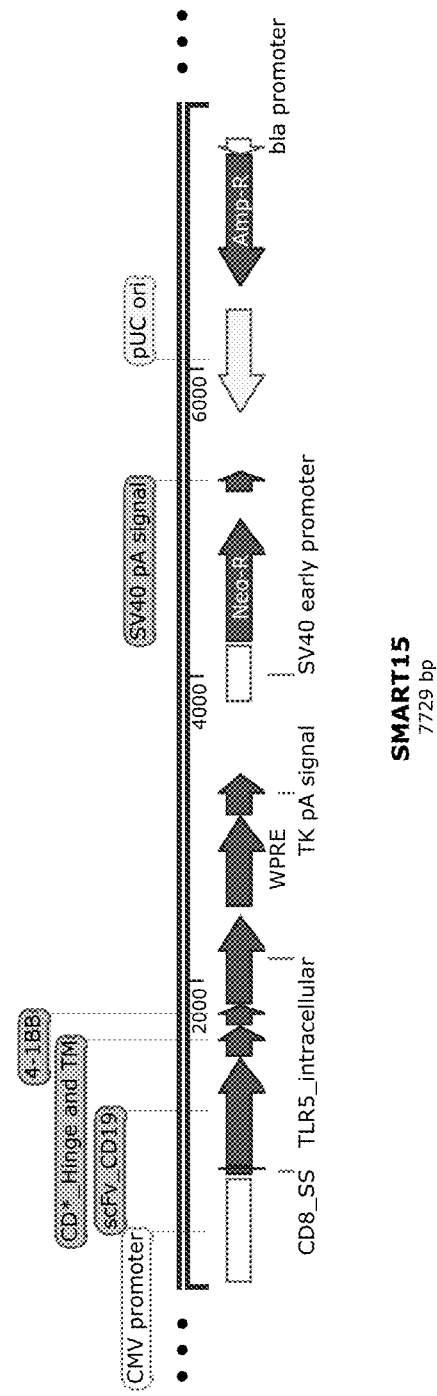

SMART15 is composed of the elements CD8 SS>>anti-CD19SCfV>>CD8 Hinge>>CD8TM>>4-1BB>>TLR5 intracellular domain. SMART15 may lead to activation of survival and signaling via NFKB-mediated pro-inflammatory M1 polarization in the context of the CD19 tumor antigen. This signaling may subsequently lead to production of TNFa and other pro-inflammatory mediators of CTL activation and to inhibition of suppressive signaling from myeloid derived suppressor cells (MDSC). Additional 4-1BB signaling may co-activate and lead to improved survival and pro-inflammatory proliferative signals. The sequences for SMART15 are provided in SEQ ID NO: 25 (amino acid) and SEQ ID NO: 32 (polynucleotide), and the vectors are shown in FIGS. 6A and 68. This construct may allow a selective and local activation of myeloid cell activity in the context of tumor antigens, leading to pro-inflammatory activation of myeloid cells and CTL activation against tumors.

Figure 7A:
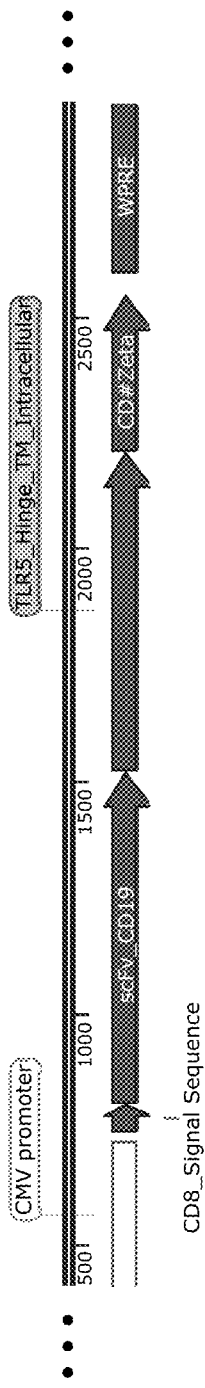
FIG. 7A and FIG. 7B show a schematic of the SMART16 chimeric receptor structure (FIG. 7A) and a schematic of a vector that harbors this receptor cloned into pCDNA3.4-Topo from Life Technologies (FIG. 7B). SMART16 is composed of the elements: CD8 SS>>anti-CD19
Figure 7B:
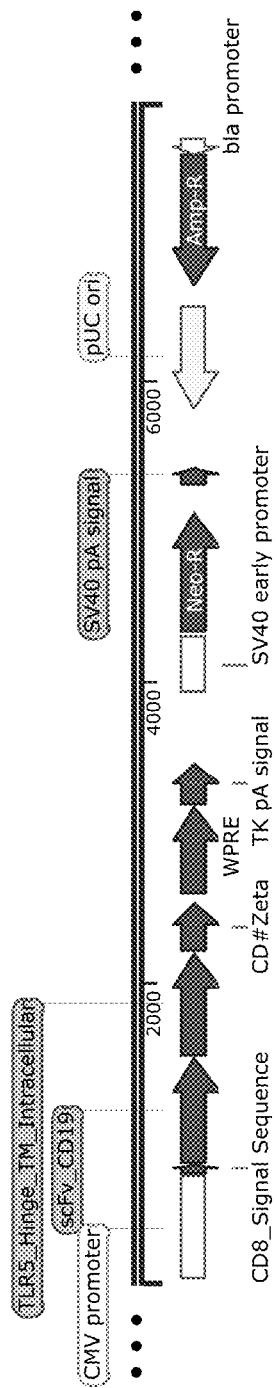

SMART16 is composed of the elements CD8 SS>>anti-CD19 SCfV>>TLR5 hinge and transmembrane>> TLR5 intracellular>>CD3zeta intracellular domain. SMART16 may lead to activation of survival and signaling through NFKB-mediated pro-inflammatory M1 polarization in the context of the CD19 tumor antigen. This signaling may subsequently lead to production of TNFa and other pro-inflammatory mediators of CTL activation and to inhibition of suppressive signaling from myeloid. derived suppressor cells (MDSC). Additional CD3Z-mediated signals may co-activate and lead to improved survival through the ITAM domain. The sequences for SMART15 are provided in SEQ ID NO: 26 (amino acid) and SEQ ID NO: 33 (polynucleotide), and the vectors are shown in FIGS. 7A and 7B. This construct may allow a selective and local activation of myeloid cell activity in the context of tumor antigens, leading to pro-inflammatory activation of myeloid cells and CTL activation against tumors.

Example 2: Transduction of SMART Vectors into Myeloid Cells In Vitro

SMART vectors can be transduced into primary human myeloid cells or animal model myeloid cells by transfection or transduction using a viral vector such as a lentivirus vector. To determine whether the SMART vectors described in Example 1 can be expressed as intact chimeric proteins, myeloid cells are transfected with individual SMART plasmid vectors. Linearized plasmid vectors are electroporated under optimized conditions and stable transfectants are selected by addition of G418, hygromycin, or another selectable marker to cell cultures, as appropriate for the vector used.

Western blot or FACS analyses of myeloid cells with antibodies directed against the different chimeric receptor domains are used to confirm expression of the chimeric receptors in the cells. Whole cell lysates from mock transfectants (cells containing the vector without a SMART insert) and from myeloid cells transfected with SMART vectors are compared. For example, Western blot of whole cell lysates from cells transfected with a SMART vector that includes the CD3zeta domain with an anti-CD3zeta antibody probe can show expression of the intact chimeric receptor protein in cells transfected with the chimeric receptor but not in the mock transfectants. Flow cytometric analysis with anti-human Fab specific antibodies can further confirm the cell-surface expression of the SMART chimeric receptors on cell transfectants. Similarly, SMART vectors are inserted into lentiviral vectors which can then be produced and used to transduce the SMART construct into myeloid cells.

Example 3: Transduction of Bone Marrow-Derived Dendritic Cells (BMDC) with SMART Receptors Lentiviral mediated transduction of myeloid cells with vectors encoding SMART1 and SMART 11-16 chimeric receptors is performed. Monocytes are isolated from buffy coats of healthy donors following Lymphoprep gradient centrifugation and positive or negative magnetic antibody separation kit (Miltenyi Biotec, Leiden, Netherlands). Purity is assessed by flow cytometry of anti-CD14-PE stained cells. Isolated cells are cultured in 24-well plates at 250,000 cells/well in 0.5 mL of RPMI medium (RPMI 1640, Life Technologies, Carlsbad, Calif.) supplemented with 2 mM L-glutamine (Life Technologies), 2.5% (vol/vol) heat inactivated fetal calf serum (FCS, Hyclone Perbio, Thermo Scientific, Rockford, Ill.), 100 U/mL penicillin, 100 µg/mL streptomycin (Life Technologies), IL-4 at 500 IU/mL, and GM-CSF at 1,000 IU/mL (Gentaur, Kampenhout, Belgium) at 37° C. in a humidified atmosphere containing 5% (vol/vol) $CO_2$. To assess the impact of fetal calf serum on MDDC transduction efficiency, sera from Biochrom (Merc Milipore, Overijse, Belgium), Bovogen Biologicals (East Keilor, Australia), Lonza (Verviers, Belgium) and PAA (GE Healthcare, Diegem, Belgium) are also used. To ensure standardized transduction, lentiviral supernatants are titrated. Six days post-transduction the cells are plated in a 96-well plate at 50,000 cells/well and infected (50 ng p24) by spinoculation (90 min, 950 g, 32° C.), with continuous spinning in a centrifuge, in presence of 1 μM ritonavir (NIH AIDS Reagent Program, Germantown, Md.) in a final volume of 200 μL. On day 1 post-infection, medium is refreshed. Infection is measured on day 3 by flow cytometry, gaiting on live cells as determined by propidium iodide staining (Miltenyi Biotec).

Viral reverse transcriptase (RT) activity, quantitative real-time qPCR for viral DNA of long terminal repeat sequences, or ELISA of p24 viral protein are performed using standard techniques. Supernatant of lentiviral vector encoding a scrambled sequence or an eGFP marker gene showed an MOI of 10 when measured on 293T cells and provided over 95% MDDC transduction efficiency. This lentiviral supernatant expressed RT activity of 5,550 mU/ml (equivalent of 1 μg of p24/ml as assessed by ELISA) in previous studies. Aliquots of this supernatant are included in all subsequent reverse transcriptase activity assays to serve as a standard reference for viral production.

Monocytes are obtained by positive magnetic bead-based selection of CD14+ cells. On day 1 post-monocyte isolation, medium is replaced with fresh medium containing 50% lentiviral supernatant. RT activity of 2,750-5,550 mU/ml is used. Cells are subsequently spinoculated (90 min, 950 g, 32° C.) in the presence of polybrene (4 μg/mL; Sigma-Aldrich, Diegem, Belgium). Medium is refreshed 24 h post-transduction and cells are cultured in the presence of IL-4 and GM-CSF until day 6. In some experiments, maturation is induced with LPS (100 ng/mL; Sigma-Aldrich). From day 6 post-transduction onwards, cells are cultured in 10% FCS (vol/vol) RPMI medium supplemented with glutamine, penicillin and streptomycin.

SMART vector sequences are inserted into a pLKO.1 based vectors expression cassette under the direction of an appropriate promoter element. Transfection of vectors into 293T cells is performed using standard approaches. Viral production is achieved using standard second or third-generation lentiviral transduction vector packaging production kits, such as Virapower (Life Technologies/Fisher Scientific) using the manufacturer's instructions. The titer of the viral supernatants is measured by quantification of reverse transcriptase activity via real time-PCR and expressed as equivalent p24 as described above.

Although lentiviral vectors can be inhibited in human myeloid cells, Witkowski et al. (Witkowski, Vermeire et al., PLoS One, e0133651, 2015) optimized the transduction of MDDCs by investigating the effect of a range of parameters, including additives such as polybrene, spinoculation, and experimental timeline. This optimized protocol is subsequently used in the experiments described herein. Transduction is performed by spinoculation as described above in the presence of polybrene, which can facilitate virus-cell binding and entry. To measure transduction efficiency, a pLKO.1-derived lentiviral vector encoding an eGFP marker gene is used. Transduction efficiency, as well as the MDDC phenotype, is evaluated five days post-transduction.

Example 4: Normalization and Reduction of Toll-Like Receptor (TLR) Responses in Dendritic Cells Expressing SMART Receptors in the Presence of Ligand Bone marrow-derived dendritic cells (BMDC), expressing control vector or SMART encoding vectors, are introduced by viral transduction or by electroporation. BMDCs are subsequently stimulated by culturing with TLR ligands, such as LPS, CpG DNA, and zymosan, for 16 h. Conditioned media is collected and ELISA assays are performed in order to evaluate secretion of the cytokines IFN-a, IFN-b, IL-6, IL-12 p70, and TNF. BMDC cells expressing pro-repair SMART vectors, that signal through RTK or ITAM domain receptors, may secrete significantly more IL-12, p70, and TNF upon simulation with multimerized ligand than control BMDC cells. It is further believed that the presence of ligands of pro-repair SMART receptors will reduce the expression levels of IL-12, p70, and TNF.

In contrast, cells expressing pro-inflammatory SMART receptors, such as SMART1 or SMART11-16, which signal through TLR5, CD28, 4-1BB, or CD3Zeta domains, can induce a proinflammatory polarization in the presence of a multimer ligand (e.g., ligand on the surface of CD19-expressing B cell lineage tumor cells). BMDC cells expressing pro-inflammatory SMART vectors, such as the SMART1 or SMART 11-SMART16, may secrete significantly more IL-12, p70, and TNF in the presence of a multimerized ligand (e.g., ligand on the surface of CD19-expressing B cell lineage tumor cells) than in the absence of such a ligand. The presence of pro-inflammatory SMART receptor ligands may also induce the expression of IL-12, p70, and TNF.

Example 5: Ability of Pro-Repair SMART Receptor-Expressing BMDC to Mediate Normalization and Reduction of Antigen-Specific T-Cell Proliferation in the Presence of Ligand Bone marrow-derived dendritic cells (BMDC) that express pro-repair SMART vectors may, in the presence of multimeric ligand, inhibit antigen-specific T-cell proliferation. For example, the Ovalbumin (OVA)-specific T-cell response induced by BMDCs can be determined by CFSE dilution. BMDCs are isolated by MACS after 6 days of culture and plated at $1 \times 10^4$ cells per well in a round bottom 96 well plate with OVA (2 or 0.5 mg/mL) and CpG DNA (100 or 25 nM) in the presence of GM-CSF (10 ng/mL) for 4 h. CD4 T-cells from the spleen and lymph nodes of OT-II transgenic mice are isolated using the Dynal Mouse CD4 Negative Isolation Kit (Invitrogen) and stained with CFSE (final 0.8 mM). After 4 h of DC culture, $1 \times 10^5$ CFSE-labeled CD4 OT-II T-cells are added into each well and incubated for 72 h. After culturing, cells are stained with an anti-CD4 monoclonal antibody and flow cytometry is performed to detect CFSE dilution of gated CD4 OT-II T-cells. Data analysis to calculate the percentage of divided and division index is performed by Flowjo software (Treestar) (Eur. J. Immunol. 2012. 42: 176-185). The presence of ligand can suppress T cell proliferation relative to the absence of the multimerized ligand. Cytokine concentrations in the culture supernatants are determined using mouse IFN-a4, IFN-b, IL-6, IL-12 p70, TNF, and IL-10 ELISA kits (eBioscience) and VeriKine Mouse IFN-b ELISA kit (PBL interferon source) according to the manufacturer's protocol. Levels of mRNA for these cytokines are also measured by Quantitative RT-PCR (qRT-PCR). Total RNA prepared using the RNeasy plus mini kit (QIAGEN) is reverse-transcribed with Superscript III Reverse Transcriptase (Invitrogen) using oligo dT primer according to the manufacturer's protocol. Quantitative PCR is performed using the Power SYBR Green PCR Master Mix (Applied Biosystems) and 7900HT (Applied Biosystems) according to the manufacturer's protocol. The sequences of IFN-α4, IFN-b, IL-6, IL-12 p70, and TNF primers are described previously. (e.g., Hamerman, J A, Eur. J. Immunol. 2012. 42: 176-185).

Example 6: BMDC Mediated Induction of Antigen-Specific T-Cell Proliferation when Expressing Pro-Inflammatory SMART Receptors in the Presence of Ligand Bone marrow-derived dendritic cells (BMDC) that express pro-inflammatory SMART vectors may, in the presence of multimeric ligand, induce antigen-specific T-cell proliferation. For example, the Ovalbumin (OVA)-specific T-cell response induced by BMDCs can be determined by CFSE dilution. BMDCs are isolated by MACS after 6 days of culture and plated at $1 \times 10^4$ cells per well in a round bottom 96 well plate with OVA (2 or 0.5 mg/mL) and CpG DNA (100 or 25 nM) in the presence of GM-CSF (10 ng/mL) for 4 h. CD4 T-cells from the spleen and lymph nodes of OT-II transgenic mice are isolated using the Dynal Mouse CD4 Negative Isolation Kit (Invitrogen) and stained with CFSE (final 0.8 mM). After 4 h of DC culture, $1 \times 10^5$ CFSE-labeled CD4 OT-II T-cells are added into each well and incubated for 72 h. After culturing, cells are stained with an anti-CD4 monoclonal antibody and flow cytometry is performed to detect CFSE dilution of gated CD4 OT-II T-cells. Data analysis to calculate the percentage of divided and division index is performed by Flowjo software (Treestar) (Eur. J. Immunol. 2012. 42: 176-185).

Ligand for SMART expressing myeloid cells may be presented on tumor cells or artificial antigen expressing cells; alternatively the multimerized ligand or epitopes may be presented free of cells. For example, for cell-bound ligand, human CD19 and CD80 expressing fibroblasts such as 3T3-CD19-CD80 cells (Latouche and Sadelain, Nat Biotechnol, 405-409, 2000, Brentjens, Riviere et al., Blood, 4817-4828, 2011), or tumor cells expressing CD19 ligand, can be irradiated at 30 Gy. SMART-expressing BMDCs are isolated by MACS (Miltenyi Biotec) and plated on the 3T3-CD19-CD80 cells, other artificial CD19 expressing cells, or on CD19 expressing tumor cells. After 24, 48, or 72 hrs, conditioned media is collected and ELISA assays are performed to evaluate secretion of the cytokines IFN-a, IFN-b, IL-6, IL-12 p70, and TNF. BMDC cells expressing pro-repair SMART vectors that signal through RTK or ITAM domain receptors may secrete significantly more IL-12, p70, and TNF upon simulation with multimerized ligand than control BMDC cells. The presence of ligands of pro-repair SMART receptors may reduce the expression levels of IL-12, p70, and TNF.

Cytokine concentrations in the culture supernatants are determined using mouse IFN-a4, IFN-b, IL-6, IL-12 p70, TNF, and IL-10 ELISA kits (eBioscience) and VeriKine Mouse IFN-b ELISA kit (PBL interferon source) according to the manufacturer's protocol. Levels of mRNA for these cytokines are also measured by Quantitative RT-PCR (qRT-PCR). Total RNA prepared using the RNeasy plus mini kit (QIAGEN) is reverse-transcribed with Superscript III Reverse Transcriptase (Invitrogen) using oligo dT primer according to the manufacturer's protocol. Quantitative PCR is performed using the Power SYBR Green PCR Master Mix (Applied Biosystems) and 7900HT (Applied Biosystems) according to the manufacturer's protocol. The sequences of IFN-a4, IFN-b, IL-6, IL-12 p70, and TNF primers are described previously. (e.g., Hamerman, J A, Eur. J. Immunol. 2012. 42: 176-185). In the presence of multimerized ligand for these SMART receptors (e.g., ligand on the surface of CD19-expressing B cell lineage tumor cells), T cell proliferation may be induced.

Example 7: Normalization and Reduction of Toll-Like Receptor (TLR) Responses in Macrophages by Pro-Repair SMART Vectors in the Presence of Ligand Signaling through SMART receptors (e.g., through local activation of ITAM or RTK or other such signaling pathways) in the context of multimerized or aggregated ligand, or a high local ligand concentration, may reduce and normalize TLR responses in macrophages.

To elicit primary macrophages, mice are treated with 1.5 ml of 2% thioglycollate medium by intraperitoneal injection, and cells are then isolated by peritoneal lavage. To generate BMDM, total bone marrow is cultured in DMEM supplemented with 10% bovine calf serum, 5% horse serum, and 6 ng/ml recombinant human CSF-1 (R&D Systems). Cells are cultured for 5-6 days, and adherent cells are detached with 1 m MEDTA in PBS. Cells are stained with commercially available antibodies: anti-CD11b, anti-CD40, anti-GR1 (BD Pharmingen), and F4/80 (Caltag Laboratories).

Ligand for SMART expressing myeloid cells may be presented on tumor cells or artificial antigen expressing cells; alternatively the multimerized ligand or epitopes may be presented free of cells. For example, for cell-bound ligand, human CD19 and CD80 expressing fibroblasts such as 3T3-CD19-CD80 cells (Latouche and Sadelain, Nat Biotechnol, 405-409, 2000, Brentjens, Riviere et al., Blood, 4817-4828, 2011), or tumor cells expressing CD19 ligand, can be irradiated at 30 Gy. SMART-expressing BMDMs are isolated by MACS (Miltenyi Biotec) and plated on the 3T3-CD19-CD80 cells, other artificial CD19 expressing cells, or on CD19 expressing tumor cells. After 24, 48, or 72 hrs, conditioned media is collected and ELISA assays are performed to evaluate secretion of the cytokines IFN-a, IFN-b, IL-6, IL-12 p70, and TNF. BMDM cells expressing pro-repair SMART vectors that signal through RTK or ITAM domain receptors may secrete significantly more IL-12, p70, and TNF upon simulation with multimerized ligand than control BMDM cells. The presence of ligands of pro-repair SMART receptors may reduce the expression levels of IL-12, p70, and TNF.

Example 8: Induction of the Anti-Inflammatory Cytokine IL-10 in Bone Marrow-Derived Myeloid Precursor Cells by Pro-Repair SMART Vectors in the Presence of Ligand Bone marrow-derived myeloid precursor cells expressing pro-repair SMART receptors may show an increase in the anti-inflammatory cytokine IL-10 in the context of multimerized or aggregated ligand forms, a high local concentration of ligand, stimulation with 100 ng/ml LPS (Sigma), and co-culturing with apoptotic cells.

Isolation of bone marrow-derived myeloid precursor cells is performed as follows. Bone marrow cells are isolated from adult 6-8 week-old female C57BL/6 mice (Charles River, Sulzfeld, Germany) from the medullary cavities of the tibia and femur of the hind limbs. Removal of erythrocytes is performed by lysis with a hypotonic solution. Cells are cultured in DMEM medium (Invitrogen) containing 10% fetal calf serum (Pan Biotech) and 10 ng/ml of GM-CSF (R&D Systems) in 75 $cm^2$ culture flasks (Greiner Bio-One). After 24 h, non-adherent cells are collected and re-seeded in fresh 75 $cm^2$ culture flasks. Medium is changed after 5 d and cells are cultured for an additional 10-11 d. The remaining cells are bone marrow-derived myeloid precursor cells, and are transduced with SMART vectors such as SMART1 or SMART11-15. The transduced cells are then examined for the level of IL-10 in conditioned media in both the presence and absence of receptor ligand (e.g., ligand on the surface of CD19-expressing B cell lineage tumor cells), LPS, or apoptotic cells.

Ligand for SMART expressing myeloid cells may be presented on tumor cells or artificial antigen expressing cells; alternatively the multimerized ligand or epitopes may be presented free of cells. For example, for cell-bound ligand, human CD19 and CD80 expressing fibroblasts such as 3T3-CD19-CD80 cells (Latouche and Sadelain, Nat Biotechnol, 405-409, 2000, Brentjens, Riviere et al., Blood, 4817-4828, 2011), or tumor cells expressing CD19 ligand, can be irradiated at 30 Gy. SMART-expressing bone marrow-derived myeloid precursor cells are isolated by MACS (Miltenyi Biotec) and plated on the 3T3-CD19-CD80 cells, other artificial CD19 expressing cells, or on CD19 expressing tumor cells.

Supernatant is collected after 24 h, and the level of IL-10 released from the cells is determined by IL-10 ELISA according to manufacturer's instructions (QuantikineM mouse IL-10, R&D Systems) (JEM (2005), 201; 647-657; and PLoS Medicine (2004), 4|Issue 4|e124).

Example 9: Increased Toll-Like Receptor (TLR) Responses in Macrophages Expressing Pro-Inflammatory SMART Vectors in the Presence of Ligand Signaling through pro-inflammatory SMART receptors (e.g., through local activation of TLR5, 1-4BB, CD28, or CD3Zeta) in the context of multimerized or aggregated ligand or high local ligand concentration, may locally enhance TLR responses in macrophages or mimic such responses in the absence of TLR ligands.

To elicit primary macrophages, mice are treated with 1.5 ml of 2% thioglycollate medium by intraperitoneal injection, and cells are then isolated by peritoneal lavage. To generate BMDM, total bone marrow is cultured in DMEM supplemented with 10% bovine calf serum, 5% horse serum, and 6 ng/ml recombinant human CSF-1 (R&D Systems). Cells are cultured for 5-6 days, and adherent cells are detached with 1 mM EDTA in PBS. Cells are stained with commercially available antibodies, including anti-CD11b, anti-CD40, anti-GR1 (BD Pharmingen), and F4/80 (Caltag Laboratories).

BMDM are re-plated and allowed to adhere for 4 h at 37° C., and then TLR agonists, such as LPS (*Salmonella abortus equi*), zymosan (*Saccharomyces cerevisiae*), and CpG 1826 DNA (purchased from e.g., Sigma-Aldrich) are added.

Ligand for SMART expressing myeloid cells may be presented on tumor cells or artificial antigen expressing cells; alternatively the multimerized ligand or epitopes may be presented free of cells. For example, for cell-bound ligand, human CD19 and CD80 expressing fibroblasts such as 3T3-CD19-CD80 cells (Latouche and Sadelain, Nat Biotechnol, 405-409, 2000, Brentjens, Riviere et al., Blood, 4817-4828, 2011), or tumor cells expressing CD19 ligand, can be irradiated at 30 Gy. SMART-expressing BMDMs are isolated by MACS (Miltenyi Biotec) and plated on the 3T3-CD19-CD80 cells, other artificial CD19 expressing cells, or on CD19 expressing tumor cells.

Cell culture supernatant is collected 24 h after stimulation and the levels of IFN-a4, IFN-b, IL-6, IL-12 p70, and TNF cytokines are measured by ELISA or by cytometric bead array (BD Biosciences mouse inflammation kit).

Example 10: Inhibited Expression of Anti-Inflammatory Cytokine IL-10 in Bone Marrow-Derived Myeloid Precursor Cells Expressing Pro-Inflammatory SMART Vectors in the Presence of Ligand Bone marrow-derived myeloid precursor cells expressing pro-inflammatory SMART receptors may show a decrease in the anti-inflammatory cytokine IL-10 in the context of multimerized or aggregated ligand, high local ligand concentration, stimulation with 100 ng/ml LPS (Sigma), and co-culturing with apoptotic cells.

Isolation of bone marrow-derived myeloid precursor cells is performed as follows. Bone marrow cells are isolated from adult 6-8 week-old female C57BL/6 mice (Charles River, Sulzfeld, Germany) from the medullary cavities of the tibia and femur of the hind limbs. Removal of erythrocytes is performed by lysis with a hypotonic solution. Cells are cultured in DMEM medium (Invitrogen) containing 10% fetal calf serum (Pan Biotech) and 10 ng/ml of GM-CSF (R&D Systems) in 75 cm$^2$ culture flasks (Greiner Bio-One). After 24 h, non-adherent cells are collected and re-seeded in fresh 75 cm$^2$ culture flasks. Medium is changed after 5 d and cells are cultured for an additional 10-11 d. The remaining cells are bone marrow-derived myeloid precursor cells, and are transduced with SMART pro-inflammatory receptors. The transduced cells are then examined for the level of IL-10 in conditioned media in both the presence and absence of an appropriate SMART receptor ligand, present at an appropriate concentration or ratio to the myeloid cells as determined by titration. Supernatant is collected after 24 h, and the level of IL-10 released from the cells is determined by IL-10 ELISA according to the manufacturer's instructions (QuantikineM mouse IL-10, R&D Systems) (JEM (2005), 201; 647-657; and PLoS Medicine (2004), 4|Issue 4|e124).

Example 11: SMART Ligand-Mediated Induction of the Expression of CD83 and CD86 on Human Dendritic Cells (DCs) Expressing Pro-Repair SMART Receptors The ability of pro-repair SMART receptors to inducibly modify expression of CD83 and CD86 is evaluated.

SMART vector transduced myeloid cells are generated as described above. On day 5 of monocyte differentiation to dendritic cells, immature human DCs are harvested and plated at 1 million cells per well and incubated at 37C, 5% CO$_2$ in the absence of cytokine. FACS analysis of CD86, CD83, CD11c, HLA-DR, and LIN (BD Biosciences) is performed on a BD FACS Canto 48 hours later. Data analysis is performed with FlowJo (TreeStar) software version 10.0.7. Levels of CD83 and CD86 are evaluated on CD11c+HLA-DR+LIN− cell populations.

Alternatively, Day 5 immature human dendritic cells are plated at 100,000 cells per well in a U-bottom non-TC treated 96 well plate in media without cytokine, with or without LPS-removed anti-human secondary antibody (Jackson ImmunoResearch) at 20 ug/ml. FACS analysis for CD86, CD83, CD11c, HLA-DR, and LIN (BD Biosciences) is performed 48 hrs post antibody addition.

Ligand for SMART expressing myeloid cells may be presented on tumor cells or artificial antigen expressing cells; alternatively the multimerized ligand or epitopes may be presented free of cells. For example, for cell-bound ligand, human CD19 and CD80 expressing fibroblasts such as 3T3-CD19-CD80 cells (Latouche and Sadelain, Nat Biotechnol, 405-409, 2000, Brentjens, Riviere et al., Blood, 4817-4828, 2011), or tumor cells expressing CD19 ligand, can be irradiated at 30 Gy. SMART-expressing human dendritic cells are isolated by MACS (Miltenyi Biotec) and plated on the 3T3-CD19-CD80 cells, other artificial CD19 expressing cells, or on CD19 expressing tumor cells.

The presence of multimerized or aggregated forms of SMART receptor ligand may increase the frequency of CD83+CD86+ DCs compared to the absence of such ligand.

Example 12: SMART Receptor Ligand-Mediated Induction of Syk Phosphorylation in SMART Transduced Myeloid Cells Spleen tyrosine kinase (Syk) is an intracellular signaling molecule that functions downstream of DAP12, CD3Zeta, and other ITAM signaling modules by phosphorylating several substrates, thereby facilitating the formation of a signaling complex leading to cellular activation and inflammatory processes. The ability of SMART receptor ligands to induce Syk activation in SMART transduced myeloid cells is determined by culturing transduced human or mouse macrophages or primary human dendritic cells and measuring the phosphorylation state of Syk protein in cell extracts.

Bone marrow-derived macrophages (BMDM) or primary human dendritic cells are starved for 4 hours in 1% serum RPMI, removed from tissue culture dishes with PBS-EDTA, washed with PBS, and counted.

Next, Lentiviral mediated transduction of the cells with vectors encoding SMART1, SMART11, SMART12, SMART13, SMART14, SMART15, SMART16, or other chimeric receptors is performed. Monocytes are isolated from buffy coats of healthy donors following Lymphoprep gradient centrifugation and positive or negative magnetic antibody separation (Miltenyi Biotec, Leiden, Netherlands). Purity is assessed by flow cytometry of anti-CD14-PE stained cells. Isolated cells are cultured. Cells are matured to the appropriate phenotype. To ensure standardized transduction, lentiviral supernatants are titrated. Cells are plated in a 96-well plate at 50,000 cells/well and infected (50 ng p24) by spinoculation (90 min, 950 g, 32° C.), with continuous spinning in a centrifuge, in presence of 1 µM ritonavir (NIH AIDS Reagent Program, Germantown, Md.) in a final volume of 200 µL. On day 1 post-infection, medium is refreshed. Infection is measured on day 3 by flow cytometry, gaiting on live cells as determined by propidium iodide staining (Miltenyi Biotec).

Viral reverse transcriptase (RT) activity, quantitative realtime qPCR for viral DNA of long terminal repeat sequences, or ELISA of p24 viral protein are performed using standard techniques. Supernatant of lentiviral vector encoding a scrambled sequence or an eGFP marker gene showed an MOI of 10 when measured on 293T cells and provided over 95% transduction efficiency. This lentiviral supernatant expressed RT activity of 5,550 mU/ml (equivalent of 1 µg of p24/ml as assessed by ELISA) in previous studies. Aliquots of this supernatant are included in all subsequent reverse transcriptase activity assays to serve as a standard reference for viral production.

On day 1 post isolation, medium is replaced with fresh medium containing 50% lentiviral supernatant. RT activity of 2,750-5,550 mU/ml is used. Cells are subsequently spinoculated (90 min, 950 g, 32° C.) in the presence of polybrene (4 µg/mL; Sigma-Aldrich, Diegem, Belgium).

Medium is refreshed 24 h post-transduction and cells are cultured using standard methods.

To generate virus, transfection of vectors into 293T cells is performed using standard approaches. Viral production is achieved using standard second or third-generation lentiviral transduction vector packaging production kits, such as Virapower (Life Technologies/Fisher Scientific) using the manufacturer's instructions. The titer of the viral supernatants is measured by quantification of reverse transcriptase activity via real time-PCR and expressed as equivalent p24.

Although lentiviral vectors can be inhibited in human myeloid cells, Witkowski et al. (Witkowski, Vermeire et al., PLoS One, e0133651, 2015) optimized the transduction of myeloid cells by investigating the effect of a range of parameters, including additives such as polybrene, spinoculation, and experimental timeline. This optimized protocol is subsequently used in the experiments described herein. Transduction is performed by spinoculation as described above in the presence of polybrene, which can facilitate virus-cell binding and entry. To measure transduction efficiency, a pLKO.1-derived lentiviral vector encoding an eGFP marker gene is used. Transduction efficiency, as well as the macrophage phenotype, is evaluated five days post-transduction.

The cells are then treated on ice with ligand aggregates, ligand multimers, or placed into wells that have been coated with plate-bound ligand. After washing with cold PBS, cells are lysed with lysis buffer (1% v/v NP-40%, 50 Mm Tris-HCl (pH 8.0), 150 mM NaCl, 1 mM EDTA, 1.5 mM MgCl2, 10% glycerol, plus protease and phosphatase inhibitors) followed by centrifugation at 16,000 g for 10 min at 4° C. to remove insoluble materials. Lysates are then immunoprecipitated with anti-Syk Ab (N-19 for BMDM or 4D10 for human DCs, Santa Cruz Biotechnology). Precipitated proteins are fractionated by SDS-PAGE, transferred to PVDF membranes, and probed with anti-phosphotyrosine Ab (4G10, Millipore). To confirm that all substrates are adequately immunoprecipitated, immunoblots are reprobed with anti-Syk Ab (Abcam, for BMDM or Novus Biological, for human DCs). Visualization is performed with the enhanced chemiluminescence (ECL) system (GE healthcare) (Peng et al., (2010) Sci Signal., 3(122): ra38).

Cells transduced with SMART vectors that harbor ITAM domains such as CD3Zeta or DAP12, may induce SYK phosphorylation selectively in the presence but not the absence of antigen (e.g., multimerized, aggregated, or plate-bound ligand).

Example 13: SMART Receptor Ligand-Mediated Induction of DAP12 Phosphorylation in Mouse Macrophages Expressing SMART Receptors TREM2 signals through DAP12, leading downstream to activation of PI3K and other intracellular signals. The ability of SMART ligands to induce DAP12 activation is determined by culturing mouse macrophages expressing cognate SMART receptors and measuring the phosphorylation state of DAP12 protein in cell extracts.

Next, Lentiviral mediated transduction of the cells with vectors encoding SMART1, SMART11, SMART12, SMART13, SMART14, SMART15, SMART16, or other chimeric receptors is performed. Monocytes are isolated from buffy coats of healthy donors following Lymphoprep gradient centrifugation and positive or negative magnetic antibody separation (Miltenyi Biotec, Leiden, Netherlands). Purity is assessed by flow cytometry of anti-CD14-PE stained cells. Isolated cells are cultured. Cells are matured to the appropriate phenotype. To ensure standardized transduction, lentiviral supernatants are titrated. Cells are plated in a 96-well plate at 50,000 cells/well and infected (50 ng p24) by spinoculation (90 min, 950 g, 32° C.), with continuous spinning in a centrifuge, in presence of 1 µM ritonavir (NIH AIDS Reagent Program, Germantown, Md.) in a final volume of 200 µL. On day 1 post-infection, medium is refreshed. Infection is measured on day 3 by flow cytometry, gaiting on live cells as determined by propidium iodide staining (Miltenyi Biotec).

Viral reverse transcriptase (RT) activity, quantitative realtime qPCR for viral DNA of long terminal repeat sequences, or ELISA of p24 viral protein are performed using standard techniques. Supernatant of lentiviral vector encoding a scrambled sequence or an eGFP marker gene showed an MOI of 10 when measured on 293T cells and provided over 95% transduction efficiency. This lentiviral supernatant expressed RT activity of 5,550 mU/ml (equivalent of 1 µg of p24/ml as assessed by ELISA) in previous studies. Aliquots of this supernatant are included in all subsequent reverse transcriptase activity assays to serve as a standard reference for viral production.

On day 1 post isolation, medium is replaced with fresh medium containing 50% lentiviral supernatant. RT activity of 2,750-5,550 mU/ml is used. Cells are subsequently spinoculated (90 mM, 950 g, 32° C.) in the presence of polybrene (4 µg/mL; Sigma-Aldrich, Diegem, Belgium). Medium is refreshed 24 h post-transduction and cells are cultured using standard methods.

To generate virus, transfection of vectors into 293T cells is performed using standard approaches. Viral production is achieved using standard second or third-generation lentiviral transduction vector packaging production kits, such as Virapower (Life Technologies/Fisher Scientific) using the manufacturer's instructions. The titer of the viral supernatants is measured by quantification of reverse transcriptase activity via real time-PCR and expressed as equivalent p24 as described above.

Although lentiviral vectors can be inhibited in human myeloid cells, Witkowski et al. (Witkowski, Vermeire et al., PLoS One, e0133651, 2015) optimized the transduction of myeloid cells by investigating the effect of a range of parameters, including additives such as polybrene, spinoculation, and experimental timeline. This optimized protocol is subsequently used in the experiments described herein. Transduction is performed by spinoculation as described above in the presence of polybrene, which can facilitate virus-cell binding and entry. To measure transduction efficiency, a pLKO.1-derived lentiviral vector encoding an eGFP marker gene is used. Transduction efficiency, as well as the macrophage phenotype, is evaluated five days post-transduction.

Before stimulation with ligands, mouse wild-type (WT) bone marrow-derived macrophages (BMDM) and TREM2 knockout (KO) BMDM are starved for 4h in 1% serum RPMI. $15 \times 10^6$ cells are incubated on ice for 15 min.

Cells are washed and incubated at 37° C. After stimulation with ligands, cells are lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors), followed by centrifugation at 16,000 g for 10 min at 4° C. to remove insoluble materials. Cell lysate is immunoprecipitated with a TREM2 antibody (R&D Systems) for total DAP12, or an antibody to human IgH variable domain (for selectively isolating the SMART receptor). Precipitated proteins are fractionated by SDS-PAGE, transferred to PVDF membranes, and probed with anti-phosphotyrosine antibody (4G10, Millipore). The membrane is stripped and reprobed with anti-DAP12 antibody (Cells Signaling, D7G1X). Each cell lysate used for TREM2 immunoprecipitations contains an equal amount of proteins, as indicated by a control Ab (anti-actin, Santa Cruz). DAP12 can be phosphorylated in macrophages transduced with a pro-repair SMART chimeric receptor, in the presence of multimerized or aggregated cognate ligand.

Example 14: SMART Ligand-Mediation Modulation of the Expression of Inflammatory Cell Surface Markers on Mouse or Human Macrophages Expressing Cognate Chimeric SMART Receptors In order to validate the regulation of inflammatory marker expression by SMART vectors, mouse or human macrophages are cultured with various inflammatory mediators, and the expression of surface markers CD86 and CD206 is measured.

Macrophages are isolated from mice or humans and transduced or transfected with SMART vectors. Cells are allowed to adhere for 4 h at 37° C., and TLR agonists LPS (*Salmonella abortus* equi) and zymosan (*Saccharomyces cerevisiae*) are added at concentrations ranging from 0.01-100 ng/ml (LPS) or 0.01-10 µg/ml (zymosan). FACS analysis of CD86 and CD206 is performed on a BD FACS Canto 48 hours later. Data analysis is performed with FlowJo (TreeStar) software version 10.0.7.

Macrophages transduced with pro-repair SMART receptors and treated with inflammatory mediators IFN-γ, LPS, or Zymosan in presence of cognate ligand may express lower levels of the inflammatory receptor CD86 but not of the receptor CD206 compared to macrophages not exposed to ligand. In contrast, macrophages transduced with pro-inflammatory SMART receptors and treated with inflammatory mediators IFN-γ, LPS, or Zymosan in the presence of cognate ligand (e.g., CD19-expressing B cell lineage tumor cells for SMART1 or SMART11-16) may express higher levels of the inflammatory receptor CD86 but not of the receptor CD206 compared to macrophages not exposed to ligand.

Example 15: SMART Ligand-Mediated Increase in the Survival of Mouse or Human Myeloid Cells Expressing Cognate Chimeric SMART Receptors To evaluate the ability of SMART receptors to induce myeloid cell survival, mouse or human macrophages are transduced with SMART receptors and cultured in the presence of inflammatory mediators, along with or in the absence of cognate SMART receptor ligands. Cell survival is subsequently measured.

Murine bone marrow precursor cells are obtained by flushing tibial and femoral marrow cells with cold PBS. After one wash with PBS, erythrocytes are lysed using ACK Lysing Buffer (Lonza), washed twice with PBS, and suspended at $0.5 \times 10^6$ cells/ml in complete RPMI media (10% FCS, Pen/Strep, Gln, neAA) with 50 ng/ml M-CSF to produce macrophages or 10 ng/ml GM-CSF to produce dendritic cells. For M2-type macrophages, 10 ng/ml IL-4 is added to the cultured cells. For M1-type macrophages, 50 ng/ml IFN-γ is added. In some experiments LPS or zymosan is added to the cell culture at day 5 at a concentration range of 1 µg/ml-0.01 ng/ml. Recombinant cytokines are purchased from Peprotech.

Cells are transduced or transfected with a single SMART vector alone or any combination of SMART vectors. To analyze viability of bone marrow-derived macrophages, cells are prepared as above and cultured in MCSF. Cells are either plated at $10^5/200$ µl in a 96-well plate (for viability analysis using a luciferase based-assay) or at $0.5\times10^6/1$ ml in a 6-well plate (for Trypan Blue exclusion cell count) in non-tissue culture treated plates. Media containing fresh M-CSF is added at day 3. Cells are gently detached from the plates with 3 mM EDTA and counted using a Burker chamber. For FACS analysis of live cells, macrophages are cultured either in 50 ng/ml MCSF for 6 days (+MCSF) or in 50 ng/ml MCSF for 4 days before MCSF is removed for an additional 36 hrs (−MCSF). Cells are stained using CD11b antibody and DAPI. For luciferase viability assays, cell viability is measured at day 5 of culture in graded concentrations of growth factors GMCSF (dendritic cells), MCSF (M1 macrophages), or MCSF+IL-4 (M2 macrophages). Cells are directly incubated with ToxGlo reagent (Promega) and luciferase activity (luminescence) is read using an XY reader. For FACS analysis of viable macrophages cultured in the presence of inflammatory mediators IFN-γ, LPS, or zymosan, cells are collected at day 5 and stained using CD11b antibody and DAPI.

Ligand for SMART expressing myeloid cells may be presented on tumor cells or artificial antigen expressing cells; alternatively the multimerized ligand or epitopes may be presented free of cells. For example, for cell-bound ligand, human CD19 and CD80 expressing fibroblasts such as 3T3-CD19-CD80 cells (Latouche and Sadelain, Nat Biotechnol, 405-409, 2000, Brentjens, Riviere et al., Blood, 4817-4828, 2011), or tumor cells expressing CD19 ligand, can be irradiated at 30 Gy. SMART-expressing macrophages are plated on the 3T3-CD19-CD80 cells, other artificial CD19 expressing cells, or on CD19 expressing tumor cells.

After culture in MCSF with cognate ligand, a significantly higher numbers of viable (trypan blue excluded) SMART-transduced macrophages may be observed than macrophages transduced with an empty vector or a SMART vector that does not recognize the ligand. FACS analysis may reveal that SMART-expressing macrophages, cultured with or without MCSF along with an appropriate stimulatory ligand, can display increased survival compared to cells lacking SMART vectors, as indicated by a higher percentage of live (CD11b+DAPI−) cells. For luciferase assays, SMART-expressing cells cultured in the presence of growth factors GMCSF (dendritic cells), MCSF (M1 macrophages), or MCSF+IL-4 (M2 macrophages), at any or all time points during the analysis, may survive better than cells lacking a SMART receptor or stimulating ligand, as indicated by a higher luminescence reading across the range of growth factor concentrations.

Example 16: Isolation of Monocytes from the Peripheral Blood of Mice

Six-month-old adult mice or 2 week old young mice (C57BL/6N; Charles River, Germany) are given an intraperitoneal overdose of sodium thiopental (12.5 mg; Sandoz, Austria) and perfused with 20 ml of 10 mM phosphate-buffer saline (PBS)/2.7 mM (5.5 mM) EDTA/25 mg/ml heparin, pH 7.3 through the left ventricle. The collected effluent is centrifuged at 550×g for 10 min at 4° C. The cell pellet is then resuspended in 4 ml of PBS/EDTA solution and 380 µl (40 µl/1×$10^6$ target cells) of S-pluriBead suspension (pluriBead S-Bead CD11b Cell Separation KIT, pluriSelect) is added and incubated for 30 min on a pluriSelect pluriPlix at ~10 rpm/7.5° angle at room temperature. Following the incubation, the cell suspension is poured directly onto the strainer and then washed 14× with 1 ml of wash buffer in a circular motion. Following attachment of the provided connector, tube and strainer, 1 ml of detachment buffer is carefully added to the strainer (containing the isolated CD11b target cells) and the cells are then incubated for 10 min at room temperature. Following incubation, 1 ml of wash buffer is added to the strainer and cells are separated from the beads by pipetting up and down (10×). The Luer-Lock is opened and 1 ml of wash buffer is added to allow detached CD11b+ cells to run into the provided tube. The strainer is then washed 10× with 1 ml of wash buffer. The cells are then centrifuged at 250×g for 10 min. The supernatant is carefully discarded and cells are resuspended in 100 µl of desired vehicle (e.g., FACS or infusion buffer). Approximately 10.7±0.8 million (n=8) cells are isolated from one animal.

Example 17: Delivery of Immature Dendritic Cells In Vivo

A DC-enriched population is generated from bone marrow using methods know in the art. After RBC lysis and washing with RPMI (Gibco, Grand Island, N.Y., USA), cells are resuspended in freezing media (Gibco), and stored in liquid nitrogen. Upon rapid thawing, cells are washed with RPMI (Gibco) and seeded in 6-well plates at a concentration of 2×$10^6$ cells/mL in complete media: RPMI 1640 (Gibco), 10% fetal bovine serum (fetal bovine serum, Gibco), 2 mmol/L L-glutamine (Gibco), 1% nonessential amino acids (Gibco), 1 mmol/L sodium pyruvate (Gibco), 1% penicillin-streptomycin and the cytokines, interleukin-4, granulocyte-macrophage colony stimulating factor, Flt-3 ligand (all at 5 ng/mL/cytokine, RD Systems, Minneapolis, Minn., USA). On the third day in vitro (DIV 3), 1 mL/well of complete media is added. On DIV 4, media containing non-adherent cells is removed and replaced with 0.75 mL complete media containing 10 µg/mL protamine sulfate (Sigma, St Louis, Mo., USA) and cells are transduced with a lentiviral vector (LV) encoding a SMART chomeric receptor (multiplicity of infection (MOI)=10 to 30). Eighteen hours post LV transduction, virus-containing media is replaced with a combination of 75% complete media and 25% spun-down conditioned media from DIV 4. On DIV 6 to 7, cultures are harvested in their media, spun at 1,300 r.p.m. at room temperature, and resuspended in RPMI. Modified dendritic cells are then transfused. A catheter is inserted into the carotid artery and 2×$10^6$ dendritic cells are infused (0.3 mL over 1 minute), 2.5×$10^6$ cells are injected over 1 minute, or vehicle (50% RPMI 1640/50% complete media without cytokines) is injected over 1 minute. After infusion, the catheter is removed, the artery sutured, and the wound closed.

At subsequent time points of 1 day, 3 days, 7 days, 14 days, and 1 month, peripheral cells, spleen cells, and bone marrow cells are isolated using standard methods. Analysis of genomic DNA from each of these tissues by PCR using primers selective for sequences within SMART vectors may demonstrate the presence of cells that harbor SMART vectors. Furthermore, SMART cells transduced into mice that harbor cells (such as tumor cells) or tumors that express the CD19 ligand may expand and be at significantly higher levels in such mice. Isolation and DNA analysis of tumor tissue from mice harboring tumors expressing a SMART ligand (such as CD19) in mice transduced with SMART cells expressing vectors selective for the cognate tumor antigen (such as CD19) may show expansion of the SMART cell population. This may indicate increased presence of the SMART vector DNA sequence as assessed by quantitative PCR. Similarly, Immunohistochemical or FACS analysis of tumor tissue may show an increased presence of SMART-transduced myeloid cells in the context of tumors that harbor a cognate ligand, such as CD19. Increased presence of myeloid cells can be identified by typical markers, including CD11b and CD40.

Example 18: Induction of CCR7 and Migration Toward CCL19 and CCL21 in SMART Vector-Modified Microglia, Macrophages, and Dendritic Cells in the Presence of Ligand In the presence of ligand, SMART-modified myeloid cells may induce CCR7 and migration toward CCL19 and CCL21 in microglial cells, macrophages, and dendritic cells. Microglial, macrophages or dendritic cells are either cultured with cognate ligand, or control media only. Cells are collected after 72 h, immuno-labeled with CCR7 specific anti-bodies, and analyzed by flow cytometry. To determine any functional consequences of increased CCR7 expression, a chemotaxis assay is performed. Microglia, macrophages or dendritic cells are stimulated with ligand or media control and placed in a two-chamber system. The number of cells migrating toward the chemokine ligands CCL19 and CCL21 is quantified (JEM (2005), 201, 647-657). For the chemotaxis assay, microglial, macrophages or dendritic cells are exposed to the ligand with or without treatment with 1 µg/ml LPS. SMART expressing microglia, macrophages or dendritic cells are transferred into the upper chamber of a transwell system (3 µm pore filter; Millipore) containing 450 µl medium with 100 ng/ml CCL19 or CCL21 (both from PeproTech) in the lower chamber. After a 1 h incubation period, the number of microglia, macrophages, or dendritic cells that have migrated to the lower chamber is counted in three independent areas by microscopy (JEM (2005), 201, 647-657).

Example 19: Ability of Connate Ligands to Increase the Survival of SMART Chimeric Receptor-Expressing Macrophages and Dendritic Cells To evaluate the role of SMART chimeric receptors in cell survival, SMART vector-expressing macrophages and dendritic cells are cultured in the presence of cognate ligand and cell viability is determined.

Murine bone marrow precursors are obtained by flushing tibial and femoral marrow cells with cold PBS. After one wash with PBS, erythrocytes are lysed using ACK Lysing Buffer (Lonza), washed twice with PBS and suspended at $0.5 \times 10^6$ cells/ml in complete RPMI media (10% FCS, Pen/Strep, Gln, neAA) with the indicated amounts of 50 ng/ml M-CSF to produce macrophages, or 10 ng/ml GM-CSF to produce dendritic cells. For M2-type macrophages, 10 ng/ml IL-4 is added to the cultured cells. For M1-type macrophages, 50 ng/ml IFN-γ is added. In some experiments LPS or zymosan is added to the cell culture at day 5 at a concentration range of 1 µg/ml-0.01 ng/ml. Recombinant cytokines are purchased from Peprotech.

To analyze viability of bone marrow-derived macrophages, cells are prepared as above and cultured in MCSF. Cells are transduced, transfected, or otherwise modified to express SMART chimeric receptors using the techniques described above. Cells harboring SMART vectors or control vector only are either plated at $10^5/200$ µl in a 96-well plate (for viability analysis using a luciferase based-assay) or at $0.5 \times 10^6/1$ ml in a 6-well plate (for Tripan Blue exclusion cell count) in non-tissue culture treated plates. Media containing fresh M-CSF is added at day 3, with or without cognate ligand for the SMART receptors. At indicated time points cells are gently detached from the plates with 3 mM EDTA and counted using a Burker chamber. For FACS analysis of live cells, macrophages are cultured either in 50 ng/ml MCSF for 6 days (+MCSF) or in 50 ng/ml MCSF for 4 days before MCSF is removed for an additional 36 hrs (−MCSF). Cells are stained using CD11b antibody and DAPI. For luciferase viability assays, cell viability is measured at day 5 of culture in graded concentrations of growth factors GMCSF (dendritic cells), MCSF (M1 macrophages), or MCSF+IL-4 (M2 macrophages). Cells are directly incubated with ToxGlo reagent (Promega) and luciferase activity (luminescence) is determined. For FACS analysis of viable macrophages cultured in the presence of inflammatory mediators IFN-γ, LPS, or zymosan, cells are collected at day 5 and stained using CD11b antibody and DAPI. All experiments are conducted in the presence or absence of cognate ligand for the SMART receptors.

Example 20: Analysis of the Anti-Cancer Effect of SMART Receptor-Expressing Myeloid Cells in a Mouse Model of Breast Cancer Groups of 10 BALB/c mice at 8 weeks (+/−2 weeks) of age are challenged subcutaneously with $5 \times 10^6$ EMT-6 tumor cells suspended in 100 ul PBS. Animals are anesthetized with isoflurane prior to implant. Starting at day 2, groups of mice are injected IV, intra-arterially, IP, or intra-tumor with SMART vector-expressing myeloid cells at 10^5 cells/mouse or more, 10^6 cells per mouse or more, 10^7 cells per mouse or more, or >10^8 cells. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate, reduced number of tumor infiltrating immune suppressor macrophages, and increased effector T cell influx into the tumor may indicate the anti-cancer effects of SMART receptor-expressing myeloid cells.

Example 21: Analysis of Additive Anti-Tumor Effect of Combination Therapy that Combines SMART Cell Therapies with Antibodies Against Inhibitory Checkpoint Proteins or Inhibitory Cytokines/Chemokines and their Receptors in a Mouse Model of Breast Cancer Groups of 10 BALB/c mice at 8 weeks (+/−2 weeks) of age are challenged subcutaneously with 5×106 EMT-6 tumor cells suspended in 100 ul PBS. Animals are anesthetized with isoflurane prior to implant. Starting at day 2, groups of mice are injected IV, intra-arterially, IP, or intra-tumor with SMART vector-expressing myeloid cells at 10^5 cells/mouse or more, 10^6 cells per mouse or more, 10^7 cells per mouse or more, or >10^8 cells alone or in combination with antibodies against checkpoint proteins (e.g., anti-PDL1 mAb clone 10E9G2 and/or anti-CTLA-4 mAb clone 9H10) at day 8 and 11. Treatment groups include SMART-myeloid cells; anti-CTLA-4; SMART-myeloid cells+anti-CTLA-4 and isotype control. Tumor growth is monitored with a caliper biweekly to measure tumor growth starting at day 4. The endpoint of the experiment is a tumor volume of 2000 mm3 or 60 days. Tumor growth and % survival are the outcome measures. A decrease in tumor growth and an increase in percent survival with combination therapy may indicate that SMART-expressing myeloid cells have additive or synergistic therapeutic effects with anti-checkpoint antibodies. Antagonistic antibodies against checkpoint molecules include antibodies against PDL1, PDL2, PD1, CTLA-4, B7-H3, B7-H4, HVEM, BTLA, KIR, GAL9, TIM3, A2AR, LAG-3, and phosphatidylserine (PS). Antagonist antibodies against inhibitory cytokines include antibodies against CCL2, CSF-1, and IL-2.

Example 22: Analysis of Additive Anti-Tumor Effect of Combination Therapy that Combines SMART-Expressing Myeloid Cells with Antibodies that Activate Stimulatory Checkpoint Proteins Groups of 15 C57B16/NTac mice at 8 weeks (+/−2 weeks) of age are challenged subcutaneously with tumor cells as described in Example 21 Animals are anesthetized with isoflurane prior to implant. Starting at day 2, mice are injected IV, intra-arterially, IP, or intra-tumor with SMART vector-expressing myeloid cells at 10^5 cells/mouse or more, 10^6 cells per mouse or more, 10^7 cells per mouse or more, or >10^8 cells alone or in combination with agonistic antibodies that activate stimulatory checkpoint proteins (e.g., OX40 or ICOS mAb) at day 3, 6, and 9. Tumor growth is monitored with a caliper biweekly to measure tumor growth starting at day 4. The endpoint of the experiment is a tumor volume of 2000 mm$^3$ or 60 days. Tumor growth and percent survival are the outcome measures. A decrease in tumor growth and an increase in percent survival with combination therapy may indicate that SMART-expressing myeloid cells have additive or synergistic therapeutic effects with stimulatory checkpoint antibodies. Stimulatory checkpoint antibodies include agonistic/stimulatory antibodies against CD28, ICOS, CD137, CD27, CD40, and GITR.

Example 23: Analysis of Additive Anti-Tumor Effect of Combination Therapy that Combines SMART-Expressing Myeloid Cells with Stimulatory Cytokines Groups of 15 C57B16/NTac mice at 8 weeks (+/−2 weeks) of age are challenged subcutaneously with tumor cells as described in Example 21 Animals are anesthetized with isoflurane prior to implant. Starting at day 2, mice are injected IV, intra-arterially, IP, or intra-tumor with SMART vector-expressing myeloid cells at 10^5 cells/mouse or more, 10^6 cells per mouse or more, 10^7 cells per mouse or more, or >10^8 cells alone or in combination with stimulatory cytokines (e.g., IL-12, IFN-α). Tumor growth is monitored with a caliper biweekly to measure tumor growth starting at day 4. The endpoint of the experiment is a tumor volume of 2000 mm$^3$ or 60 days. Tumor growth and percent survival are the outcome measures. A decrease in tumor growth and an increase in percent survival with combination therapy may indicate that SMART-expressing myeloid cells have additive or synergistic therapeutic effects with immune-stimulatory cytokines. Stimulatory cytokines include IFN-a/b, IL-2, IL-12, IL-18, GM-CSF, and G-CSF.

What is claimed is:

1. An isolated myeloid cell, wherein the myeloid cell comprises a chimeric receptor, wherein the chimeric receptor comprises:
   (1) an extracellular ligand-binding domain, wherein the extracellular ligand-binding domain comprises a CD19-specific single-chain variable fragment (scFv) domain:
   (2) a transmembrane domain, wherein the transmembrane domain comprises a toll-like receptor 5 (TLR5)transmembrane domain: and
   (3) a signaling domain, wherein the signaling domain comprises a CD3-zeta intracellular domain.

2. The myeloid cell of claim 1, wherein the signaling domain further comprises an intracellular domain selected from the group consisting of a CD28 intracellular domain and a 4-1BB intracellular domain.

3. The myeloid cell of claim 1, wherein the chimeric receptor comprises the amino acid sequence of SEQ ID NO: 26.

4. The myeloid cell of claim 1, wherein the myeloid cell is selected from the group consisting of macrophages, M1 macrophages, activated M1 macrophages, M2 macrophages, neutrophils, activated neutrophils, dendritic cells, monocytes, osteoclasts, Langerhans cells, Kupffer cells, microglia, M1 microglia, activated M1 microglia, M2 microglia, and any combination thereof.

5. The myeloid cell of claim 1, wherein the cell lacks one or more genes encoding one or more immune molecules that allow for recognition by the adaptive immune system.

6. The myeloid cell of claim 5, wherein the one or more immune molecules are MHC class I molecules, MHC class I co-receptors, MHC class II molecules, MHC class II co-receptors, or any combination thereof.

7. A method of treating a CD19-expressing cancer, comprising administering to an individual in need thereof a therapeutically effective amount of an isolated myeloid cell, wherein the myeloid cell comprises a chimeric receptor, wherein the chimeric receptor comprises:
   (1) an extracellular ligand-binding domain, wherein the extracellular ligand-binding domain comprises a CD19-specific single-chain variable fragment (scFv) domain:
   (2) a transmembrane domain, wherein the transmembrane domain comprises a toll-like receptor 5 (TLR5) transmembrane domain: and
   (3) a signaling domain, wherein the signaling domain comprises a CD3-zeta intracellular domain.

8. The method of claim 7, wherein the signaling domain further comprises an intracellular domain selected from the group consisting of a CD28 intracellular domain and a 4-1BB intracellular domain.

* * * * *